United States Patent
Guan et al.

(10) Patent No.: US 11,457,628 B2
(45) Date of Patent: Oct. 4, 2022

(54) SUBSTITUTED PYRIMIDINE COMPOUND AND PREPARATION METHOD AND USE THEREOF

(71) Applicants: SHENYANG SINOCHEM AGROCHEMICALS R&D CO., LTD., Liaoning (CN); JIANGSU YANGNONG CHEMICAL CO., LTD., Jiangsu (CN)

(72) Inventors: Aiying Guan, Liaoning (CN); Miao Li, Liaoning (CN); Junfeng Wang, Liaoning (CN); Leichuan Xu, Liaoning (CN); Qin Sun, Liaoning (CN); Xufeng Sun, Liaoning (CN); Jinqiang Sun, Liaoning (CN); Changling Liu, Liaoning (CN)

(73) Assignees: SHENYANG SINOCHEM AGROCHEMICALS R&D CO., LTD., Liaoning (CN); JIANGSU YANGNONG CHEMICAL CO., LTD., Jiangsu (CN)

(*) Notice: Subject to any disclaimer, the term of this patent is extended or adjusted under 35 U.S.C. 154(b) by 0 days.

(21) Appl. No.: 16/766,925

(22) PCT Filed: Nov. 22, 2018

(86) PCT No.: PCT/CN2018/116938
§ 371 (c)(1),
(2) Date: May 26, 2020

(87) PCT Pub. No.: WO2019/105275
PCT Pub. Date: Jun. 6, 2019

(65) Prior Publication Data
US 2021/0015100 A1    Jan. 21, 2021

(30) Foreign Application Priority Data

Nov. 29, 2017 (CN) .......................... 201711223040.2
Nov. 29, 2017 (CN) .......................... 201711223553.3

(51) Int. Cl.
*A01N 43/54* (2006.01)
*C07D 403/12* (2006.01)
*C07D 495/04* (2006.01)

(52) U.S. Cl.
CPC ........... *A01N 43/54* (2013.01); *C07D 403/12* (2013.01); *C07D 495/04* (2013.01)

(58) Field of Classification Search
CPC ..... A01N 43/54; C07D 403/12; C07D 495/04
See application file for complete search history.

(56) References Cited

U.S. PATENT DOCUMENTS

| 4,845,097 | A | 7/1989 | Matsumoto et al. |
| 4,977,264 | A | 12/1990 | Mills et al. |
| 4,985,426 | A | 1/1991 | Yoshioka et al. |
| 5,468,751 | A | 11/1995 | Kristiansen et al. |
| 6,090,815 | A | 7/2000 | Masuda |
| 9,682,962 | B2 | 6/2017 | Lie et al. |
| 11,008,339 | B2 * | 5/2021 | Liu ...................... C07D 401/14 |
| 2004/0092402 | A1 | 5/2004 | Kuragano et al. |
| 2010/0158860 | A1 | 6/2010 | Steiner et al. |
| 2018/0141961 | A1 | 5/2018 | Liu et al. |

FOREIGN PATENT DOCUMENTS

| CN | 102584705 A | 7/2012 |
| CN | 104710409 A | 6/2015 |
| CN | 104710436 A | 6/2015 |
| CN | 105777717 A | 7/2016 |
| CN | 106167484 A | 11/2016 |
| CN | 107778298 A | 3/2018 |
| CN | 108017628 A | 5/2018 |
| CN | 108059629 A | 5/2018 |

(Continued)

OTHER PUBLICATIONS

International Search Report for PCT/CN2018/116938, dated Feb. 11, 2019 (6pgs. with English translation).

(Continued)

*Primary Examiner* — Yong L Chu
(74) *Attorney, Agent, or Firm* — Smith, Gambrell & Russell, LLP

(57) ABSTRACT

The present invention discloses a substituted pyrimidine compound. The structure is shown in general formula I. The definition of each substituent in the formula is described in the description. The compound of the present invention has broad-spectrum fungicidal, insecticidal and acaricidal activity, and has excellent control effects on cucumber downy mildew, powdery mildew, corn rust, anthrax, rice blast, aphids, *Tetranychus cinnabarinus* and the like.

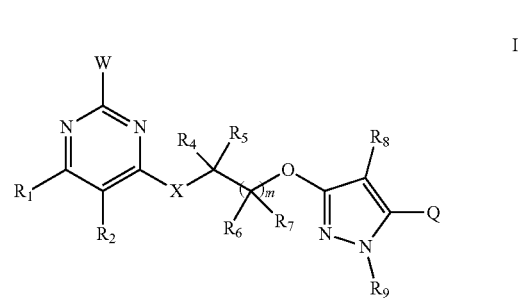

I

6 Claims, No Drawings

(56) References Cited

FOREIGN PATENT DOCUMENTS

| | | |
|---|---|---|
| CN | 108069984 A | 5/2018 |
| EP | 0 356 158 A1 | 2/1990 |
| JP | H09124613 A | 5/1997 |
| JP | 2000007662 A | 1/2000 |
| WO | 95/07278 | 3/1995 |
| WO | 2011/133444 A1 | 10/2011 |
| WO | 2016/184378 A1 | 11/2016 |
| WO | WO-2016184378 A1 * 11/2016 | ........... C07D 403/14 |

OTHER PUBLICATIONS

Written Opinion of the International Searching Authority for PCT/CN2018/116938, dated Feb. 11, 2019 (5pgs.).
International Preliminary Report on Patentability dated Jun. 2, 2020 in International Patent Application No. PCT/CN2018/116938 (6 pages in Chinese with English translation).
European Search Opinion dated Mar. 23, 2021 in European Patent Application No. 18882912.1 (8 pages).
Second Office dated May 17, 2021 in Chinese Patent Application No. 201711223040.2 (5 pages in Chinese with English translation).
First Office Action dated Dec. 21, 2020 in Chinese Patent Application No. 201711223553.3 (9 pages in Chinese with English translation).

* cited by examiner

SUBSTITUTED PYRIMIDINE COMPOUND AND PREPARATION METHOD AND USE THEREOF

TECHNICAL FIELD

The present invention belongs to the field of chemistry, and particularly relates to a substituted pyrimidine compound and a preparation method and use thereof as a fungicide, an insecticide and an acaricide.

BACKGROUND

Patent WO9507278 published the general formulas of pyrimidine-containing substituted pyrazole compounds as shown in the following general formulas and the application of specific compounds CK1 and CK2 as an agricultural fungicide, an insecticide and an acaricide.

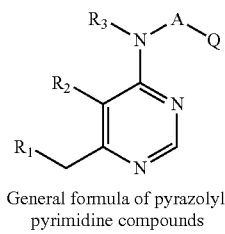

General formula of pyrazolyl pyrimidine compounds

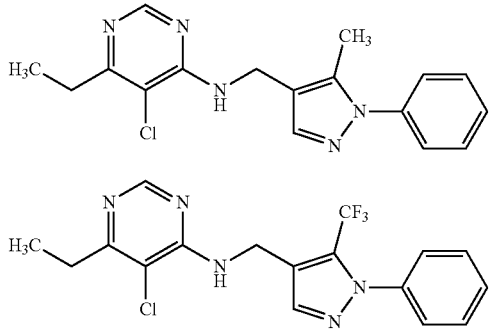

The following compounds CK3, CK4 and CK5 were searched online through Scifinder, but no reference was found.

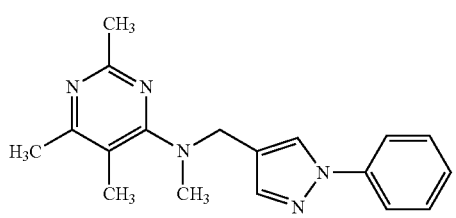

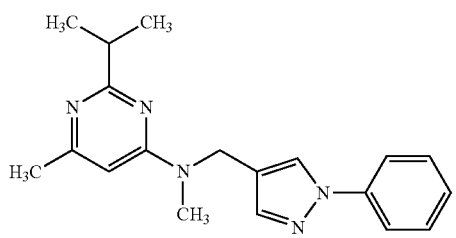

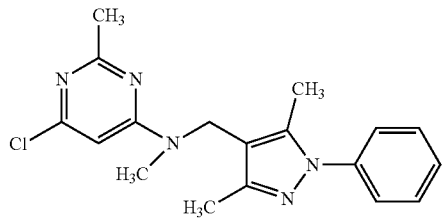

However, the substituted pyrimidine compound having the structure shown by the general formula I of the present invention had not been reported.

SUMMARY

The purpose of the present invention is to provide a pyrimidine-containing substituted pyrazole compound capable of controlling various fungi, pests and mites, and a preparation method and use thereof for preparing medicine for controlling fungi, pests and mites in agriculture or other fields.

To achieve the above purpose, the present invention adopts the following technical solution:

The present invention provides a substituted pyrimidine compound. The substituted pyrimidine compound is a compound shown by general formula I:

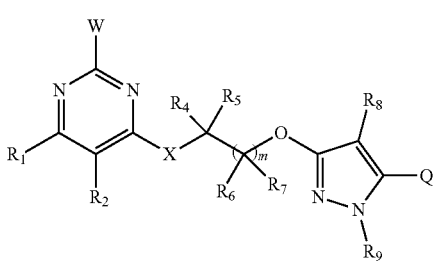

in the formula:

$R_1$ is selected from hydrogen, halogen, cyano, nitro, amino, carboxyl, $C_1$-$C_{12}$ alkyl, halogenated $C_1$-$C_{12}$ alkyl, $C_3$-$C_{12}$ cycloalkyl, $C_1$-$C_{12}$ alkoxy, halogenated $C_1$-$C_{12}$ alkoxy, $C_1$-$C_{12}$ alkylthio, halogenated $C_1$-$C_{12}$ alkylthio, $C_1$-$C_{12}$ alkylsulfinyl, $C_1$-$C_{12}$ alkylsulfonyl, $C_2$-$C_{12}$ alkenyl, halogenated $C_2$-$C_{12}$ alkenyl, $C_2$-$C_{12}$ alkynyl, halogenated $C_2$-$C_{12}$ alkynyl, $C_3$-$C_{12}$ alkenyloxy, halogenated $C_3$-$C_{12}$ alkenyloxy, $C_3$-$C_{12}$ alkynyloxy, halogenated $C_3$-$C_{12}$ alkynyloxy, $C_1$-$C_{12}$ alkylamino, di($C_1$-$C_{12}$ alkyl)amino, $C_1$-$C_{12}$ alkylaminocarbonyl, halogenated $C_1$-$C_{12}$ alkylaminocarbonyl, $C_1$-$C_{12}$ alkoxycarbonyl, halogenated $C_1$-$C_{12}$ alkoxycarbonyl, $C_1$-$C_{12}$ alkoxy $C_1$-$C_{12}$ alkyl or $C_1$-$C_{12}$ alkylthio $C_1$-$C_{12}$ alkyl;

$R_2$ is selected from hydrogen, halogen, cyano, nitro, amino, carboxyl, formyl, $C_1$-$C_{12}$ alkyl, halogenated $C_1$-$C_{12}$ alkyl, $C_1$-$C_{12}$ alkoxy or halogenated $C_1$-$C_{12}$ alkoxy;

$R_1$ and $R_2$ can also form a five-membered ring, six-membered ring, seven-membered ring or eight-membered ring containing C, N, O or S together with a connected pyrimidine ring;

X is selected from $NR_3$, O or S;

$R_3$ is selected from hydrogen, hydroxyl, formyl, $C_1$-$C_{12}$ alkyl, halogenated $C_1$-$C_{12}$ alkyl, $C_1$-$C_{12}$ alkoxyl, halogenated $C_1$-$C_{12}$ alkoxyl, $C_3$-$C_{12}$ cycloalkyl, $C_1$-$C_{12}$ alkylthio, $C_2$-$C_{12}$ alkenylthio, $C_2$-$C_{12}$ alkenyl, $C_2$-$C_{12}$ alkynyl, halogenated $C_2$-$C_{12}$ alkenyl, halogenated $C_2$-$C_{12}$ alkynyl, $C_1$-$C_{12}$ alkoxy $C_1$-$C_{12}$ alkyl, halogenated $C_1$-$C_{12}$ alkoxy $C_1$-$C_{12}$ alkyl, $C_1$-$C_{12}$ alkylthio $C_1$-$C_{12}$ alkyl, halogenated $C_1$-$C_{12}$ alkylthio $C_1$-$C_{12}$ alkyl, $C_1$-$C_{12}$ alkylsulfinyl, halogenated $C_1$-$C_{12}$ alkylsulfinyl, $C_1$-$C_{12}$ alkylsulfonyl, halogenated $C_1$-$C_{12}$ alkylsulfonyl, $C_1$-$C_{12}$ alkylaminosulfonyl, di($C_1$-$C_{12}$ alkyl) aminosulfonyl, $C_1$-$C_{12}$ alkylsulfonylaminocarbonyl, $C_1$-$C_{12}$ alkylcarbonylaminosulfonyl, $C_3$-$C_{12}$ cycloalkyloxycarbonyl, $C_1$-$C_{12}$ alkylcarbonyl, halogenated $C_1$-$C_{12}$ alkylcarbonyl, $C_1$-$C_{12}$ alkoxycarbonyl, halogenated $C_1$-$C_{12}$ alkoxycarbonyl, $C_1$-$C_{12}$ alkylcarbonyl $C_1$-$C_{12}$ alkyl, $C_1$-$C_{12}$ alkoxycarbonyl $C_1$-$C_{12}$ alkyl, $C_1$-$C_{12}$ alkylaminocarbonyl, di($C_1$-$C_{12}$ alkyl)aminocarbonyl, $C_2$-$C_{12}$ alkenyloxycarbonyl, $C_2$-$C_{12}$ alkynyloxycarbonyl, $C_1$-$C_{12}$ alkoxy $C_1$-$C_{12}$ alkoxycarbonyl, $C_1$-$C_{12}$ alkylaminothio, di($C_1$-$C_{12}$ alkyl) aminothio, and unsubstituted or substituted arylcarbonyl $C_1$-$C_6$ alkyl, arylcarbonyl, aryloxycarbonyl, aryl $C_1$-$C_6$ alkyloxycarbonyl, aryl $C_1$-$C_6$ alkyl, heteroarylcarbonyl $C_1$-$C_6$ alkyl, heteroarylcarbonyl, heteroaryloxycarbonyl, heteroaryl $C_1$-$C_6$ alkyloxycarbonyl and heteroaryl $C_1$-$C_6$ alkyl by 1-5 of the following groups, the following groups are halogen, nitro, cyano, $C_1$-$C_6$ alkyl, halogenated $C_1$-$C_6$ alkyl, $C_1$-$C_6$ alkoxy or halogenated $C_1$-$C_6$ alkoxy;

$R_4$ and $R_5$ are the same or different, and are respectively selected from hydrogen, halogen, $C_1$-$C_{12}$ alkyl, halogenated $C_1$-$C_{12}$ alkyl, $C_1$-$C_{12}$ alkoxyl or halogenated $C_1$-$C_{12}$ alkoxyl, wherein $R_4$ and $R_5$ can also form a $C_3$-$C_8$ ring together with the connected C;

$R_6$ and $R_7$ are the same or different, and are respectively selected from hydrogen, halogen, $C_1$-$C_{12}$ alkyl, halogenated $C_1$-$C_{12}$ alkyl, $C_1$-$C_{12}$ alkoxyl or halogenated $C_1$-$C_{12}$ alkoxyl, wherein $R_6$ and $R_7$ can also form a $C_3$-$C_8$ ring together with the connected C;

m is selected from an integer from 0 to 5;

$R_8$ is selected from hydrogen, cyano, halogen, $C_1$-$C_{12}$ alkyl, halogenated $C_1$-$C_{12}$ alkyl, $C_1$-$C_{12}$ alkoxycarbonyl, halogenated $C_1$-$C_{12}$ alkoxycarbonyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

$R_9$ is selected from hydrogen, $C_1$-$C_{12}$ alkyl, $C_3$-$C_8$ cycloalkyl, halogenated $C_1$-$C_{12}$ alkyl, $C_1$-$C_{12}$ alkylcarbonyl, halogenated $C_1$-$C_{12}$ alkylcarbonyl, $C_1$-$C_{12}$ alkylsulfonyl, halogenated $C_1$-$C_{12}$ alkylsulfonyl, $C_1$-$C_{12}$ alkoxycarbonyl, $C_1$-$C_{12}$ alkoxy $C_1$-$C_{12}$ alkyl, $C_1$-$C_{12}$ alkoxycarbonyl $C_1$-$C_{12}$ alkyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

$R_{10}$ is selected from halogen, hydroxyl, amino, cyano, nitro, $C_1$-$C_{12}$ alkyl, halogenated $C_1$-$C_{12}$ alkyl, $C_1$-$C_{12}$ alkoxy, halogenated $C_1$-$C_{12}$ alkoxy, $C_1$-$C_{12}$ cycloalkyl, $C_1$-$C_{12}$ alkylamino, halogenated $C_1$-$C_{12}$ alkylamino, di($C_1$-$C_{12}$ alkyl)amino, halogenated di($C_1$-$C_{12}$ alkyl)amino, C(=O)$NR_{11}R_{12}$, $C_1$-$C_{12}$ alkylthio, halogenated $C_1$-$C_{12}$ alkylthio, $C_2$-$C_{12}$ alkenyl, $C_2$-$C_{12}$ alkynyl, $C_2$-$C_{12}$ alkenyloxy, halogenated $C_2$-$C_{12}$ alkenyloxy, $C_2$-$C_{12}$ alkynyloxy, halogenated $C_2$-$C_{12}$ alkynyloxy, $C_1$-$C_{12}$ alkylsulfonyl, halogenated $C_1$-$C_{12}$ alkylsulfonyl, $C_1$-$C_{12}$ alkylcarbonyl, halogenated $C_1$-$C_{12}$ alkylcarbonyl, $C_1$-$C_{12}$ alkoxycarbonyl, halogenated $C_1$-$C_{12}$ alkoxycarbonyl, $C_1$-$C_{12}$ alkoxy $C_1$-$C_{12}$ alkyl, halogenated $C_1$-$C_{12}$ alkoxy $C_1$-$C_{12}$ alkyl, $C_1$-$C_{12}$ alkylthio $C_1$-$C_{12}$ alkyl, halogenated $C_1$-$C_{12}$ alkylthio $C_1$-$C_{12}$ alkyl, $C_1$-$C_{12}$ alkoxycarbonyl $C_1$-$C_{12}$ alkyl, halogenated $C_1$-$C_{12}$ alkoxycarbonyl $C_1$-$C_{12}$ alkyl, $C_1$-$C_{12}$ alkylthiocarbonyl $C_1$-$C_{12}$ alkyl, halogenated $C_1$-$C_{12}$ alkylthiocarbonyl $C_1$-$C_{12}$ alkyl, $C_1$-$C_{12}$ alkylcarbonyloxy, halogenated $C_1$-$C_{12}$ alkylcarbonyloxy, $C_1$-$C_{12}$ alkoxycarbonyloxy, halogenated $C_1$-$C_{12}$ alkoxycarbonyloxy, $C_1$-$C_{12}$ alkylsulfonyloxy, halogenated $C_1$-$C_{12}$ alkylsulfonyloxy, $C_1$-$C_{12}$ alkoxy $C_1$-$C_{12}$ alkoxyl or halogenated $C_1$-$C_{12}$ alkoxy $C_1$-$C_{12}$ alkoxyl;

$R_{11}$ and $R_{12}$ are the same or different, and are respectively selected from hydrogen, $C_1$-$C_{12}$ alkyl or halogenated $C_1$-$C_{12}$ alkyl;

W is selected from hydrogen, halogen, $C_1$-$C_{12}$ alkyl, halogenated $C_1$-$C_{12}$ alkyl, $C_3$-$C_8$ cycloalkyl, $C_1$-$C_{12}$ alkoxyl, $C_1$-$C_{12}$ alkylthio or $C_1$-$C_{12}$ alkylsulfonyl;

Q is selected from unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

or salt of the compound shown by the general formula I.

In the substituted pyrimidine compound of the present invention, an optional compound comprises: in the general formula I:

$R_1$ is selected from hydrogen, halogen, cyano, nitro, amino, carboxyl, $C_1$-$C_6$ alkyl, halogenated $C_1$-$C_6$ alkyl, $C_3$-$C_6$ cycloalkyl, $C_1$-$C_6$ alkoxy, halogenated $C_1$-$C_6$ alkoxyl, $C_1$-$C_6$ alkylthio, $C_1$-$C_6$ alkylsulfinyl, $C_1$-$C_6$ alkylsulfonyl, halogenated $C_1$-$C_6$ alkylthio, $C_2$-$C_6$ alkenyl, halogenated $C_2$-$C_6$ alkenyl, $C_2$-$C_6$ alkynyl, halogenated $C_2$-$C_6$ alkynyl, $C_3$-$C_6$ alkenyloxy, halogenated $C_3$-$C_6$ alkenyloxy, $C_3$-$C_6$ alkynyloxy, halogenated $C_3$-$C_6$ alkynyloxy, $C_1$-$C_6$ Alkylamino, di($C_1$-$C_6$ alkyl) amino, $C_1$-$C_6$ alkylaminocarbonyl, halogenated $C_1$-$C_6$ alkylaminocarbonyl, $C_1$-$C_6$ alkoxycarbonyl, halogenated $C_1$-$C_6$ alkoxycarbonyl, $C_1$-$C_6$ alkoxy $C_1$-$C_6$ alkyl or $C_1$-$C_6$ alkylthio $C_1$-$C_6$ alkyl;

$R_2$ is selected from hydrogen, halogen, cyano, nitro, amino, carboxyl, formyl, $C_1$-$C_6$ alkyl, halogenated $C_1$-$C_6$ alkyl, $C_1$-$C_6$ alkoxy or halogenated $C_1$-$C_6$ alkoxy;

$R_1$ and $R_2$ can also form a five-membered ring or six-membered ring containing C, N, O or S together with a connected pyrimidine ring;

X is selected from $NR_3$, O or S;

$R_3$ is selected from hydrogen, hydroxyl, formyl, $C_1$-$C_6$ alkyl, halogenated $C_1$-$C_6$ alkyl, $C_1$-$C_6$ alkoxy, halogenated $C_1$-$C_6$ alkoxyl, $C_3$-$C_6$ cycloalkyl, $C_1$-$C_6$ alkylthio, $C_2$-$C_6$ alkenylthio, $C_2$-$C_6$ alkenyl, $C_2$-$C_6$ alkynyl, halogenated $C_2$-$C_6$ alkenyl, halogenated $C_2$-$C_6$ alkynyl, $C_1$-$C_6$ alkoxy $C_1$-$C_6$ alkyl, halogenated $C_1$-$C_6$ alkoxy $C_1$-$C_6$ alkyl, $C_1$-$C_6$ alkylthio $C_1$-$C_6$ alkyl, halogenated $C_1$-$C_6$ alkylthio $C_1$-$C_6$ alkyl, $C_1$-$C_6$ alkylsulfinyl, halogenated $C_1$-$C_6$ alkylsulfinyl, $C_1$-$C_6$ alkylsulfonyl, halogenated $C_1$-$C_6$ alkylsulfonyl, $C_1$-$C_6$ alkylaminosulfonyl, di($C_1$-$C_6$ alkyl) aminosulfonyl, $C_1$-$C_6$ alkylsulfonylaminocarbonyl, $C_1$-$C_6$ alkylcarbonylaminosulfonyl, $C_2$-$C_6$ cycloalkyloxycarbonyl, $C_1$-$C_6$ alkylcarbonyl, halogenated $C_1$-$C_6$ alkylcarbonyl, $C_1$-$C_6$ alkoxycarbonyl, halogenated $C_1$-$C_6$ alkoxycarbonyl, $C_1$-$C_6$ alkylcarbonyl $C_1$-$C_6$ alkyl, $C_1$-$C_6$ alkoxycarbonyl $C_1$-$C_6$ alkyl, $C_1$-$C_6$ alkylaminocarbonyl, di($C_1$-$C_6$ alkyl) aminocarbonyl, $C_2$-$C_6$ alkenyloxycarbonyl, $C_2$-$C_6$ alkynyloxycarbonyl, $C_1$-$C_6$ alkoxy $C_1$-$C_6$ alkoxycarbonyl, $C_1$-$C_6$ alkylaminothio, di($C_1$-$C_6$ alkyl) aminothio, and unsubstituted or substituted arylcarbonyl $C_1$-$C_6$ alkyl, arylcarbonyl, aryloxycarbonyl, aryl $C_1$-$C_6$ alkyloxycarbonyl, aryl $C_1$-$C_6$ alkyl, heteroarylcarbonyl $C_1$-$C_6$ alkyl, heteroarylcarbonyl, heteroaryloxycarbonyl, heteroaryl $C_1$-$C_6$ alkyloxycarbonyl and heteroaryl $C_1$-$C_6$ alkyl by 1-5 of the following groups, the following groups are halogen, nitro, cyano, $C_1$-$C_6$ alkyl, halogenated $C_1$-$C_6$ alkyl, $C_1$-$C_6$ alkoxy or halogenated $C_1$-$C_6$ alkoxy;

$R_4$ and $R_5$ are the same or different, and are respectively selected from hydrogen, halogen, $C_1$-$C_6$ alkyl, halogenated $C_1$-$C_6$ alkyl, $C_1$-$C_6$ alkoxy or halogenated $C_1$-$C_6$ alkoxy;

wherein $R_4$ and $R_5$ can also form a $C_3$-$C_6$ ring together with the connected C;

$R_6$ and $R_7$ are the same or different, and are respectively selected from hydrogen, halogen, $C_1$-$C_6$ alkyl, halogenated $C_1$-$C_6$ alkyl, $C_1$-$C_6$ alkoxyl or halogenated $C_1$-$C_6$ alkoxyl;

wherein $R_6$ and $R_7$ can also form a $C_3$-$C_6$ ring together with the connected C;

m is selected from an integer from 0 to 4;

$R_8$ is selected from hydrogen, cyano, halogen, $C_1$-$C_6$ alkyl, halogenated $C_1$-$C_6$ alkyl, $C_1$-$C_6$ alkoxycarbonyl, halogenated $C_1$-$C_6$ alkoxycarbonyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

$R_9$ is selected from hydrogen, $C_1$-$C_6$ alkyl, $C_3$-$C_6$ cycloalkyl, halogenated $C_1$-$C_6$ alkyl, $C_1$-$C_6$ alkylcarbonyl, halogenated Q-$C_6$ alkylcarbonyl, $C_1$-$C_6$ alkylsulfonyl, halogenated $C_1$-$C_6$ alkylsulfonyl, $C_1$-$C_6$ alkoxycarbonyl, $C_1$-$C_6$ alkoxy $C_1$-$C_6$ alkyl, $C_1$-$C_6$ alkoxycarbonyl $C_1$-$C_6$ alkyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

$R_{10}$ is selected from halogen, hydroxyl, amino, cyano, nitro, $C_1$-$C_6$ alkyl, halogenated $C_1$-$C_6$ alkyl, $C_1$-$C_6$ alkoxyl, halogenated $C_1$-$C_6$ alkoxy, $C_3$-$C_6$ cycloalkyl, $C_1$-$C_6$ alkylamino, halogenated $C_1$-$C_6$ alkylamino, di($C_1$-$C_6$ alkyl) amino, halogenated di($C_1$-$C_6$ alkyl) amino, C(=O)NR$_{11}$R$_{12}$, $C_1$-$C_6$ alkylthio, halogenated $C_1$-$C_6$ alkylthio, $C_2$-$C_6$ alkenyl, $C_2$-$C_6$ alkynyl, $C_2$-$C_6$ alkenyloxy, halogenated $C_2$-$C_6$ alkenyloxy, $C_2$-$C_6$ alkynyloxy, halogenated $C_2$-$C_6$ alkynyloxy, $C_1$-$C_6$ alkylsulfonyl, halogenated $C_1$-$C_6$ alkylsulfonyl, $C_1$-$C_6$ alkylcarbonyl, halogenated $C_1$-$C_6$ alkylcarbonyl, $C_1$-$C_6$ alkoxycarbonyl, halogenated $C_1$-$C_6$ alkoxycarbonyl, $C_1$-$C_6$ alkoxy $C_1$-$C_6$ alkyl, halogenated $C_1$-$C_6$ alkoxy $C_1$-$C_6$ alkyl, $C_1$-$C_6$ alkylthio $C_1$-$C_6$ alkyl, halogenated $C_1$-$C_6$ alkylthio $C_1$-$C_6$ alkyl, $C_1$-$C_6$ alkoxycarbonyl $C_1$-$C_6$ alkyl, halogenated $C_1$-$C_6$ alkoxycarbonyl $C_1$-$C_6$ alkyl, $C_1$-$C_6$ alkylthiocarbonyl $C_1$-$C_6$ alkyl, halogenated $C_1$-$C_6$ alkylthiocarbonyl $C_1$-$C_6$ alkyl, $C_1$-$C_6$ alkylcarbonyloxy, halogenated $C_1$-$C_6$ alkylcarbonyloxy, $C_1$-$C_6$ alkoxycarbonyloxy, halogenated $C_1$-$C_6$ alkoxycarbonyloxy, $C_1$-$C_6$ alkylsulfonyloxy, halogenated $C_1$-$C_6$ alkylsulfonyloxy, $C_1$-$C_6$ alkoxy $C_1$-$C_6$ alkoxy or halogenated $C_1$-$C_6$ alkoxy $C_1$-$C_6$ alkoxy;

$R_{11}$ and $R_{12}$ are the same or different, and are respectively selected from hydrogen, $C_1$-$C_{12}$ alkyl or halogenated $C_1$-$C_{12}$ alkyl;

W is selected from hydrogen, halogen, $C_1$-$C_6$ alkyl, halogenated $C_1$-$C_6$ alkyl, $C_3$-$C_6$ cycloalkyl, $C_1$-$C_6$ alkoxy, $C_1$-$C_6$ alkylthio or $C_1$-$C_6$ alkylsulfonyl;

Q is selected from unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

or salt of the compound shown by the general formula I.

In the substituted pyrimidine compound of the present invention, a relatively optional compound comprises: in the general formula I, Q is selected from aryl unsubstituted or substituted by one to five $R_{10}$; the structural formula of the general formula I of the compound is further shown by I-1:

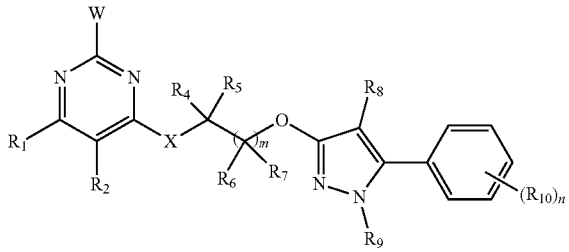

I-1 in the formula, $R_1$ is selected from hydrogen, halogen, cyano, nitro, amino, carboxyl, $C_1$-$C_4$ alkyl, halogenated $C_1$-$C_4$ alkyl, $C_3$-$C_4$ cycloalkyl, $C_1$-$C_4$ alkoxyl, halogenated $C_1$-$C_4$ alkoxyl, $C_1$-$C_4$ alkylthio, $C_1$-$C_4$ alkylsulfinyl, $C_1$-$C_4$ alkylsulfonyl, halogenated $C_1$-$C_4$ alkylthio, $C_2$-$C_4$ alkenyl, halogenated $C_2$-$C_4$ alkenyl, $C_2$-$C_4$ alkynyl, halogenated $C_2$-$C_4$ alkynyl, $C_3$-$C_4$ alkenyloxy, halogenated $C_3$-$C_4$ alkenyloxy, $C_3$-$C_4$ alkynyloxy, halogenated $C_3$-$C_4$ alkynyloxy, $C_1$-$C_4$ alkylamino, di($C_1$-$C_4$ alkyl) amino, $C_1$-$C_4$ alkylaminocarbonyl, halogenated $C_1$-$C_4$ alkylaminocarbonyl, $C_1$-$C_4$ alkoxycarbonyl, halogenated $C_1$-$C_4$ alkoxycarbonyl, $C_1$-$C_4$ alkoxy $C_1$-$C_4$ alkyl or $C_1$-$C_4$ alkylthio $C_1$-$C_4$ alkyl;

$R_2$ is selected from hydrogen, halogen, cyano, nitro, amino, carboxyl, formyl, $C_1$-$C_4$ alkyl, halogenated $C_1$-$C_4$ alkyl, $C_1$-$C_4$ alkox, or halogenated $C_1$-$C_4$ alkoxyl;

$R_1$ and $R_2$ can also form a five-membered ring or six-membered ring containing C, N, O or S together with a connected pyrimidine ring;

X is selected from NR$_3$, O or S;

$R_3$ is selected from hydrogen, hydroxyl, formyl, $C_1$-$C_4$ alkyl, halogenated $C_1$-$C_4$ alkyl, $C_1$-$C_4$ alkoxy, halogenated $C_1$-$C_4$ alkoxy, $C_3$-$C_4$ cycloalkyl, $C_1$-$C_4$ alkylthio, $C_2$-$C_4$ alkenylthio, $C_2$-$C_4$ alkenyl, $C_2$-$C_4$ alkynyl, halogenated $C_2$-$C_4$ alkenyl, halogenated $C_2$-$C_4$ alkynyl, $C_1$-$C_4$ alkoxy $C_1$-$C_4$ alkyl, halogenated $C_1$-$C_4$ alkoxy $C_1$-$C_4$ alkyl, $C_1$-$C_4$ alkylthio $C_1$-$C_4$ alkyl, halogenated $C_1$-$C_4$ alkylthio $C_1$-$C_4$ alkyl, $C_1$-$C_4$ alkylsulfinyl, halogenated $C_1$-$C_4$ alkylsulfinyl, $C_1$-$C_4$ alkylsulfonyl, halogenated $C_1$-$C_4$ alkylsulfonyl, $C_1$-$C_4$ alkylaminosulfonyl, di($C_1$-$C_4$ alkyl) aminosulfonyl, $C_1$-$C_4$ alkylsulfonylaminocarbonyl, $C_1$-$C_4$ alkylcarbonylaminosulfonyl, $C_3$-$C_4$ cycloalkyloxycarbonyl, $C_1$-$C_4$ alkylcarbonyl, halogenated $C_1$-$C_4$ alkylcarbonyl, $C_1$-$C_4$ alkoxycarbonyl, halogenated $C_1$-$C_4$ alkoxycarbonyl, $C_1$-$C_4$ alkylcarbonyl $C_1$-$C_4$ alkyl, $C_1$-$C_4$ alkoxycarbonyl $C_1$-$C_4$ alkyl, $C_1$-$C_4$ alkylaminocarbonyl, di($C_1$-$C_4$ alkyl) aminocarbonyl, $C_2$-$C_4$ alkenyloxycarbonyl, $C_2$-$C_4$ alkynyloxycarbonyl, $C_1$-$C_4$ alkoxy $C_1$-$C_4$ alkoxycarbonyl, $C_1$-$C_4$ alkylaminothio, di($C_1$-$C_4$ alkyl) aminothio, and unsubstituted or substituted arylcarbonyl $C_1$-$C_4$ alkyl, arylcarbonyl, aryloxycarbonyl, aryl $C_1$-$C_4$ alkyloxycarbonyl, aryl $C_1$-$C_4$ alkyl, heteroarylcarbonyl $C_1$-$C_4$ alkyl, heteroarylcarbonyl, heteroaryloxycarbonyl, heteroaryl $C_1$-$C_4$ alkyloxycarbonyl and heteroaryl $C_1$-$C_4$ alkyl by 1-5 of the following groups, the following groups are halogen, nitro, cyano, $C_1$-$C_4$ alkyl, halogenated $C_1$-$C_4$ alkyl, $C_1$-$C_4$ alkoxy or halogenated $C_1$-$C_6$ alkoxy;

$R_4$ and $R_5$ are the same or different, and are respectively selected from hydrogen, halogen, $C_1$-$C_4$ alkyl, halogenated $C_1$-$C_4$ alkyl, $C_1$-$C_4$ alkoxy or halogenated $C_1$-$C_4$ alkoxy;

wherein $R_4$ and $R_5$ can also form a $C_3$-$C_4$ ring together with the connected C;

$R_6$ and $R_7$ are the same or different, and are respectively selected from hydrogen, halogen, $C_1$-$C_4$ alkyl, halogenated $C_1$-$C_4$ alkyl, $C_1$-$C_4$ alkoxyl or halogenated $C_1$-$C_4$ alkoxyl;

wherein $R_6$ and $R_7$ can also form a $C_3$-$C_4$ ring together with the connected C;

m is selected from an integer from 0 to 3;

$R_8$ is selected from hydrogen, cyano, halogen, $C_1$-$C_4$ alkyl, halogenated $C_1$-$C_4$ alkyl, $C_1$-$C_4$ alkoxycarbonyl, halogenated $C_1$-$C_4$ alkoxycarbonyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

$R_9$ is selected from hydrogen, $C_1$-$C_4$ alkyl, $C_3$-$C_4$ cycloalkyl, halogenated $C_1$-$C_4$ alkyl, $C_1$-$C_4$ alkylcarbonyl, halogenated $C_1$-$C_4$ alkylcarbonyl, $C_1$-$C_4$ alkylsulfonyl, halogenated $C_1$-$C_4$ alkylsulfonyl, $C_1$-$C_4$ alkoxycarbonyl, $C_1$-$C_4$ alkoxy $C_1$-$C_4$ alkyl, $C_1$-$C_4$ alkoxycarbonyl $C_1$-$C_4$ alkyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

$R_{10}$ is selected from halogen, hydroxyl, amino, cyano, nitro, $C_1$-$C_4$ alkyl, halogenated $C_1$-$C_4$ alkyl, $C_1$-$C_4$ alkoxyl, halogenated $C_1$-$C_4$ alkoxy, $C_3$-$C_4$ cycloalkyl, $C_1$-$C_4$ alkylamino, halogenated $C_1$-$C_4$ alkylamino, di($C_1$-$C_4$ alkyl) amino, halogenated di($C_1$-$C_4$ alkyl) amino, C(=O)$NR_{12}R_{13}$, $C_1$-$C_4$ alkylthio, halogenated $C_1$-$C_4$ alkylthio, $C_2$-$C_4$ alkenyl, $C_2$-$C_4$ alkynyl, $C_2$-$C_4$ alkenyloxy, halogenated $C_2$-$C_4$ alkenyloxy, $C_2$-$C_4$ alkynyloxy, halogenated $C_2$-$C_4$ alkynyloxy, $C_1$-$C_4$ alkylsulfonyl, halogenated $C_1$-$C_4$ alkylsulfonyl, $C_1$-$C_4$ alkylcarbonyl, halogenated $C_1$-$C_4$ alkylcarbonyl, $C_1$-$C_4$ alkoxycarbonyl, halogenated $C_1$-$C_4$ alkoxycarbonyl, $C_1$-$C_4$ alkoxy $C_1$-$C_4$ alkyl, halogenated $C_1$-$C_4$ alkoxy $C_1$-$C_4$ alkyl, $C_1$-$C_4$ alkylthio $C_1$-$C_4$ alkyl, halogenated $C_1$-$C_4$ alkylthio $C_1$-$C_4$ alkyl, $C_1$-$C_4$ alkoxycarbonyl $C_1$-$C_4$ alkyl, halogenated $C_1$-$C_4$ alkoxycarbonyl $C_1$-$C_4$ alkyl, $C_1$-$C_4$ alkylthiocarbonyl $C_1$-$C_4$ alkyl, halogenated $C_1$-$C_4$ alkylthiocarbonyl $C_1$-$C_4$ alkyl, $C_1$-$C_4$ alkylcarbonyloxy, halogenated $C_1$-$C_4$ alkylcarbonyloxy, $C_1$-$C_4$ alkoxycarbonyloxy, halogenated $C_1$-$C_4$ alkoxycarbonyloxy, $C_1$-$C_4$ alkylsulfonyloxy, halogenated $C_1$-$C_4$ alkylsulfonyloxy, $C_1$-$C_4$ alkoxy $C_1$-$C_4$ alkoxy or halogenated $C_1$-$C_4$ alkoxy $C_1$-$C_4$ alkoxy;

$R_{11}$ and $R_{12}$ are the same or different, and are respectively selected from hydrogen, $C_1$-$C_{12}$ alkyl or halogenated $C_1$-$C_{12}$ alkyl;

W is selected from hydrogen, halogen, $C_1$-$C_4$ alkyl, halogenated $C_1$-$C_4$ alkyl, $C_3$-$C_4$ cycloalkyl, $C_1$-$C_4$ alkoxy, $C_1$-$C_4$ alkylthio or $C_1$-$C_4$ alkylsulfonyl;

or salt formed by the compound shown by general formula I-1 and hydrochloric acid, sulfuric acid, phosphoric acid, formic acid, acetic acid, trifluoroacetic acid, oxalic acid, methanesulfonic acid, p-toluenesulfonic acid, benzoic acid, phthalic acid, maleic acid, fumaric acid, sorbic acid, malic acid or citric acid.

In the substituted pyrimidine compound of the present invention, a further optional compound comprises: the structure of the compound shown by the general formula I-1 is: I-1A, I-1B, I-1C and I-1D;

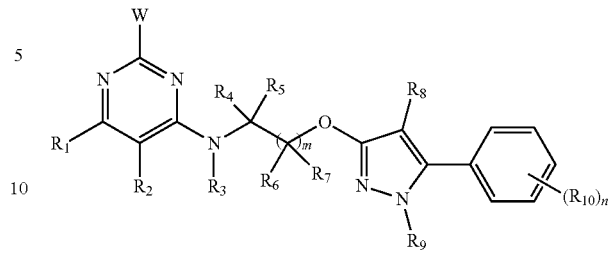
I-1A

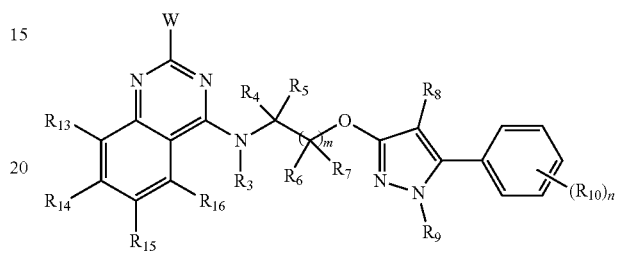
I-1B

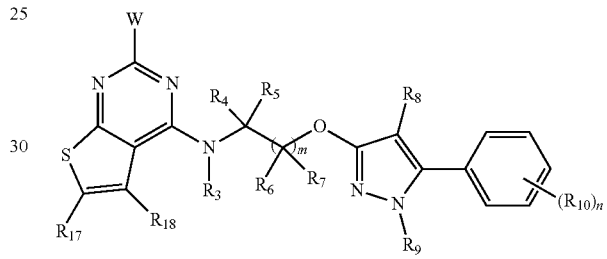
I-1C

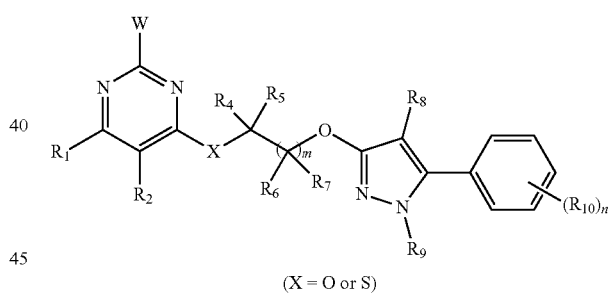
I-1D (X = O or S)

in the formula:

$R_4$ and $R_5$ are the same or different, and are respectively selected from hydrogen, halogen, $C_1$-$C_4$ alkyl, halogenated $C_1$-$C_4$ alkyl, $C_1$-$C_4$ alkoxyl or halogenated $C_1$-$C_4$ alkoxyl;

wherein $R_4$ and $R_5$ can also form a $C_3$-$C_4$ ring together with the connected C;

$R_6$ and $R_7$ are the same or different, and are respectively selected from hydrogen, halogen, $C_1$-$C_4$ alkyl, halogenated $C_1$-$C_4$ alkyl, $C_1$-$C_4$ alkoxyl or halogenated $C_1$-$C_4$ alkoxyl;

wherein $R_6$ and $R_7$ can also form a $C_3$-$C_4$ ring together with the connected C;

m is selected from an integer from 0 to 3;

$R_8$ and $R_9$ are the same or different, and are respectively selected from hydrogen, cyano, halogen, $C_1$-$C_4$ alkyl, halogenated $C_1$-$C_4$ alkyl, $C_1$-$C_4$ alkoxycarbonyl, halogenated $C_1$-$C_4$ alkoxycarbonyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

$R_{10}$ is selected from halogen, hydroxyl, amino, cyano, nitro, $C_1$-$C_4$ alkyl, halogenated $C_1$-$C_4$ alkyl, $C_1$-$C_4$ alkoxyl, halogenated $C_1$-$C_4$ alkoxy, $C_3$-$C_4$ cycloalkyl, $C_1$-$C_4$ alkylamino, halogenated $C_1$-$C_4$ alkylamino, di($C_1$-$C_4$ alkyl) amino, halogenated di($C_1$-$C_4$ alkyl) amino, C(=O)$NR_{11}R_{12}$, $C_1$-$C_4$ alkylthio, halogenated $C_1$-$C_4$ alkylthio, $C_2$-$C_4$ alkenyl, $C_2$-$C_4$ alkynyl, $C_2$-$C_4$ alkenyloxy, halogenated $C_1$-$C_4$ alkenyloxy, $C_1$-$C_4$ alkynyloxy, halogenated $C_2$-$C_4$ alkynyloxy, $C_1$-$C_4$ alkylsulfonyl, halogenated $C_1$-$C_4$ alkylsulfonyl, $C_1$-$C_4$ alkylcarbonyl, halogenated $C_1$-$C_4$ alkylcarbonyl, $C_1$-$C_4$ alkoxycarbonyl, halogenated $C_1$-$C_4$ alkoxycarbonyl, $C_1$-$C_4$ alkoxy $C_1$-$C_4$ alkyl, halogenated $C_1$-$C_4$ alkoxy $C_1$-$C_4$ alkyl, $C_1$-$C_4$ alkylthio $C_1$-$C_4$ alkyl, halogenated $C_1$-$C_4$ alkylthio $C_1$-$C_4$ alkyl, $C_1$-$C_4$ alkoxycarbonyl $C_1$-$C_4$ alkyl, halogenated $C_1$-$C_4$ alkoxycarbonyl $C_1$-$C_4$ alkyl, $C_1$-$C_4$ alkylthiocarbonyl $C_1$-$C_4$ alkyl, halogenated $C_1$-$C_4$ alkylthiocarbonyl $C_1$-$C_4$ alkyl, $C_1$-$C_4$ alkylcarbonyloxy, halogenated $C_1$-$C_4$ alkylcarbonyloxy, $C_1$-$C_4$ alkoxycarbonyloxy, halogenated $C_1$-$C_4$ alkoxycarbonyloxy, $C_1$-$C_4$ alkylsulfonyloxy, halogenated $C_1$-$C_4$ alkylsulfonyloxy, $C_1$-$C_4$ alkoxy $C_1$-$C_4$ alkoxy or halogenated $C_1$-$C_4$ alkoxy $C_1$-$C_4$ alkoxy;

n is selected from an integer from 0 to 5; when n is 0, a benzene ring has no substituent; when n is greater than 1, $R_{10}$ is the same or different;

$R_{11}$ and $R_{12}$ are the same or different and are respectively selected from hydrogen, $C_1$-$C_4$ alkyl or halogenated $C_1$-$C_4$ alkyl;

W is selected from hydrogen, halogen, $C_1$-$C_4$ alkyl, halogenated $C_1$-$C_4$ alkyl, $C_3$-$C_4$ cycloalkyl, $C_1$-$C_4$ alkoxy, $C_1$-$C_4$ alkylthio or $C_1$-$C_4$ alkylsulfonyl;

moreover, when the compound has the general formula I-1D, X is O or S;

when the compounds have the general formulas I-1A and I-1D, $R_1$ is selected from hydrogen, halogen, cyano, nitro, amino, carboxyl, $C_1$-$C_4$ alkyl, halogenated $C_1$-$C_4$ alkyl, $C_3$-$C_4$ cycloalkyl, $C_1$-$C_4$ alkoxyl, halogenated $C_1$-$C_4$ alkoxyl, $C_1$-$C_4$ alkylthio, halogenated $C_1$-$C_4$ alkylthio, $C_1$-$C_4$ alkylsulfinyl, $C_1$-$C_4$ alkylsulfonyl, $C_2$-$C_4$ alkenyl, halogenated $C_2$-$C_4$ alkenyl, $C_2$-$C_4$ alkynyl, halogenated $C_2$-$C_4$ alkynyl, $C_3$-$C_4$ alkenyloxy, halogenated $C_3$-$C_4$ alkenyloxy, $C_1$-$C_4$ alkynyloxy, halogenated $C_3$-$C_4$ alkynyloxy, $C_1$-$C_4$ alkylamino, di($C_1$-$C_4$ alkyl) amino, $C_1$-$C_4$ alkylaminocarbonyl, halogenated $C_1$-$C_4$ alkylaminocarbonyl, $C_1$-$C_4$ alkoxycarbonyl, halogenated $C_1$-$C_4$ alkoxycarbonyl, $C_1$-$C_4$ alkoxy $C_1$-$C_4$ alkyl or $C_1$-$C_4$ alkylthio $C_1$-$C_4$ alkyl;

$R_2$ is selected from hydrogen, halogen, cyano, nitro, amino, carboxyl, formyl, $C_1$-$C_4$ alkyl, halogenated $C_1$-$C_4$ alkyl, $C_1$-$C_4$ alkoxy or halogenated $C_1$-$C_4$ alkoxy;

when the compounds have the general formulas I-1A, I-1B and I-1C, $R_3$ is selected from hydrogen, hydroxyl, formyl, $C_1$-$C_4$ alkyl, halogenated $C_1$-$C_4$ alkyl, $C_1$-$C_4$ alkoxy, halogenated $C_1$-$C_4$ alkoxy, $C_3$-$C_4$ cycloalkyl, $C_1$-$C_4$ alkylthio, $C_2$-$C_4$ alkenylthio, $C_2$-$C_4$ alkenyl, $C_2$-$C_4$ alkynyl, halogenated $C_2$-$C_4$ alkenyl, halogenated $C_2$-$C_4$ alkynyl, $C_1$-$C_4$ alkoxy $C_1$-$C_4$ alkyl, halogenated $C_1$-$C_4$ alkoxy $C_1$-$C_4$ alkyl, $C_1$-$C_4$ alkylthio $C_1$-$C_4$ alkyl, halogenated $C_1$-$C_4$ alkylthio $C_1$-$C_4$ alkyl, $C_1$-$C_4$ alkylsulfinyl, halogenated $C_1$-$C_4$ alkylsulfinyl, $C_1$-$C_4$ alkylsulfonyl, halogenated $C_1$-$C_4$ alkylsulfonyl, $C_1$-$C_4$ alkylaminosulfonyl, di($C_1$-$C_4$ alkyl) aminosulfonyl, $C_1$-$C_4$ alkylsulfonylaminocarbonyl, $C_1$-$C_4$ alkylcarbonylaminosulfonyl, $C_3$-$C_4$ cycloalkyloxycarbonyl, $C_1$-$C_4$ alkylcarbonyl, halogenated $C_1$-$C_4$ alkylcarbonyl, $C_1$-$C_4$ alkoxycarbonyl, halogenated $C_1$-$C_4$ alkoxycarbonyl, $C_1$-$C_4$ alkylcarbonyl $C_1$-$C_4$ alkyl, $C_1$-$C_4$ alkoxycarbonyl $C_1$-$C_4$ alkyl, $C_1$-$C_4$ alkylaminocarbonyl, di($C_1$-$C_4$ alkyl) aminocarbonyl, $C_2$-$C_4$ alkenyloxycarbonyl, $C_2$-$C_4$ alkynyloxycarbonyl, $C_1$-$C_4$ alkoxy $C_1$-$C_4$ alkoxycarbonyl, $C_1$-$C_4$ alkylaminothio, di($C_1$-$C_4$ alkyl) aminothio, and unsubstituted or substituted arylcarbonyl $C_1$-$C_4$ alkyl, arylcarbonyl, aryloxycarbonyl, aryl $C_1$-$C_4$ alkyloxycarbonyl, aryl $C_1$-$C_4$ alkyl, heteroarylcarbonyl $C_1$-$C_4$ alkyl, heteroarylcarbonyl, heteroaryloxycarbonyl, heteroaryl $C_1$-$C_4$ alkyloxycarbonyl and heteroaryl $C_1$-$C_4$ alkyl by 1-5 of the following groups; the following groups are halogen, nitro, cyano, $C_1$-$C_4$ alkyl, halogenated $C_1$-$C_4$ alkyl, $C_1$-$C_4$ alkoxy or halogenated $C_1$-$C_4$ alkoxy;

when the compound has the general formula I-1B, $R_{13}$, $R_{14}$, $R_{15}$ and $R_{16}$ are the same or different and are respectively selected from hydrogen, halogen, hydroxyl, amino, cyano, nitro, $C_1$-$C_4$ alkyl, halogenated $C_1$-$C_4$ alkyl, $C_1$-$C_4$ alkoxy, halogenated $C_1$-$C_4$ alkoxy or $C_3$-$C_4$ cycloalkyl;

when the compound has the general formula I-1C, $R_{17}$ and $R_{18}$ are the same or different and are selected from hydrogen, halogen, $C_1$-$C_4$ alkyl, halogenated $C_1$-$C_4$ alkyl, $C_1$-$C_4$ alkoxyl, halogenated $C_1$-$C_4$ alkoxyl, $C_1$-$C_4$ alkylthio, halogenated $C_1$-$C_4$ alkylthio, $C_3$-$C_4$ cycloalkyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

or salt formed by the compounds shown by general formulas I-1A, I-1B, I-1C and I-1D and hydrochloric acid, sulfuric acid, phosphoric acid, formic acid, acetic acid, trifluoroacetic acid, oxalic acid, methanesulfonic acid, p-toluenesulfonic acid, benzoic acid, phthalic acid, maleic acid, fumaric acid, sorbic acid, malic acid or citric acid.

In the pyrimidine-containing substituted pyrazole compound of the present invention, a more further optional compound comprises: in the compounds shown by the general formulas I-1A, I-1B, I-1C and I-1D:

$R_4$ and $R_5$ are the same or different and are selected from hydrogen, fluorine, chlorine, bromine, iodine, methyl, ethyl, n-propyl, isopropyl, n-butyl, sec-butyl, isobutyl, tert-butyl, methoxyl, ethoxyl, n-propoxy, isopropoxy, n-butoxy, sec-butoxy, isobutoxy or tert-butoxy;

$R_6$ and $R_7$ are the same or different and are respectively selected from hydrogen, fluorine, chlorine, bromine, iodine, methyl, ethyl, n-propyl, isopropyl, n-butyl, sec-butyl, isobutyl, tert-butyl, methoxyl, ethoxyl, n-propoxy, isopropoxy, n-butoxy, sec-butoxy, isobutoxy or tert-butoxy;

$R_8$ and $R_9$ are the same or different and are respectively selected from hydrogen, cyano, fluorine, chlorine, bromine, iodine, methyl, ethyl or trifluoromethyl;

$R_{10}$ is selected from fluorine, chlorine, bromine, iodine, cyano, amino, nitro, methyl, ethyl, n-propyl, isopropyl, n-butyl, sec-butyl, isobutyl, tert-butyl, trifluoromethyl, trichloromethyl, difluoromonochloromethyl, dichloromonofluoromethyl, methoxyl, ethoxyl, n-propoxy, isopropoxy, n-butoxy, sec-butoxy, isobutoxy, t-butoxy, methylthio, ethylthio, trifluoromethoxy, trifluoroethoxy, methoxycarbonyl, ethoxycarbonyl, aminocarbonyl, methylaminocarbonyl, ethylaminocarbonyl or dimethylaminocarbonyl;

n is selected from an integer from 0 to 5; when n is 0, a benzene ring has no substituent; when n is greater than 1, $R_{10}$ may be the same or different;

W is selected from hydrogen, fluorine, chlorine, bromine, iodine, methyl, ethyl, n-propyl, isopropyl, n-butyl, sec-butyl, isobutyl, t-butyl, monofluoromethyl, monochloromethyl, difluoromethyl, trifluoromethyl, trifluoroethyl, methoxyl, ethoxyl, methylthio, ethylthio, methylsulfonyl or ethylsulfonyl;

moreover, when the compound has the general formula I-1D, X is O or S;

when the compounds have the general formulas I-1A and I-1D, $R_1$ is selected from hydrogen, fluorine, chlorine, bromine, iodine, cyano, nitro, amino, carboxyl, methyl, ethyl, n-propyl, isopropyl, n-butyl, sec-butyl, isobutyl, tert-butyl, monofluoromethyl, monochloromethyl, difluoromethyl, trifluoromethyl, trifluoroethyl, methoxymethyl, ethoxymethyl or trifluoroethoxymethyl;

$R_2$ is selected from hydrogen, fluorine, chlorine, bromine, iodine, cyano, nitro, amino, carboxyl, formyl, methyl, ethyl, methoxy, ethoxy or trifluoroethoxy;

when the compounds have the general formulas I-1A, I-1B and I-1C, $R_3$ is selected from hydrogen, hydroxyl, formyl, acetyl, propanoyl, butyryl, trifluoroacetyl, benzoyl, methyl, ethyl, n-propyl, isopropyl, n-butyl, sec-butyl, isobutyl, tert-butyl, trifluoromethyl, trifluoroethyl, methoxyl, ethoxyl, trifluoroethoxy, cyclopropyloxy, methylthio, ethylthio, allyl, propargyl, mesyl, ethylsulfonyl, trifluoroethylsulfonyl, methylaminosulfonyl, ethylaminosulfonyl, dimethylaminosulfonyl, diethylaminosulfonyl, methylsulfonylaminocarbonyl, methoxycarbonyl, ethoxycarbonyl, propoxycarbonyl, isopropoxycarbonyl, methylaminocarbonyl, dimethylaminocarbonyl, vinyloxycarbonyl, ethynyloxycarbonyl, methylaminothio, ethylaminothio or dimethylaminothio;

when the compound has the general formula I-1B, $R_{13}$, $R_{14}$, $R_5$ and $R_{16}$ are the same or different and are respectively selected from hydrogen, fluorine, chlorine, bromine, iodine, amino, cyano, nitro, methyl, ethyl, n-propyl, isopropyl, n-butyl, sec-butyl, isobutyl, tert-butyl, trifluoromethyl, trichloromethyl, difluoromonochloromethyl, dichloromonofluoromethyl, methoxy, ethoxy, n-propoxy, isopropoxy, n-butoxy, sec-butoxy, isobutoxy, t-butoxy, trifluoromethoxy or trifluoroethoxy;

when the compound has the general formula I-1C, $R_{17}$ and $R_{18}$ are the same or different and are respectively selected from hydrogen, fluorine, chlorine, bromine, iodine, methyl, ethyl, n-propyl, isopropyl, n-butyl, sec-butyl, isobutyl, tert-butyl, trifluoromethyl, trichloromethyl, difluoromonochloromethyl, dichloromonofluoromethyl, trifluoroethyl, methoxyl, ethoxyl, n-propoxy, isopropoxy, n-butoxy, sec-butoxy, isobutoxy, tert-butoxy, trifluoromethoxy, trifluoroethoxy, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

or salt formed by the compounds shown by general formulas I-1A, I-1B, I-1C and I-1D and hydrochloric acid, sulfuric acid, phosphoric acid, formic acid, acetic acid, trifluoroacetic acid, oxalic acid, methanesulfonic acid, p-toluenesulfonic acid, benzoic acid, phthalic acid, maleic acid, fumaric acid, sorbic acid, malic acid or citric acid.

In the substituted pyrimidine compound of the present invention, a still further optional compound comprises: in the compounds shown by the general formulas I-1A, I-1B, I-1C and I-1D:

$R_4$ and $R_5$ are the same or different, and are respectively selected from hydrogen, fluorine, chlorine, bromine or methyl;

$R_6$ and $R_7$ are selected from hydrogen;

$R_8$ is hydrogen or methyl;

$R_9$ is selected from hydrogen or methyl;

$R_{10}$ is selected from fluorine, chlorine, bromine, iodine, cyano, nitro, methyl, ethyl, trifluoromethyl, methoxy, methylthio or trifluoromethoxy;

n is selected from an integer from 0 to 5; when n is 0, the benzene ring has no substituent; when n is greater than 1, $R_{10}$ can be the same or different;

W is selected from hydrogen, fluorine, chlorine, bromine, iodine or methyl;

moreover, when the compound has the general formula I-1D, X is O or S;

when the compounds have the general formulas I-1A and I-1D, $R_1$ is selected from hydrogen, fluorine, chlorine, bromine, iodine, methyl, ethyl or difluoromethyl;

$R_2$ is selected from hydrogen, fluorine, chlorine, bromine, iodine, nitro, amino, formyl, methyl, ethyl, methoxy or ethoxy;

when the compounds have the general formulas I-1A, I-1B and I-1C, $R_3$ is selected from hydrogen, methyl, acetyl, trifluoroacetyl, methoxy, methylthio, allyl, methanesulfonyl, methylaminosulfonyl, dimethylaminosulfonyl, methoxycarbonyl, methylaminocarbonyl, dimethylaminocarbonyl, methylaminothio or dimethylaminothio;

when the compound has the general formula I-1B, $R_{13}$, $R_{14}$, $R_{15}$ and $R_{16}$ are the same or different and are respectively selected from hydrogen, fluorine, chlorine, bromine, iodine or methyl;

when the compound has the general formula I-1C, $R_{17}$ and $R_{18}$ are the same or different and are respectively selected from hydrogen, fluorine, chlorine, bromine or iodine;

or salt formed by the compounds shown by general formulas I-1A, I-1B, I-1C and I-1D and hydrochloric acid, sulfuric acid, phosphoric acid, formic acid, acetic acid, trifluoroacetic acid, oxalic acid, methanesulfonic acid, p-toluenesulfonic acid, benzoic acid, phthalic acid, maleic acid, fumaric acid, sorbic acid, malic acid or citric acid.

In the substituted pyrimidine compound of the present invention, a more optional compound comprises: in the compounds shown by the general formulas I-1A, I-1B, I-1C and I-1D:

$R_4$ and $R_5$ can be the same or different, and are respectively selected from hydrogen or methyl;

$R_6$ and $R_7$ are selected from hydrogen;

$R_8$ is hydrogen or methyl;

$R_9$ is selected from methyl;

$R_{10}$ is selected from fluorine, chlorine, bromine, iodine, cyano, nitro, methyl, ethyl, trifluoromethyl, methoxy, methylthio or trifluoromethoxy;

n is selected from an integer from 1 to 5; when n is greater than 1, $R_{10}$ can be the same or different;

W is selected from hydrogen, fluorine, chlorine, bromine or iodine;

moreover, when the compound has the general formula I-1D, X is O or S;

when the compounds have the general formulas I-1A and I-1D, $R_1$ is selected from fluorine, chlorine, bromine, iodine, methyl, ethyl or difluoromethyl;

$R_2$ is selected from fluorine, chlorine, bromine, iodine, nitro, amino, formyl, methyl or methoxyl;

when the compounds have the general formulas I-1A, I-1B and I-1C,

R₃ is selected from hydrogen, methyl, acetyl, methoxyl, allyl, methanesulfonyl, methoxycarbonyl, methylaminocarbonyl, dimethylaminocarbonyl or dimethylaminothio;

when the compound has the general formula I-1B, $R_{13}$, $R_{14}$, $R_{15}$ and $R_{16}$ are selected from hydrogen;

when the compound has the general formula I-1C, $R_{17}$ is selected from hydrogen;

$R_{18}$ is selected from chlorine;

or salt formed by the compounds shown by general formulas I-1A, I-1B, I-1C and I-1D and hydrochloric acid, sulfuric acid, phosphoric acid, formic acid, acetic acid, trifluoroacetic acid, oxalic acid, methanesulfonic acid, p-toluenesulfonic acid, benzoic acid, phthalic acid, maleic acid, fumaric acid, sorbic acid, malic acid or citric acid.

A preparation method of the substituted pyrimidine compound is provided. The preparation method of the compound shown by the general formula I is:

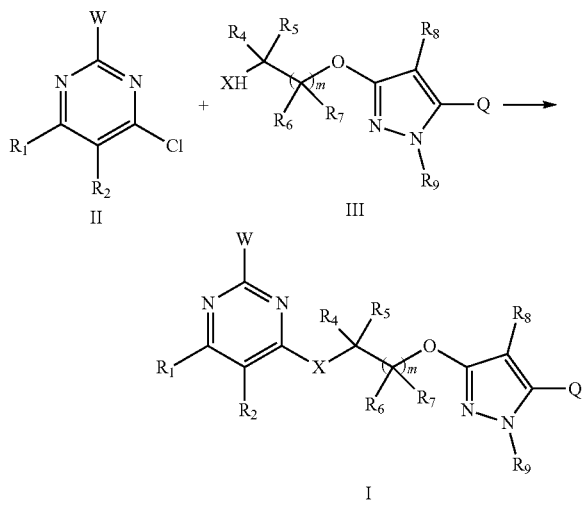

A use of the substituted pyrimidine compound shown by the general formula I as a fungicide, insecticide and acaricide drug is provided. Further, a use of the compound as a fungicide, insecticide and acaricide drug in agriculture or other fields is provided.

A fungicidal, insecticidal and acaricidal composition is provided. The composition uses the substituted pyrimidine compound shown by the general formula I as an active ingredient, wherein the weight percentage of the active ingredient in the composition is 0.1-99%.

In the definitions of the compounds of the general formula I provided above, the terms used in the collection are generally defined as follows:

Halogen: fluorine, chlorine, bromine or iodine. Alkyl: linear or branched alkyl, such as methyl, ethyl, propyl, isopropyl, n-butyl or tert-butyl. Cycloalkyl: substituted or unsubstituted cyclic alkyl, such as cyclopropyl, cyclopentyl or cyclohexyl. Substituents, such as methyl and halogen. Haloalkyl: linear or branched alkyl on which hydrogen atoms can be partially or fully replaced by halogen atoms, such as chloromethyl, dichloromethyl, trichloromethyl, fluoromethyl, difluoromethyl and trifluoromethyl. Alkylsulfinyl: linear or branched alkyl, connected to the structure through sulfinyl (—SO—), such as methylsulfinyl. Halogenated alkylsulfinyl: linear or branched alkylsulfinyl, and hydrogen atoms on the alkyl can be partially or fully replaced by halogen atoms. Halogenated alkylsulfonyl: linear or branched alkylsulfonyl, and hydrogen atoms on the alkyl can be partially or fully replaced by halogen atoms. Alkylaminothio: such as $CH_3NHS$— and $C_2H_5NHS$—. Dialkylaminothio: such as $(CH_3)_2NS$— and —$(C_2H_5)_2NS$—. Alkylaminosulfonyl: alkyl-NH—$SO_2$—. Dialkylaminosulfonyl: $(alkyl)_2$-N—$SO_2$—. Alkylsulfonylaminocarbonyl: alkyl-$SO_2$—NH—CO—. Alkylcarbonylaminosulfonyl: alkyl-CO—NH—$SO_2$—. Alkylcarbonylalkyl: alkyl-CO-alkyl-. Alkylsulfonyloxy: alkyl-$S(O)_2$—. Halogenated alkylsulfonyloxy: hydrogen atoms on alkyl of alkylsulfonyloxy can be partially or fully replaced by halogen atoms, such as $CF3-SO_2$—O. Cycloalkyloxycarbonyl: such as cyclopropoxycarbonyl, cyclohexyloxycarbonyl and the like. Alkoxy: linear or branched alkyl, bonded to the structure through an oxygen atom. Halogenated alkoxyl: linear or branched alkoxyl, and hydrogen atoms on the alkoxyl can be partially or fully replaced by halogen atoms. For example, chloromethoxy, dichoromethoxy, trichloromethoxy, fluoromethoxy, difluoromethoxy, trifluoromethoxy, chlorofluoromethoxy, trifluoroethoxy and the like. Halogenated alkoxycarbonyl: hydrogen atoms on alkyl of alkoxycarbonyl can be partially or fully replaced by halogen atoms, such as $ClCH_2CH_2OCO$—, $CF3CH_2OCO$— and the like. Alkoxyalkyl: alkyl-O-alkyl-, such as $CH_3OCH_2$—. Halogenated alkoxyalkyl: hydrogen atoms on alkyl of alkoxyalkyl can be partially or fully replaced by halogen atoms, such as $CCH_2CH_2OCH_2$—, $CF3CH_2OCH_2$— and the like. Alkoxycarbonyl-alkyl: alkoxycarbonyl-alkyl-, such as $CH_3OCOCH_2$—. Halogenated alkoxycarbonylalkyl: hydrogen atoms on alkyl of alkoxycarbonylalkyl can be partially or fully replaced by halogen atoms, such as $CF3CH_2OCOCH_2$—. Alkylcarbonyloxy: such as $CH_3COO$—, and the like. Halogenated alkylcarbonyloxy: hydrogen of alkylcarbonyloxy can be partially or fully replaced by halogen atoms, such as $CF3COO$—, and the like. Alkoxycarbonyloxy: alkoxycarbonyl-oxy-, such as $CH_3OCOO$—. Halogenated alkoxycarbonyloxy: hydrogen atoms on alkyl of alkoxycarbonyloxy can be partially or fully replaced by halogen atoms, such as $CF3OCOO$—. Alkylthiocarbonylalkyl: alkylthiocarbonyl-alkyl-, such as $CH_3SCOCH_2$—, halogenated alkylthiocarbonylalkyl: hydrogen atoms on alkyl of alkylthiocarbonylalkyl can be partially or fully replaced by halogen atoms, such as $CF3CH_2SCOCH_2$—. Alkoxyalkoxy: such as $CH_3OCH_2O$—, and the like. Halogenated alkoxyalkoxy: hydrogen atoms on alkoxyalkoxy can be partially or fully replaced by halogen atoms, such as $CF3OCH_2O$—. Alkoxyalkoxycarbonyl: such as $CH_3OCH_2CH_2CO$—, and the like. Alkylthio: linear or branched alkyl, bonded to the structure through a sulfur atom. Halogenated alkylthio: linear or branched alkylthio, and hydrogen atoms on the alkyls can be partially or fully replaced by halogen atoms. For example, chloromethylthio, dichloromethylthio, trichloromethylthio, fluoromethylthio, difluoromethylthio, trifluoromethylthio, chlorofluoromethylthio, and the like. Alkylthioalkyl: alkyl-S-alkyl-, such as $CH_3SCH_2$—. Halogenated alkylthioalkyl: hydrogen atoms on alkyl of alkylthioalkyl can be partially or fully replaced by halogen atoms, such as $ClCH_2CH_2SCH_2$—, $CF3CH_2SCH_2$—, and the like. Alkylamino: linear or branched alkyl, bonded to the structure through a nitrogen atom. Halogenated alkylamino: linear or branched alkylamino, and hydrogen atoms on the alkyl can be partially or fully replaced by halogen atoms. Dialkylamino: such as $(CH_3)_2N$— and $(CH_3CH_2)_2N$—. Halogenated dialkylamino: hydrogen atoms on alkyl can be partially or fully replaced by halogen atoms, such as $(CF3)_2N$— and $(CF3CH_2)_2N$—. Alkenyl: linear or branched alkene, such as vinyl, 1-propenyl, 2-propenyl and different butenyl, pentenyl and hexenyl isomers. The alkenyl also comprises polyenes, such as 1,2-propadienyl and 2,4-hexadienyl. Halogenated alkenyl: linear or branched alkene, and hydrogen atoms on the alkenyl can be partially or fully replaced by halogen atoms. Alkenyloxy: linear or branched alkene, bonded to the structure through an oxygen atom. Halogenated alkenyloxy: linear or branched alkenyloxy, and hydrogen atoms on the alkenyloxy can be partially or fully replaced by halogen atoms. Alkenylthio: linear or branched alkene, bonded to the structure through a sulphur atom. For example, $CH_2=CHCH_2S$—. Alkenoxycarbonyl: such as $CH_2=CHCH_2OCO$—, and the like. Alkynyl: linear or branched alkyne, such as ethynyl, 1-propynyl, 2-propynyl and different butynyl, pentynyl and hexynyl isomers. The alkynyl also comprises a group consisting of multiple triple bonds, such as 2,5-hexadiynyl. Halogenated alkynyl: linear or branched alkyne, and hydrogen atoms on the alkynyl can be partially or fully replaced by halogen atoms. Alkynyloxy: linear or branched alkyne, bonded to the structure through an oxygen atom. Halogenated alkynyloxy: linear or branched alkynyloxy, and hydrogen atoms on the alkynyloxy can be partially or fully replaced by halogen atoms. Alkynyloxycarbonyl, such as $CH\equiv CCH_2OCO$—, and the like. Alkylsulfonyl: linear or branched alkyl, connected to the structure through sulfonyl (—$SO_2$—), such as methylsulfonyl. Halogenated alkylsulfonyl: linear or branched alkylsulfonyl, and hydrogen atoms on the alkyl can be partially or fully replaced by halogen atoms. Alkylcarbonyl: alkyl, connected to the structure through carbonyl, such as $CH_3CO$— and $CH_3CH_2CO$—. Halogenated alkylcarbonyl: hydrogen atoms on alkyl of alkylcarbonyl can be partially or fully replaced by halogen atoms, such as $CF3CO$—. Alkoxycarbonyl: alkoxyl, connected to the structure through carbonyl, such as $CH_3OCO$— and $CH_3CH_2CO$—. Aminocarbonyl: such as $NH_2CO$—. Alkylaminocarbonyl: alkyl-NH—CO—, such as $CH_3NHCO$— and $CH_3CH_2NHCO$—. Dialkylaminocarbonyl: such as $(CH_3)_2NCO$— and $(CH_3CH_2)_2NCO$—. Aryl parts of (hetero) aryl, (hetero) arylalkyl, (hetero) arylcarbonyl, (hetero) arylmethylcarbonyl, (hetero) arylcarbonylalkyl, (hetero) aryloxycarbonyl and (hetero) arylalkyloxycarbonyl comprise phenyl or naphthyl. Heteroaryl is a five-membered or six-membered ring containing one or more N, O and S hetero atoms, such as furyl, pyrazolyl, thiazolyl, pyridyl, pyrimidinyl, pyrazinyl, pyridazinyl, triazinyl, quinolinyl, and the like. (Hetero) aryl: such as phenyl, and the like. (Hetero) arylalkyl: such as benzyl, phenethyl, parachloro-benzyl, 2-chloropyridine-5-yl, 2-chloro-thiazol-5-yl, and the like. (Hetero) arylcarbonyl: such as benzoyl, 4-chlorobenzoyl, and the like. (Hetero) arylmethylcarbonyl: such as $PhCH_2CO$—. (Hetero) arylcarbonylalkyl: such as $PhCOCH_2$—. (Hetero) aryloxycarbonyl: such as phenoxycarbonyl, 4-chlorophenoxycarbonyl, 4-nitrophenoxycarbonyl, naphthyloxycarbonyl, and the like. Arylalkyloxycarbonyl: such as benzyloxycarbonyl, 4-chlorobenzyloxycarbonyl, 4-trifluoromethylbenzyloxycarbonyl, and the like. (Hetero) arylalkyloxycarbonyl: such as $PhCH_2OCO$—, 4-Cl-$PhCH_2OCO$—, and the like.

Table 1, Table 2, Table 3, Table 4, Table 5, Table 6, Table 7 and Table 8 respectively list some specific substituents of $R_1$, $R_2$, $R_3(X=NR_3)$, $R_4$, $R_5$, $R_6$, $R_7$, $R_8$, $R_9$ and W in the general formula I, but not limited to the substituents.

I

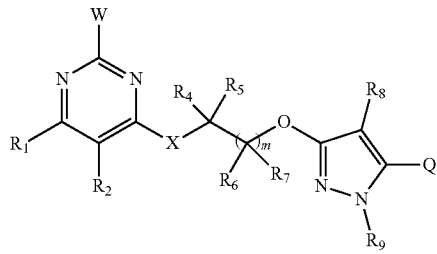

TABLE 1

$R_1$ Substituents $R_1$

H
I
i-$C_3H_7$
i-$C_4H_9$
$CH_2Cl$
$CH(CH_3)Cl$
$C\equiv CH$
CN
$COOCH_3$
$OCH_3$
$OCH_2CH=CHCl$
$CONH_2$
$NHC_2H_5$
$CH_2OCH_2CH_3$
$CH_2CH_2CH_2OCH_2CH_3$
F
$CH_3$
n-$C_4H_9$
$CF_3$
$CHBr_2$
$CH(CH_3)Br$
$SCH_3$
$NO_2$
$COOC_2H_5$
$OC_2H_5$
$OCH_2C\equiv CH$
$CONHCH_2$
$N(CH_3)_2$
$CH_2CH_2OCH_3$

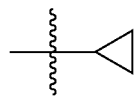

Cl
$C_2H_5$
s-$C_4H_9$
$CCl_3$
$CF_3CH_2$
$C(CH_3)_2F$
$SOCH_3$
$NH_2$
$CH_3NH$
$OCF_3$

TABLE 1-continued

R₁ Substituents

| R₁ |
|---|
| OCH₂C≡C-1 |
| CON(CH₃)₂ |
| N(C₂H₅)₂ |
| CH₂CH₂OCH₂CH₃ |
| cyclopentyl |
| Br |
| n-C₃H₇ |
| i-C₄H₉ |
| CHF₂ |
| CH(CH₃)F |
| CH=CH₂ |
| SO₂CH₃ |
| COOH |
| C₂H₅NH |
| OCH₂CH=CH₂ |
| OCH₂C≡CCH₃ |
| NHCH₃ |
| CH₂OCH₃ |
| CH₂CH₂CH₂OCH₃ |
| cyclohexyl |

TABLE 2

R₂ Substituent

| R₂ | R₂ | R₂ | R₂ |
|---|---|---|---|
| H | F | Cl | Br |
| I | CN | NO₂ | NH₂ |
| CHO | CH₃ | C₂H₅ | n-C₃H₇ |
| i-C₃H₇ | n-C₄H₉ | s-C₄H₉ | i-C₄H₉ |
| t-C₄H₉ | OCH₃ | OC₂H₅ | OC₃H₇-n |
| OC₃H₇-i | OC₄H₉-n | OC₄H₉-i | OC₄H₉-i |
| OCH₂F | OCHF₂ | OCF₃ | OCH₂CF₃ |

TABLE 3

R₃ Substituent

| R₃ |
|---|
| H |
| CH₃ |
| n-C₄H₉ |
| CH₂Br |
| CH₂Cl |
| OCH₃ |
| OCF₃ |
| SCH₃ |
| CH₂CH=CH₂ |
| CH₂C≡C-1 |
| CH₂CH₂OCH₂CH₃ |
| CH₂SCH₃ |
| CH₂SCH₂Cl |
| SOC₂H₅ |
| SO₂C₂H₅ |
| SO₂NHCH₃ |
| COC₂H₅ |
| CO-i-C₄H₉ |
| COOCH₃ |
| COOCF₃ |

TABLE 3-continued

R₃ Substituent

| R₃ |
|---|
| CH₂COOC₂H₅ |
| CONHC₂H₅ |
| COOCH₂CH=CH₂ |
| SNHCH₃ |
| cyclopropyl |
| CO—O-cyclopropyl |
| benzyl |
| 4-CF₃-benzyl |
| 2,6-dichloro-4-CF₃-benzyl |
| phenethyl |
| CO-(4-NO₂-phenyl) |
| CO—O-(4-CH₃-phenyl) |
| CO—O—CH₂-phenyl |
| CO—O—CH₂-(4-NO₂-phenyl) |
| CH₂—C(=O)-(4-Cl-phenyl) |
| OH |
| C₂H₅ |
| i-C₄H₉ |
| CHF₂ |
| CHCl₂ |
| OC₂H₅ |
| OCH₂CF3 |

TABLE 3-continued

R₃ Substituent

R₃

SC₂H₅
CH₂CH=CCl₂
CH₂OCH₃
CH₂OCH₂Cl
CH₂SCH₂CH₃
CH₂SCH₂CH₂Cl
SOCF₃
SO₂CF₃
SO₂N(CH₃)₃
CO-n-C₃H₇
CO-t-C₄H9
COOC₂H₅
COOCH₂CH₂Cl
CH₂COCH₃
CONH-t-C₄H₉
COOCH₂C≡CH
SNHC₂H₅

[cyclobutyl group]

CO—O—[cyclobutyl]

[CH₂-phenyl-Cl (4-chlorobenzyl)]

[CH₂-2,4-dimethylphenyl]

[CH₂-pyridyl-Cl (6-chloro-3-pyridylmethyl)]

[CH₂CH₂-phenyl-Cl (4-chlorophenethyl)]

CO—[phenyl]—CF₃

CO—O—[phenyl]—CF₃

CO—O—[CH₂-phenyl]—CH₃

CO—O—[CH₂-phenyl]—OCH₃

TABLE 3-continued

R₃ Substituent

R₃

[C(=O)-phenyl-Br (4-bromobenzoyl methyl)]

—C(=O)H
n-C₃H₇
i-C₄H₉
CHBr₂
CCl₂
OCH(CH₃)₂
OCH₂F
SCH₂CH=CH₂
C≡CH
CH₂OCH₂CH₃
CH₂OCH₂CH₂Cl
CH₂CH₂SCH₃
CH₂CH₂SCH₂Cl
SOCH₂CF₃
SO₂CH₂CF₃
CONHSCO₂CH₃
CO-i-C₃H₇
COCF₃
COO-n-C₃H₇
COOCH₂CF₃
CH₂COC₂H₅
CON(CH₃)₂
COOCH₂OCH₃
SN(CH₃)₂

[cyclopentyl]

CO—O—[cyclopentyl]

[CH₂-2-chlorophenyl]

[CH₂-2,4-dichlorophenyl]

[CH₂-thiazolyl-Cl (5-chloro-2-thiazolylmethyl)]

CO—[phenyl]

CO—[phenyl]—Cl

TABLE 3-continued
R₃ Substituent
R₃
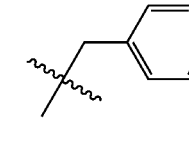
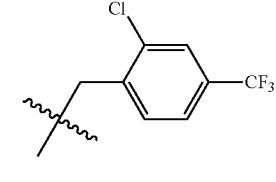 [SMILES: *Cc1ccc(C(F)(F)F)cc1Cl]
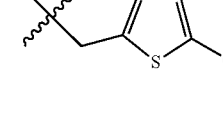
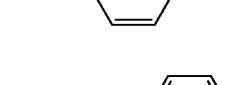
CBr₃
i-C₃H₇
CCl₃
CF₃
CH₂F
OC(CH₃)₃
OCHF₃
CH=CH₃
CH₂C≡CH
CH₂CH₂OCH₃
CH₂CH₂OCH₂Cl
CH₂CH₂SCH₂CH₃
SOCH₃
SO₂CH₃
SO₂NHCOCH₃
COCH₅
CO-n-C₄H₉
COCH₂Cl
COO-t-C₄H₉
CH₂COOCH₃
CONHCH₃
CON(C₂H₅)₂
COOCH₂CH₂OCH₃
SN(C₂H₅)₂
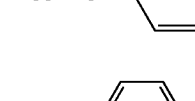
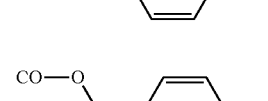
TABLE 3-continued
R₃ Substituent
R₃
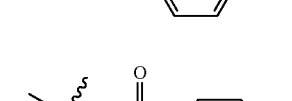
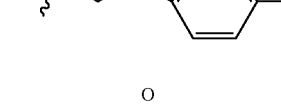
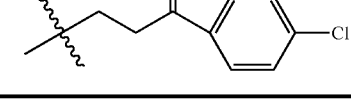

TABLE 4

R₄(R₅) Substituent

| $R_4(R_5)$ | $R_4(R_5)$ | $R_4(R_5)$ | $R_4(R_5)$ |
|---|---|---|---|
| H | F | Cl | Br |
| I | $CH_3$ | $C_2H_5$ | $n\text{-}C_3H_7$ |
| $i\text{-}C_3H_7$ | $n\text{-}C_4H_9$ | $s\text{-}C_4H_9$ | $i\text{-}C_4H_9$ |
| $t\text{-}C_4H_9$ | $CF_3$ | $CCl_3$ | $CHF_2$ |
| $CH_2Cl$ | $CHBr_2$ | $CF_3CH_2$ | $CH(CH_3)F$ |
| $CH(CH_3)Cl$ | $CH(CH_3)Br$ | $C(CH_3)_2F$ | $OCH_3$ |
| $OC_2H_5$ | $n\text{-}C_3H_7O$ | $i\text{-}C_3H_7O$ | $n\text{-}C_4H_9O$ |
| $s\text{-}C_4H_9O$ | $i\text{-}C_4H_9O$ | $t\text{-}C_4H_9O$ | $OCF_3$ |
| $OCH_2CF_3$ | 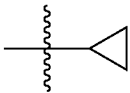 [SMILES: *C1CC1] | 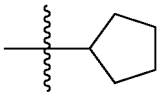 | 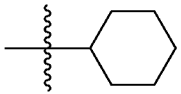 |

$CR_4R_5$

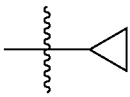 [SMILES: *C1CC1]

TABLE 5

R₆(R₇) Substituent

| $R_6(R_7)$ | $R_6(R_7)$ | $R_6(R_7)$ | $R_6(R_7)$ |
|---|---|---|---|
| H | F | Cl | Br |
| I | $CH_3$ | $C_2H_5$ | $n\text{-}C_3H_7$ |
| $i\text{-}C_3H_7$ | $n\text{-}C_4H_9$ | $s\text{-}C_4H_9$ | $i\text{-}C_4H_9$ |
| $t\text{-}C_4H_9$ | $CF_3$ | $CCl_3$ | $CHF_2$ |
| $CH_2Cl$ | $CHBr_2$ | $CF_3CH_2$ | $CH(CH_3)F$ |
| $CH(CH_3)Cl$ | $CH(CH_3)Br$ | $C(CH_3)_2F$ | $OCH_3$ |
| $OC_2H_5$ | $n\text{-}C_3H_7O$ | $i\text{-}C_3H_7O$ | $n\text{-}C_4H_9O$ |
| $s\text{-}C_4H_9O$ | $i\text{-}C_4H_9O$ | $t\text{-}C_4H_9O$ | $OCF_3$ |
| $OCH_2CF_3$ | 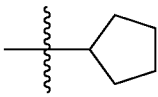 [SMILES: *C1CCCC1] | | |

$CR_6R_7$

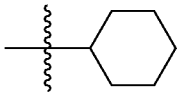 [SMILES: *C1CCCCC1]

TABLE 6

R_8 Substituent

| R_8 | R_8 | R_8 | R_8 |
|---|---|---|---|
| H | CN | $CH_3$ | $C_2H_5$ |
| n-$C_3H_7$ | i-$C_3H_7$ | n-$C_4H_9$ | s-$C_4H_9$ |
| i-$C_4H_9$ | i-$C_4H_9$ | $CF_3$ | $CCl_3$ |
| $CHF_2$ | $CH_2F$ | $CH_2Cl$ | $CH_2CF_3$ |
| $CF_2CF_3$ | $COOCH_3$ | Ph | Ph-4-Cl |

TABLE 7

R_9 Substituent

| $R_{10}$ | $R_{10}$ | $R_{10}$ | $R_{10}$ | $R_{10}$ |
|---|---|---|---|---|
| $CH_3$ | Et | n-Pr | i-Pr | n-Bu |
| i-Bu | s-Bu | t-Bu | $CH_2F$ | $CHF_2$ |
| $CF_3$ | $CH_2CF_3$ | $COCH_3$ | COEt | CO-n-Pr |
| CO-n-Bu | CO-t-Bu | $COCF_3$ | $CO_2CH_3$ | $CO_2Et$ |
| $CO_2$-n-Pr | $CO_2$-i-Pr | $CO_2$-t-Bu | $CO_2CH_2CF_3$ | $CH_2OCH_3$ |

TABLE 7-continued

R9 Substituent

| R10 | R10 | R10 | R10 | R10 |

TABLE 8

W Substituent

| W | W | W | W | W |
|---|---|---|---|---|
| H | i-$C_3H_7$ | $CHF_2$ | $OCH_3$ | $SCH_3$ |
| F | n-$C_4H_9$ | $CHBr_2$ | $OC_2H_5$ | $SC_2H_5$ |
| Cl | i-$C_4H_9$ | $CF_3$ | $OC_3H_7$-n | $SC_3H_7$-n |
| Br | $CH_3$ | $CH(CH_3)F$ | $OC_3H_7$-i | $SC_3H_7$-i |
| I | $C_2H_5$ | $CH(CH_3)Cl$ | $OC_4H_9$-i | $SC_4H_9$-n |
|  | $CHCl_2$ | $CH(CH_3)Br$ | $OC_4H_9$-i | $SC_4H_9$-i |
|  | $CCl_3$ | $CH(n-C_4H_9)F$ | $OC_4H_9$-t | $SC_4H_9$-t |
|  |  | $C(CH_3)_2F$ | $OCF_3$ | $SO_2CH_3$ |
|  |  | n-$C_3H_7$ | $OCH_2CF_3$ | t-$C_4H_9$ |

Part of compounds in the present invention can be illustrated by specific compounds listed in Table 9 to Table 32, but not to limit the present invention. In the general formula compounds I-1A, I-1B, I-1C and I-1D involved in the table, $W=R_6=R_7=R_{13}=R_{14}=R_{15}=R_{16}=R_{17}=H$, $R_9=CH_3$.

In the general formula I-1A,

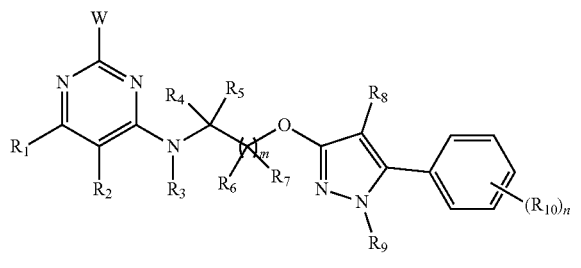

I-1A

When $R_1=Cl$, $R_2=Cl$, $R_3=R_4=R_5=H$, $R_8=H$, $m=1$, the $(R_{10})n$ substituent is shown in Table 9, and the numbers of representative compounds are successively 9-1 to 9-288.

TABLE 9

| No. | $(R_{10})n$ |
|---|---|
| 9-1 | H |
| 9-2 | 2-F |
| 9-3 | 3-F |
| 9-4 | 4-F |
| 9-5 | 2,3-diF |
| 9-6 | 2,4-diF |
| 9-7 | 2,5-diF |
| 9-8 | 2,6-diF |
| 9-9 | 3,4-diF |
| 9-10 | 3,5-diF |
| 9-11 | 2,3,4-triF |
| 9-12 | 2,3,5-triF |
| 9-13 | 2,4,5-triF |
| 9-14 | 2,3,6-triF |
| 9-15 | 2,4,6-triF |
| 9-16 | 3,4,5-triF |
| 9-17 | 2-Cl |
| 9-18 | 3-Cl |
| 9-19 | 4-Cl |
| 9-20 | 2,3-diCl |
| 9-21 | 2,4-diCl |
| 9-22 | 2,5-diCl |
| 9-23 | 2,6-diCl |
| 9-24 | 3,4-diCl |
| 9-25 | 3,5-diCl |
| 9-26 | 2,3,4-triCl |
| 9-27 | 2,3,5-triCl |
| 9-28 | 2,4,5-triCl |
| 9-29 | 2,3,6-triCl |
| 9-30 | 2,4,6-triCl |
| 9-31 | 3,4,5-triCl |
| 9-32 | 2-Br |
| 9-33 | 3-Br |
| 9-34 | 4-Br |
| 9-35 | 2,3-diBr |
| 9-36 | 2,4-diBr |
| 9-37 | 2,5-diBr |
| 9-38 | 2,6-diBr |
| 9-39 | 3,4-diBr |
| 9-40 | 3,5-diBr |
| 9-41 | 2,3,4-triBr |
| 9-42 | 2,3,5-triBr |
| 9-43 | 2,4,5-triBr |
| 9-44 | 2,3,6-triBr |
| 9-45 | 2,4,6-triBr |
| 9-46 | 3,4,5-triBr |
| 9-47 | 2-CN |
| 9-48 | 3-CN |

TABLE 9-continued

| No. | $(R_{10})n$ |
|---|---|
| 9-49 | 4-CN |
| 9-50 | $2\text{-}NO_2$ |
| 9-51 | $3\text{-}NO_2$ |
| 9-52 | $4\text{-}NO_2$ |
| 9-53 | $2,4\text{-}diNO_2$ |
| 9-54 | $2,4,6\text{-}3NO_2$ |
| 9-55 | $2\text{-}CH_3$ |
| 9-56 | $3\text{-}CH_3$ |
| 9-57 | $4\text{-}CH_3$ |
| 9-58 | $2,3\text{-}diCH_3$ |
| 9-59 | $2,4\text{-}diCH_3$ |
| 9-60 | $2,5\text{-}diCH_3$ |
| 9-61 | $2,6\text{-}diCH_3$ |
| 9-62 | $3,4\text{-}diCH_3$ |
| 9-63 | $3,5\text{-}diCH_3$ |
| 9-64 | $2\text{-}C_2H_5$ |
| 9-65 | $3\text{-}C_2H_5$ |
| 9-66 | $4\text{-}C_2H_5$ |
| 9-67 | $2\text{-}CF_3$ |
| 9-68 | $3\text{-}CF_3$ |
| 9-69 | $4\text{-}CF_3$ |
| 9-70 | $2\text{-}OCH_3$ |
| 9-71 | $3\text{-}OCH_3$ |
| 9-72 | $4\text{-}OCH_3$ |
| 9-73 | $2\text{-}SCH_3$ |
| 9-74 | $3\text{-}SCH_3$ |
| 9-75 | $4\text{-}SCH_3$ |
| 9-76 | $2\text{-}OCF_3$ |
| 9-77 | $3\text{-}OCF_3$ |
| 9-78 | $4\text{-}OCF_3$ |
| 9-79 | $2\text{-}SCF_3$ |
| 9-80 | $3\text{-}SCF_3$ |
| 9-81 | $4\text{-}SCF_3$ |
| 9-82 | $2\text{-}OC_2H_5$ |
| 9-83 | $3\text{-}OC_2H_5$ |
| 9-84 | $4\text{-}OC_2H_5$ |
| 9-85 | $2\text{-}NHCH_3$ |
| 9-86 | $3\text{-}NHCH_3$ |
| 9-87 | $4\text{-}NHCH_3$ |
| 9-88 | $2\text{-}N(CH_3)_2$ |
| 9-89 | $3\text{-}N(CH_3)_2$ |
| 9-90 | $4\text{-}N(CH_3)_2$ |
| 9-91 | $2\text{-}COCH_3$ |
| 9-92 | $3\text{-}COCH_3$ |
| 9-93 | $4\text{-}COCH_3$ |
| 9-94 | $2\text{-}COC_2H_5$ |
| 9-95 | $3\text{-}COC_2H_5$ |
| 9-96 | $4\text{-}COC_2H_5$ |
| 9-97 | $2\text{-}SO_2CH_3$ |
| 9-98 | $3\text{-}SO_2CH_3$ |
| 9-99 | $4\text{-}SO_2CH_3$ |
| 9-100 | $2\text{-}OCHF_2$ |
| 9-101 | $3\text{-}OCHF_2$ |
| 9-102 | $4\text{-}OCHF_2$ |
| 9-103 | $2\text{-}SO_2C_2H_5$ |
| 9-104 | $3\text{-}SO_2C_2H_5$ |
| 9-105 | $4\text{-}SO_2C_2H_5$ |
| 9-106 | $2\text{-}CO_2CH_3$ |
| 9-107 | $3\text{-}CO_2CH_3$ |
| 9-108 | $4\text{-}CO_2CH_3$ |
| 9-109 | $2\text{-}CO_2C_2H_5$ |
| 9-110 | $3\text{-}CO_2C_2H_5$ |
| 9-111 | $4\text{-}CO_2C_2H_5$ |
| 9-112 | $2\text{-}CH_2OCH_3$ |
| 9-113 | $3\text{-}CH_2OCH_3$ |
| 9-114 | $4\text{-}CH_2OCH_3$ |
| 9-115 | $2\text{-}OCOCH_3$ |
| 9-116 | $3\text{-}OCOCH_3$ |
| 9-117 | $4\text{-}OCOCH_3$ |
| 9-118 | $2\text{-}OCOCH_2CH_3$ |
| 9-119 | $3\text{-}OCOCH_2CH_3$ |
| 9-120 | $4\text{-}OCOCH_2CH_3$ |
| 9-121 | $2\text{-}OCO_2CH_3$ |
| 9-122 | $3\text{-}OCO_2CH_3$ |
| 9-123 | $4\text{-}OCO_2CH_3$ |
| 9-124 | $2\text{-}OCH_2OCH_3$ |
| 9-125 | $3\text{-}OCH_2OCH_3$ |
| 9-126 | $4\text{-}OCH_2OCH_3$ |

TABLE 9-continued

| No. | $(R_{10})n$ |
|---|---|
| 9-127 | 2-OCF$_2$OCF$_3$ |
| 9-128 | 3-OCF$_2$OCF$_3$ |
| 9-129 | 4-OCF$_2$OCF$_3$ |
| 9-130 | 2-COPh |
| 9-131 | 3-COPh |
| 9-132 | 4-COPh |
| 9-133 | 2-COCH$_2$Ph |
| 9-134 | 3-COCH$_2$Ph |
| 9-135 | 4-COCH$_2$Ph |
| 9-136 | 2-NHPh |
| 9-137 | 3-NHPh |
| 9-138 | 4-NHPh |
| 9-139 | 2-OPh |
| 9-140 | 3-OPh |
| 9-141 | 4-OPh |
| 9-142 | 2-CONHPh |
| 9-143 | 3-CONHPh |
| 9-144 | 4-CONHPh |
| 9-145 | 2-CO$_2$Ph |
| 9-146 | 3-CO$_2$Ph |
| 9-147 | 4-CO$_2$Ph |
| 9-148 | 2-CONH$_2$ |
| 9-149 | 3-CONH$_2$ |
| 9-150 | 4-CONH$_2$ |
| 9-151 | 2-Cl-4-F |
| 9-152 | 2-Cl-4-Br |
| 9-153 | 2-Cl-4-CH$_3$ |
| 9-154 | 2-Cl-4-CF$_3$ |
| 9-155 | 2-Cl-4-NO$_2$ |
| 9-156 | 2-Cl-4-CN |
| 9-157 | 2-Cl-4-OCF$_3$ |
| 9-158 | 2-F-4-Cl |
| 9-159 | 2-Br-4-Cl |
| 9-160 | 2-CH$_3$-4-Cl |
| 9-161 | 2-CF$_3$-4-Cl |
| 9-162 | 2-NO$_2$-4-Cl |
| 9-163 | 2-CN-4-Cl |
| 9-164 | 2-OCF$_3$-4-Cl |
| 9-165 | 2,6-diCl-4-NO$_2$ |
| 9-166 | 2,6-diCl-4-CF$_3$ |
| 9-167 | 2,6-diCl-4-CN |
| 9-168 | 2,6-diCl-4-COCH$_3$ |
| 9-169 | 2,6-diCl-4-CONH$_2$ |
| 9-170 | 2,4-diCl-6-NO$_2$ |
| 9-171 | 2,4-diCl-6-CN |
| 9-172 | 2,4-diCl-6-CF$_3$ |
| 9-173 | 2,4-diF-6-NO$_2$ |
| 9-174 | 2,6-diF-4-NO$_2$ |
| 9-175 | 2-NO$_2$-4-F |
| 9-176 | 2-NO$_2$-4-Br |
| 9-177 | 2-NO$_2$-4-CF$_3$ |
| 9-178 | 2-NO$_2$-4-CN |
| 9-179 | 2-NO$_2$-4-COCH$_3$ |
| 9-180 | 2-NO$_2$-4-CONH$_2$ |
| 9-181 | 2-NO$_2$-4-CH$_3$ |
| 9-182 | 2-NO$_2$-4-OCH$_3$ |
| 9-183 | 2-NO$_2$-4-SCH$_3$ |
| 9-184 | 2-NO$_2$-4-NHCH$_3$ |
| 9-185 | 2-F-4-NO$_2$ |
| 9-186 | 2-Br-4-NO$_2$ |
| 9-187 | 2-CF$_3$-4-NO$_2$ |
| 9-188 | 2-CN-4-NO$_2$ |
| 9-189 | 2-COCH$_3$-4-NO$_2$ |
| 9-190 | 2-CONH$_2$-4-NO$_2$ |
| 9-191 | 2-CH$_3$-4-NO$_2$ |
| 9-192 | 2-Cl-4-F-6-NO$_2$ |
| 9-193 | 2-Cl-4-Br-6-NO$_2$ |
| 9-194 | 2-Cl-4-CH$_3$-6-NO$_2$ |
| 9-195 | 2-Cl-4-CF$_3$-6-NO$_2$ |
| 9-196 | 2-Cl-4,6-diNO$_2$ |
| 9-197 | 2-Cl-4-CN-6-NO$_2$ |
| 9-198 | 2-Cl-4-OCF$_3$-6-NO$_2$ |
| 9-199 | 2-F-4-Cl-6-NO$_2$ |
| 9-200 | 2-Br-4-Cl-6-NO$_2$ |
| 9-201 | 2-CH$_3$-4-Cl-6-NO$_2$ |
| 9-202 | 2-CF$_3$-4-Cl-6-NO$_2$ |
| 9-203 | 4-Cl-2,6-diNO$_2$ |
| 9-204 | 2-CF$_3$-4-CN |
| 9-205 | 2-CN-4-CF$_3$ |
| 9-206 | 4-CF$_3$-2,6-diNO$_2$ |
| 9-207 | 4-CN-2,6-diNO$_2$ |
| 9-208 | 4-CH$_3$-2,6-diNO$_2$ |
| 9-209 | 4-OCF$_3$-2,6-diNO$_2$ |
| 9-210 | 4-OCH$_3$-2,6-diNO$_2$ |
| 9-211 | 4-SCH$_3$-2,6-diNO$_2$ |
| 9-212 | 4-NHCH$_3$-2,6-diNO$_2$ |
| 9-213 | 4-F-2,6-diNO$_2$ |
| 9-214 | 2-CF$_3$-4,6-diNO$_2$ |
| 9-215 | 2-CN-4,6-diNO$_2$ |
| 9-216 | 2-CH$_3$-4,6-diNO$_2$ |
| 9-217 | 2-F-4,6-diNO$_2$ |
| 9-218 | 2-OCF$_3$-4,6-diNO$_2$ |
| 9-219 | 2-CF$_3$-4-Br |
| 9-220 | 3-CF$_3$-4-NO$_2$ |
| 9-221 | 2-CN-4-Cl-6-NO$_2$ |
| 9-222 | 2-OCF$_3$-4-Cl-6-NO$_2$ |
| 9-223 | 3-CF$_3$-4-CN |
| 9-224 | 3-CN-4-CF$_3$ |
| 9-225 | 2-CF$_3$-4-Br-6-NO$_2$ |
| 9-226 | 3-NO$_2$-4-CF$_3$ |
| 9-227 | 2-NO$_2$-4-CN-5-CF$_3$ |
| 9-228 | 2-NO$_2$-4-CF$_3$-5-CN |
| 9-229 | 4-OCF$_3$-2,6-diBr |
| 9-230 | 2-CH$_3$-4-Cl-5-CH$_2$CO$_2$C$_2$H$_5$ |
| 9-231 | 2,4-diCl-3-CH$_3$ |
| 9-232 | 2,4-diCl-3-CH$_3$-6-NO$_2$ |
| 9-233 | 2-Cl-3-CH$_3$ |
| 9-234 | 2-CH$_3$-3-Cl |
| 9-235 | 2-CH$_3$-3-Cl-4,6-diNO$_2$ |
| 9-236 | 2-CH$_3$-3-Cl-4-NO$_2$ |
| 9-237 | 2-CH$_3$-3-Cl-6-NO$_2$ |
| 9-238 | 2-Cl-3-CH$_3$-4,6-diNO$_2$ |
| 9-239 | 2-Cl-3-CH$_3$-4-NO$_2$ |
| 9-240 | 2-Cl-3-CH$_3$-6-NO$_2$ |
| 9-241 | 2-Br-4-NO$_2$-6-CN |
| 9-242 | 3-Cl-4-CF$_3$-2,6-diNO$_2$ |
| 9-243 | 2-NO$_2$-4,5-diCl |
| 9-244 | 2-NO$_2$-3,5-diCl |
| 9-245 | 2,5-diCl-4-NO$_2$ |
| 9-246 | 2,5-diCl-6-NO$_2$ |
| 9-247 | 2,3-diCl-4-NO$_2$ |
| 9-248 | 2,3-diCl-6-NO$_2$ |
| 9-249 | 3,4-diCl-2,6-diNO$_2$ |
| 9-250 | 2,5-diCl-4,6-diNO$_2$ |
| 9-251 | 2,4,5-triCl-6-NO$_2$ |
| 9-252 | 2,3,4-triCl-5-NO$_2$ |
| 9-253 | 2,3,4-triCl-6-NO$_2$ |
| 9-254 | 2,3,5-triCl-4,6-diCN |
| 9-255 | 2,5-diCl-4-OCF$_2$OCF$_3$ |
| 9-256 | 2,6-diBr-4-NO$_2$ |
| 9-257 | 2-F-4-NO$_2$-6-Cl |
| 9-258 | 2-Cl-4-NO$_2$-6-SCN |
| 9-259 | 2-Br-4-NO$_2$-6-Cl |
| 9-260 | 2-Cl-4-NO$_2$-6-OCH$_3$ |
| 9-261 | 2-Cl-4-NO$_2$-6-SCH$_3$ |
| 9-262 | 2-Cl-4-NO$_2$-6-NHCH$_3$ |
| 9-263 | 2-Cl-4-NO$_2$-6-SO$_2$CH$_3$ |
| 9-264 | 2-Cl-4-SO$_2$CH$_3$ |
| 9-265 | 2,6-diCl-4-SO$_2$CH$_3$ |
| 9-266 | 2,6-diCl-4-CH$_3$ |
| 9-267 | 2,6-diCl-4-CO$_2$CH$_3$ |
| 9-268 | 2,6-diCl-4-CONHCH$_3$ |
| 9-269 | 2,6-diCl-4-CON(CH$_3$)$_2$ |
| 9-270 | 2,6-diCl-4-CF(CF$_3$)$_2$ |
| 9-271 | 2-Cl-4-CF(CF$_3$)$_2$-6-Br |
| 9-272 | 2-F-4-CF(CF$_3$)$_2$-6-Br |
| 9-273 | 2-F-4-CF(CF$_3$)$_2$-6-Cl |
| 9-274 | 2,6-diF-4-CF(CF$_3$)$_2$-6-Cl |
| 9-275 | 2,4,5-triCl-3,6-2CN |
| 9-276 | 2,3,5-triF-4,6-diCN |
| 9-277 | 2-SO$_2$NH$_2$ |
| 9-278 | 3-SO$_2$NH$_2$ |
| 9-279 | 4-SO$_2$NH$_2$ |
| 9-280 | 2-i-C$_3$H$_7$ |
| 9-281 | 3-i-C$_3$H$_7$ |
| 9-282 | 4-i-C$_3$H$_7$ |

TABLE 9-continued

| No. | $(R_{10})n$ |
|---|---|
| 9-283 | 2-n-$C_4H_9$ |
| 9-284 | 3-n-$C_4H_9$ |
| 9-285 | 4-n-$C_4H_9$ |
| 9-286 | 2-t-$C_4H_9$ |
| 9-287 | 3-t-$C_4H_9$ |
| 9-288 | 4-t-$C_4H_9$ |

Table 9-1: in the general formula I-1A, when $R_1$=Cl, $R_2$=$CH_3$, $R_3$=$R_4$=$R_5$=H, $R_8$=H and m=1, the substituent $(R_{10})n$ is identical to that in Table 9, and sequentially corresponds to 9-1 to 9-288 of Table 9, and the numbers of representative compounds are successively 9-1-1 to 9-1-288.

Table 9-2: in the general formula I-1A, when $R_1$=Cl, $R_2$=$OCH_3$, $R_3$=$R_4$=$R_5$=H, $R_8$=H and m=1, the substituent $(R_{10})n$ is identical to that in Table 9, and sequentially corresponds to 9-1 to 9-288 of Table 9, and the numbers of representative compounds are successively 9-2-1 to 9-2-288.

Table 9-3: in the general formula I-1A, when $R_1$=Cl, $R_2$=CHO, $R_3$=$R_4$=$R_5$=H, $R_8$=H and m=1, the substituent $(R_{10})n$ is identical to the substituent shown in Table 9, and sequentially corresponds to 9-1 to 9-288 of Table 9, and the numbers of representative compounds are successively 9-3-1 to 9-3-288.

Table 9-4: in the general formula I-1A, when $R_1$=Cl, $R_2$=Br, $R_3$=$R_4$=$R_5$=H, $R_8$=H and m=1, the substituent $(R_{10})n$ is identical to the substituent shown in Table 9, and sequentially corresponds to 9-1 to 9-288 of Table 9, and the numbers of representative compounds are successively 9-4-1 to 9-4-288.

Table 10: in the general formula I-1A, when $R_1$=$CH_3$, $R_2$=Cl, $R_3$=$R_4$=$R_5$=H, $R_8$=H and m=1, the substituent $(R_{10})n$ is identical to the substituent shown in Table 9, and sequentially corresponds to 9-1 to 9-288 of Table 9, and the numbers of representative compounds are successively 10-1 to 10-288.

Table 10-1: in the general formula I-1A, when $R_1$=$CH_3$, $R_2$=Cl, $R_3$=$R_4$=$R_5$=H, $R_8$=$CH_3$ and m=1, the substituent $(R_{10})n$ is identical to the substituent shown in Table 9, and sequentially corresponds to 9-1 to 9-288 of Table 9, and the numbers of representative compounds are successively 10-1-1 to 10-1-288.

Table 10-2: in the general formula I-1A, when $R_1$=$CH_3$, $R_2$=Cl, $R_3$=$R_4$=$R_5$=H, $R_8$=H and m=2, the substituent $(R_{10})n$ is identical to the substituent shown in Table 9, and sequentially corresponds to 9-1 to 9-288 of Table 9, and the numbers of representative compounds are successively 10-2-1 to 10-2-288.

Table 10-3: in the general formula I-1A, when $R_1$=$CH_3$, $R_2$=Cl, $R_3$=$R_4$=$R_5$=H, $R_8$=$CH_3$ and m=2, the substituent $(R_{10})n$ is identical to the substituent shown in Table 9, and sequentially corresponds to 9-1 to 9-288 of Table 9, and the numbers of representative compounds are successively 10-3-1 to 10-3-288.

Table 10-4: in the general formula I-1A, when $R_1$=$CH_3$, $R_2$=Cl, $R_3$=$R_4$=H, $R_5$=$R_8$=$CH_3$ and m=1, the substituent $(R_{10})n$ is identical to the substituent shown in Table 9, and sequentially corresponds to 9-1 to 9-288 of Table 9, and the numbers of representative compounds are successively 10-4-1 to 10-4-288.

Table 11: in the general formula I-1A, when $R_1$=$C_2H_5$, $R_2$=Cl, $R_3$=$R_4$=$R_5$=H, $R_8$=H and m=1, the substituent $(R_{10})n$ is identical to the substituent shown in Table 9, and sequentially corresponds to 9-1 to 9-288 of Table 9, and the numbers of representative compounds are successively 11-1 to 11-288.

Table-11-1: in the general formula I-1A, when $R_1$=$C_2H_5$, $R_2$=Cl, $R_3$=$R_4$=$R_5$=H, $R_8$=$CH_3$ and m=1, the substituent $(R_{10})n$ is identical to the substituent shown in Table 9, and sequentially corresponds to 9-1 to 9-288 of Table 9, and the numbers of representative compounds are successively 11-1-1 to 11-1-288.

Table 11-2: in the general formula I-1A, when $R_1$=$C_2H_5$, $R_2$=Cl, $R_3$=$R_4$=$R_5$=H, $R_8$=H and m=2, the substituent $(R_{10})n$ is identical to the substituent shown in Table 9, and sequentially corresponds to 9-1 to 9-288 of Table 9, and the numbers of representative compounds are successively 11-2-1 to 11-2-288.

Table 11-3: in the general formula I-1A, when $R_1$=$C_2H^5$, $R_2$=Cl, $R_3$=$R_4$=$R_5$=H, $R_8$=$CH_3$ and m=2, the substituent $(R_{10})n$ is identical to the substituent shown in Table 9, and sequentially corresponds to 9-1 to 9-288 of Table 9, and the numbers of representative compounds are successively 11-3-1 to 11-3-288.

Table 11-4: in the general formula I-1A, when $R_1$=$C_2H_5$, $R_2$=Cl, $R_3$=$R_4$=H, $R_5$=$R_8$=$CH_3$ and m=1, the substituent $(R_{10})n$ is identical to the substituent shown in Table 9, and sequentially corresponds to 9-1 to 9-288 of Table 9, and the numbers of representative compounds are successively 11-4-1 to 1-4-288.

Table 12: in the general formula I-1A, when $R_1$=CHF2, $R_2$=Cl, $R_3$=$R_4$=$R_5$=H, $R_8$=H and m=1, the substituent $(R_{10})n$ is identical to the substituent shown in Table 9, and sequentially corresponds to 9-1 to 9-288 of Table 9, and the numbers of representative compounds are successively 12-1 to 12-288.

Table 12-1: in the general formula I-1A, when $R_1$=CHF2, $R_2$=Cl, $R_3$=$R_4$=$R_5$=H, $R_8$=$CH_3$ and m=1, the substituent $(R_{10})n$ is identical to the substituent shown in Table 9, and sequentially corresponds to 9-1 to 9-288 of Table 9, and the numbers of representative compounds are successively 12-1-1 to 12-1-288.

Table 12-2: in the general formula I-1A, when $R_1$=CHF2, $R_2$=Cl, $R_3$=$R_4$=$R_5$=H, $R_8$=H and m=2, the substituent $(R_{10})n$ is identical to the substituent shown in Table 9, and sequentially corresponds to 9- to 9-288 of Table 9, and the numbers of representative compounds are successively 12-2-1 to 12-2-288.

Table 12-3: in the general formula I-1A, when $R_1$=CHF2, $R_2$=Cl, $R_3$=$R_4$=$R_5$=H, $R_8$=$CH_3$ and m=2, the substituent $(R_{10})n$ is identical to the substituent shown in Table 9, and sequentially corresponds to 9-1 to 9-288 of Table 9, and the numbers of representative compounds are successively 12-3-1 to 12-3-288.

Table 12-4: in the general formula I-1A, when $R_1$=CHF2, $R_2$=Cl, $R_3$=$R_4$=H, $R_5$=$R_8$=$CH_3$ and m=1, the substituent $(R_{10})n$ is identical to the substituent shown in Table 9, and sequentially corresponds to 9-1 to 9-288 of Table 9, and the numbers of representative compounds are successively 12-4-1 to 12-4-288.

Table 13: in the general formula I-1A, when $R_1$=CF3, $R_2$=Cl, $R_3$=$R_4$=$R_5$=H, $R_8$=H and m=1, the substituent $(R_{10})n$ is identical to the substituent shown in Table 9, and sequentially corresponds to 9-1 to 9-288 of Table 9, and the numbers of representative compounds are successively 13-1 to 13-288.

Table 14: in the general formula I-1A, when $R_1$=Cl, $R_2$=Cl, $R_3$=$R_4$=H, $R_5$=$CH_3$, $R_8$=H and m=1, the substituent $(R_{10})n$ is identical to the substituent shown in Table 9, and sequentially corresponds to 9-1 to 9-288 of Table 9, and the numbers of representative compounds are successively 14-1 to 14-288.

Table 15: in the general formula I-1A, when $R_1$=$CH_3$, $R_2$=Cl, $R_3$=$R_4$=H, $R_5$=$CH_3$, $R_8$=H and m=1, the substituent $(R_{10})n$ is identical to the substituent shown in Table 9, and sequentially corresponds to 9-1 to 9-288 of Table 9, and the numbers of representative compounds are successively 15-1 to 15-288.

Table 16: in the general formula I-1A, when $R_1$=$C_2H_5$, $R_2$=Cl, $R_3$=$R_4$=H, $R_5$=$CH_3$, $R_8$=H and m=1, the substituent $(R_{10})n$ is identical to the substituent shown in Table 9, and sequentially corresponds to 9-1 to 9-288 of Table 9, and the numbers of representative compounds are successively 16-1 to 16-288.

Table 17: in the general formula I-1A, when $R_1$=CHF2, $R_2$=Cl, $R_3$=$R_4$=H, $R_5$=$CH_3$, $R_8$=H and m=1, the substituent $(R_{10})n$ is identical to the substituent shown in Table 9, and sequentially corresponds to 9-1 to 9-288 of Table 9, and the numbers of representative compounds are successively 17-1 to 17-288.

Table 18: in the general formula I-1A, when $R_1$=$CF_3$, $R_2$=Cl, $R_3$=$R_4$=H, $R_5$=$CH_3$, $R_8$=H and m=1, the substituent $(R_{10})n$ is identical to the substituent shown in Table 9, and sequentially corresponds to 9-1 to 9-288 of Table 9, and the numbers of representative compounds are successively 18-1 to 18-288.

In the general formula I-1B,

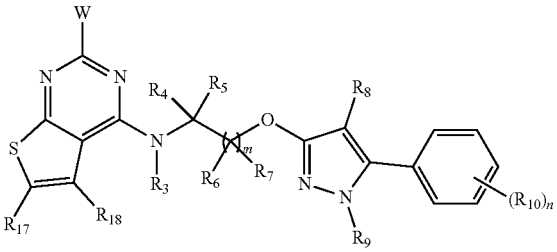

I-1B

Table 19: in the general formula I-1B, when $R_3$=$R_4$=$R_5$=H, $R_8$=H and m=1, the substituent $(R_{10})n$ is identical to the substituent shown in Table 9, and sequentially corresponds to 9-1 to 9-288 of Table 9, and the numbers of representative compounds are successively 19-1 to 19-288.

Table 19-1: in the general formula I-1B, when $R_3$=$R_4$=$R_5$=H, $R_8$=$CH_3$ and m=1, the substituent $(R_{10})n$ is identical to the substituent shown in Table 9, and sequentially corresponds to 9-1 to 9-288 of Table 9, and the numbers of representative compounds are successively 19-1-1 to 19-1-288.

Table 19-2: in the general formula I-1B, when $R_3$=$R_4$=$R_5$=H, $R_8$=H and m=2, the substituent $(R_{10})n$ is identical to the substituent shown in Table 9, and sequentially corresponds to 9-1 to 9-288 of Table 9, and the numbers of representative compounds are successively 19-2-1 to 19-2-288.

Table 19-3: in the general formula I-1B, when $R_3$=$R_4$=$R_5$=H, $R_8$=$CH_3$ and m=2, the substituent $(R_{10})n$ is identical to the substituent shown in Table 9, and sequentially corresponds to 9-1 to 9-288 of Table 9, and the numbers of representative compounds are successively 19-3-1 to 19-3-288.

Table 19-4: in the general formula I-1B, when $R_3$=$R_4$=H, $R_5$=$R_8$=$CH_3$ and m=1, the substituent $(R_{10})n$ is identical to the substituent shown in Table 9, and sequentially corresponds to 9-1 to 9-288 of Table 9, and the numbers of representative compounds are successively 19-4-1 to 19-4-288.

Table 20: in the general formula I-1B, when $R_3$=$R_4$=H, $R_5$=$CH_3$, $R_8$=H and m=1, the substituent $(R_{10})n$ is identical to the substituent shown in Table 9, and sequentially corresponds to 9-1 to 9-288 of Table 9, and the numbers of representative compounds are successively 20-1 to 20-288.

In the general formula I-1C,

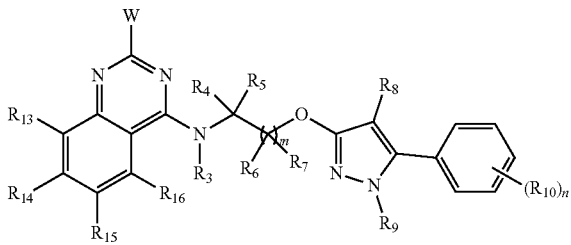

I-1C

Table 21: in the general formula I-1C, when $R_3$=$R_4$=$R_5$=H, $R_{18}$=Cl, $R_8$=H and m=1, the substituent $(R_{10})n$ is identical to the substituent shown in Table 9, and sequentially corresponds to 9-1 to 9-288 of Table 9, and the numbers of representative compounds are successively 21-1 to 21-288.

Table 21-1: in the general formula I-1C, when $R_3$=$R_4$=$R_5$=H, $R_{18}$=Cl, $R_8$=$CH_3$ and m=1, the substituent $(R_{10})n$ is identical to the substituent shown in Table 9, and sequentially corresponds to 9-1 to 9-288 of Table 9, and the numbers of representative compounds are successively 21-1-1 to 21-1-288.

Table 21-2: in the general formula I-1C, when $R_3$=$R_4$=$R_5$=H, $R_{18}$=Cl, $R_8$=H and m=2, the substituent $(R_{10})n$ is identical to the substituent shown in Table 9, and sequentially corresponds to 9-1 to 9-288 of Table 9, and the numbers of representative compounds are successively 21-2-1 to 21-2-288.

Table 21-3: in the general formula I-1C, when $R_3$=$R_4$=$R_5$=H, $R_{18}$=Cl, $R_8$=$CH_3$ and m=2, the substituent $(R_{10})n$ is identical to the substituent shown in Table 9, and sequentially corresponds to 9-1 to 9-288 of Table 9, and the numbers of representative compounds are successively 21-3-1 to 21-3-288.

Table 21-4: in the general formula I-1C, when $R_3$=$R_4$=H, $R_{18}$=Cl, $R_5$=$R_8$=$CH_3$ and m=1, the substituent $(R_{10})n$ is identical to the substituent shown in Table 9, and sequentially corresponds to 9-1 to 9-288 of Table 9, and the numbers of representative compounds are successively 21-4-1 to 21-4-288.

Table 22: in the general formula I-1C, when $R_3$=$R_4$=$R_5$=H, $R_{10}$=$CH_3$, $R_8$=H and m=1, the substituent $(R_{10})n$ is identical to the substituent shown in Table 9, and sequentially corresponds to 9-1 to 9-288 of Table 9, and the numbers of representative compounds are successively 22-1 to 22-288.

Table 23: in the general formula I-1C, when $R_3$=$R_4$=H, $R_5$=$CH_3$, $R_{18}$=Cl, $R_8$=H and m=1, the substituent $(R_{10})n$ is identical to the substituent shown in Table 9, and sequentially corresponds to 9-1 to 9-288 of Table 9, and the numbers of representative compounds are successively 23-1 to 23-288.

Table 24: in the general formula I-1C, when $R_3=R_4=H$, $R_5=CH_3$, $R_{18}=CH_3$, $R_8=H$ and m=1, the substituent $(R_{10})n$ is identical to the substituent shown in Table 9, and sequentially corresponds to 9-1 to 9-288 of Table 9, and the numbers of representative compounds are successively 24-1 to 24-288.

In the general formula I-1D,

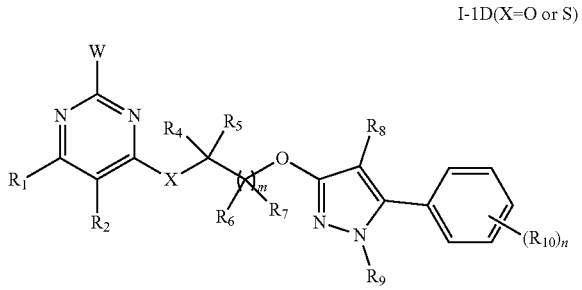

I-1D(X=O or S)

Table 25: in the general formula I-1D, when $R_1=CH_3$, $R_2=Cl$, $W=R_4=R_5H$, $X=O$, $R_8=H$ and m=1, the substituent $(R_{10})n$ is identical to the substituent shown in Table 9, and sequentially corresponds to 9-1 to 9-288 of Table 9, and the numbers of representative compounds are successively 25-1 to 25-288.

Table 26: in the general formula I-1D, when $R_1=C_2H_5$, $R_2=Cl$, $W=R_4=R_5=H$, $X=O$, $R_8=H$ and m=1, the substituent $(R_{10})n$ is identical to the substituent shown in Table 9, and sequentially corresponds to 9-1 to 9-288 of Table 9, and the numbers of representative compounds are successively 26-1 to 26-288.

Table 26-1: in the general formula I-1D, when $R_1=C_2H_5$, $R_2=Cl$, $W=R_4=R_5=H$, $X=O$, $R_8=CH_3$ and m=1, the substituent $(R_{10})n$ is identical to the substituent shown in Table 9, and sequentially corresponds to 9-1 to 9-288 of Table 9, and the numbers of representative compounds are successively 26-1-1 to 26-1-288.

Table 27: in the general formula I-1D, when $R_1=CHF2$, $R_2=Cl$, $W=R_4=R_5=H$, $X=O$, $R_8=H$ and m=1, the substituent $(R_{10})n$ is identical to the substituent shown in Table 9, and sequentially corresponds to 9-1 to 9-288 of Table 9, and the numbers of representative compounds are successively 27-1 to 27-288.

Table 28: in the general formula I-1D, when $R_1=CH_3$, $R_2=Cl$, $W=R_4=R_5=H$, $X=S$, $R_8=H$ and m=1, the substituent $(R_{10})n$ is identical to the substituent shown in Table 9, and sequentially corresponds to 9-1 to 9-288 of Table 9, and the numbers of representative compounds are successively 28-1 to 28-288.

Table 29: in the general formula I-1D, when $R_1=C_2H_5$, $R_2=Cl$, $W=R_4=R_5=H$, $X=S$, $R_8=Hl$ and m=1, the substituent $(R_{10})n$ is identical to the substituent shown in Table 9, and sequentially corresponds to 9-1 to 9-288 of Table 9, and the numbers of representative compounds are successively 29-1 to 29-288.

Table 30: in the general formula I-1D, when $R_1=CHF2$, $R_2=Cl$, $W=R_4=R_5=H$, $X=S$, R$=H and m=1, the substituent $(R_{10})n$ is identical to the substituent shown in Table 9, and sequentially corresponds to 9-1 to 9-288 of Table 9, and the numbers of representative compounds are successively 30-1 to 30-288.

In the general formula I-1A, when $R_1=CH_3$, $R_2=Cl$, $R_4=R_5=H$, $(R_{10})n=4-CH_3$, $R_8=H$ and m=1, the substituent $R_3$ (not hydrogen) is a different substituent as shown in Table 31, and the numbers of representative compounds are successively 31-1 to 31-140.

TABLE 31

| No. | R₃ | No. | R₃ | No. | R₃ | No. | R₃ |
|---|---|---|---|---|---|---|---|
| 31-1 | S-i-C₃H₇ | 31-2 | OH | 31-3 | —C(=O)H | 31-4 | CBr₃ |
| 31-5 | CH₃ | 31-6 | C₂H₅ | 31-7 | n-C₃H₇ | 31-8 | i-C₃H₇ |
| 31-9 | n-C₄H₉ | 31-10 | i-C₄H₉ | 31-11 | i-C₄H₉ | 31-12 | Cl₃ |
| 31-13 | CH₂Br | 31-14 | CHF₂ | 31-15 | CHBr₂ | 31-16 | CF₃ |
| 31-17 | CH₂Cl | 31-18 | CHCl₂ | 31-19 | CCl₃ | 31-20 | CH₂F |
| 31-21 | OCH₃ | 31-22 | OC₂H₅ | 31-23 | OCH(CH₃)₂ | 31-24 | OC(CH₃)₃ |
| 31-25 | OCF₃ | 31-26 | OCH₂CF₃ | 31-27 | OCHF₂ | 31-28 | OCHF₂ |
| 31-29 | SCH₃ | 31-30 | SC₂H₅ | 31-31 | SCH₂CH=CH₂ | 31-32 | CH=CH |
| 31-33 | CH₂CH=CH₂ | 31-34 | CH₂CH=CCl₂ | 31-35 | C=CH | 31-36 | CH₂C=CH |
| 31-37 | CH₂C=C-1 | 31-38 | CH₂OCH₃ | 31-39 | CH₂OCH₂CH₃ | 31-40 | CH₂CH₂OCH₃ |
| 31-41 | CH₂CH₂OCH₂Cl | 31-42 | CH₂OCH₂Cl | 31-43 | CH₂OCH₂OCH₃ | 31-44 | CH₂CH₂OCH₂Cl |
| 31-45 | CH₂SCH₃ | 31-46 | CH₂SCH₂CH₃ | 31-47 | CH₂CH₂SCH₃ | 31-48 | CH₂CH₂SCH₂CH₃ |
| 31-49 | CH₂SCH₂Cl | 31-50 | CH₂SCH₂CH₂Cl | 31-51 | CH₂CH₂SCH₂Cl | 31-52 | SOCH₃ |
| 31-53 | SOC₂H₅ | 31-54 | SOCF₃ | 31-55 | SOCH₂CF₃ | 31-56 | SO₂CH₃ |
| 31-57 | SO₂C₂H₅ | 31-58 | SO₂CF₃ | 31-59 | SO₂CH₂CF₃ | 31-60 | SO₂NHCOCH₃ |
| 31-61 | SO₂NHCH₃ | 31-62 | SO₂N(CH₃)₃ | 31-63 | CONHSO₂CH₃ | 31-64 | COCH₃ |
| 31-65 | COC₂H₅ | 31-66 | CO-n-C₃H₇ | 31-67 | CO-i-C₃H₇ | 31-68 | CO-n-C₄H₉ |
| 31-69 | CO-i-C₄H₉ | 31-70 | CO-t-C₄H₉ | 31-71 | COCH₂Cl | 31-72 | COCH₂Cl |
| 31-73 | COOCH₃ | 31-74 | COOC₂H₅ | 31-75 | COO-N-C₃H₇ | 31-76 | COO-t-C₄H₉ |
| 31-77 | COOCF₃ | 31-78 | COOCH₂CH₂Cl | 31-79 | COOCH₂CF₃ | 31-80 | CH₂COOCH₃ |
| 31-81 | CH₂COOC₂H₅ | 31-82 | CH₂COCH₃ | 31-83 | CH₂COC₂H₅ | 31-84 | CONHCH₃ |
| 31-85 | CONHC₂H₅ | 31-86 | CONH-t-C₄H₉ | 31-87 | CON(CH₃)₂ | 31-88 | CON(C₂H₅)₂ |
| 31-89 | COOCH₂CH=CH₂ | 31-90 | CH₂CH=CH₂ | 31-91 | COOCH₂OCH₃ | 31-92 | COOCH₂CH₂OCH₃ |
| 31-93 | SNHCH₃ | 31-94 | SNHC₂H₅ | 31-95 | SN(CH₃)₂ | 31-96 | SN(C₂H₅)₂ |
| 31-97 | | 31-98 | | 31-99 | | 31-100 | |

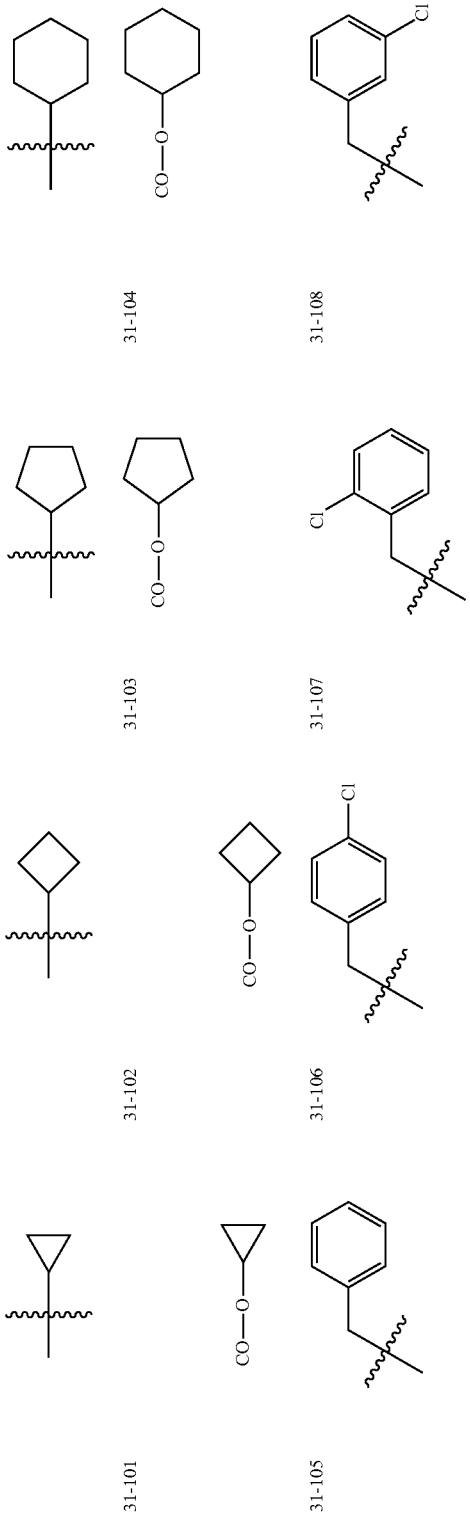

TABLE 31-continued

| No. | R₃ | No. | R₃ | No. | R₃ | No. | R₃ |
|---|---|---|---|---|---|---|---|
| 31-109 | 4-CF₃-benzyl (CH₂ with methyl) | 31-110 | 2,4-dimethyl-benzyl | 31-111 | 2,4-dichloro-benzyl | 31-112 | 2-Cl-4-CF₃-benzyl |
| 31-113 | 2,6-dichloro-4-CF₃-benzyl | 31-114 | 2-chloropyridin-5-yl-methyl | 31-115 | 5-chlorothiazol-2-yl-methyl | 31-116 | 5-chlorothiophen-2-yl-methyl |
| 31-117 | phenyl-CH(CH₃)CH₂- | 31-118 | 4-Cl-phenyl-CH(CH₃)CH₂- | 31-119 | phenyl-O- | 31-120 | 4-CH₃-phenyl-O- |
| 31-121 | 4-NO₂-phenyl-O- | 31-122 | 4-CF₃-phenyl-O- | 31-123 | 4-Cl-phenyl-O- | 31-124 | phenyl-O-CO- |
| 31-125 | 4-CH₃-phenyl-O-CO- | 31-126 | 4-CF₃-phenyl-O-CO- | 31-127 | 4-Cl-phenyl-O-CO- | 31-128 | 4-NO₂-phenyl-O-CO- |
| 31-129 | benzyl-O-CO- | 31-130 | 4-CH₃-benzyl-O-CO- | 31-131 | 6-chloropyridin-3-yl-methyl-O-CO- | 31-132 | 4-CF₃-benzyl-O-CO- |

TABLE 31-continued

| No. | R₃ | No. | R₃ | No. | R₃ | No. | R₃ |
|---|---|---|---|---|---|---|---|
| 31-133 | 4-NO₂-C₆H₄-CH₂-O-CO- | 31-134 | 4-OCH₃-C₆H₄-CH₂-O-CO- | 31-135 | PhC(O)CH₂C(CH₃)- | 31-136 | 4-CH₃-C₆H₄-C(O)CH₂C(CH₃)- |
| 31-137 | 4-Cl-C₆H₄-C(O)CH₂C(CH₃)- | 31-138 | 4-Br-C₆H₄-C(O)CH₂C(CH₃)- | 31-139 | PhC(O)CH₂CH₂C(CH₃)- | 31-140 | 4-Cl-C₆H₄-C(O)CH₂CH₂C(CH₃)- |

The salt of part of compounds in the present invention can be illustrated by the salt of specific compounds listed in Table 32, but not to limit the present invention.
TABLE 32
Salt of Part of Compounds
| No. | structure |
|---|---|
| 32-1 | 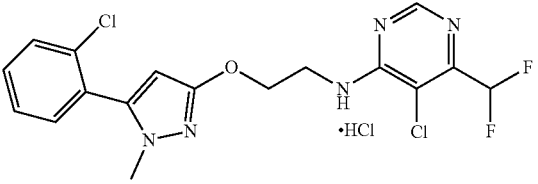 [SMILES: Cn1nc(OCCNc2ncnc(C(F)F)c2Cl)cc1-c1ccccc1Cl ; Cl] |
| 32-2 | 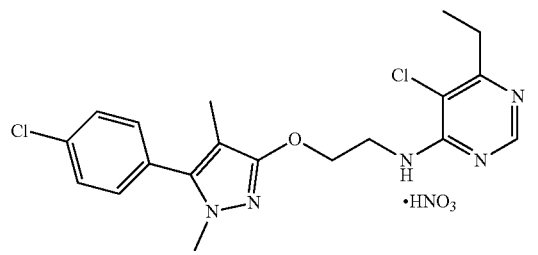 |
| 32-3 | 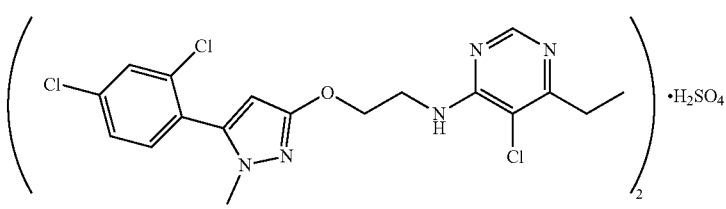 |
| 32-4 | 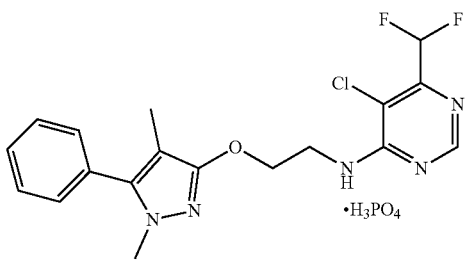 |
| 32-5 | 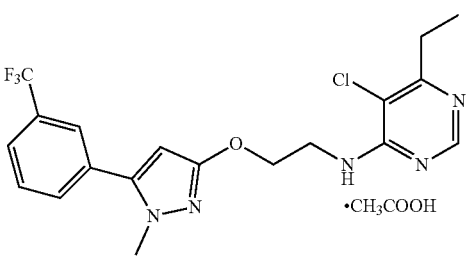 |
| 32-6 | 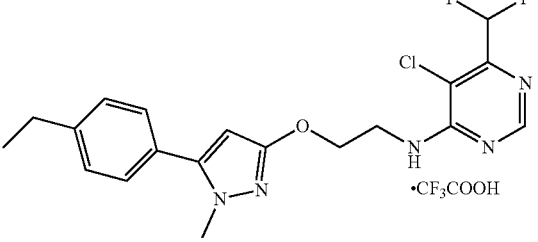 |

TABLE 32-continued
Salt of Part of Compounds
| No. | structure |
|---|---|
| 32-7 | 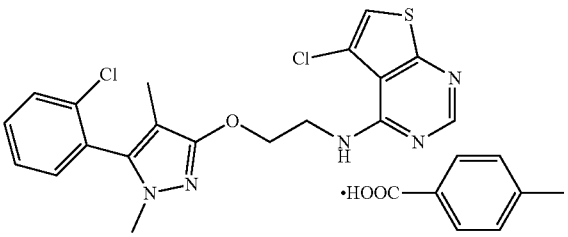 |
| 32-8 | 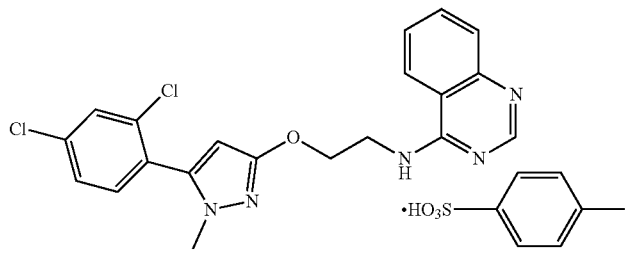 |
| 32-9 | 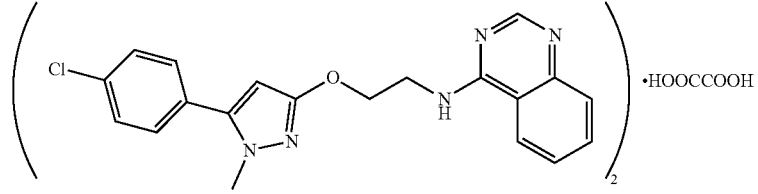 |
| 32-10 | 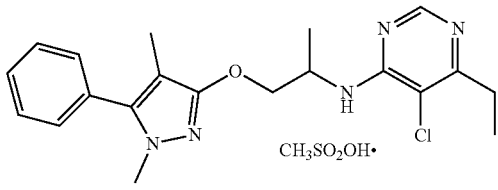 |
| 32-11 | 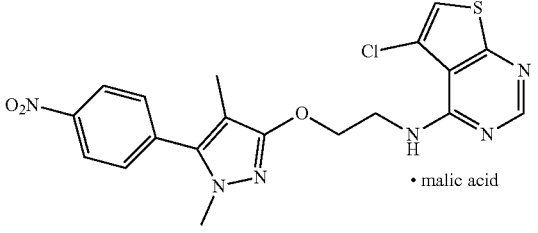 |
| 32-12 | 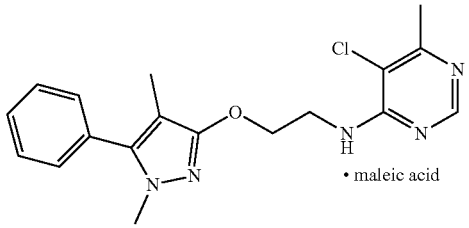 |

TABLE 32-continued

Salt of Part of Compounds

| No. | structure |
|---|---|
| 32-13 | 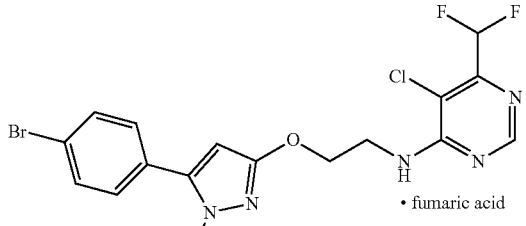 • fumaric acid |
| 32-14 | 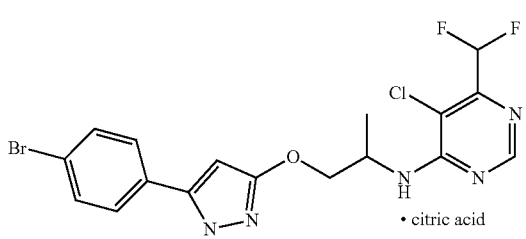 • citric acid |

The compound of the present invention is prepared by the following method. Reaction formulas are as follows. Unless otherwise stated, the definitions of the groups in the formulas are the same as above:

The preparation method of the compound of the general formula I is as follows:

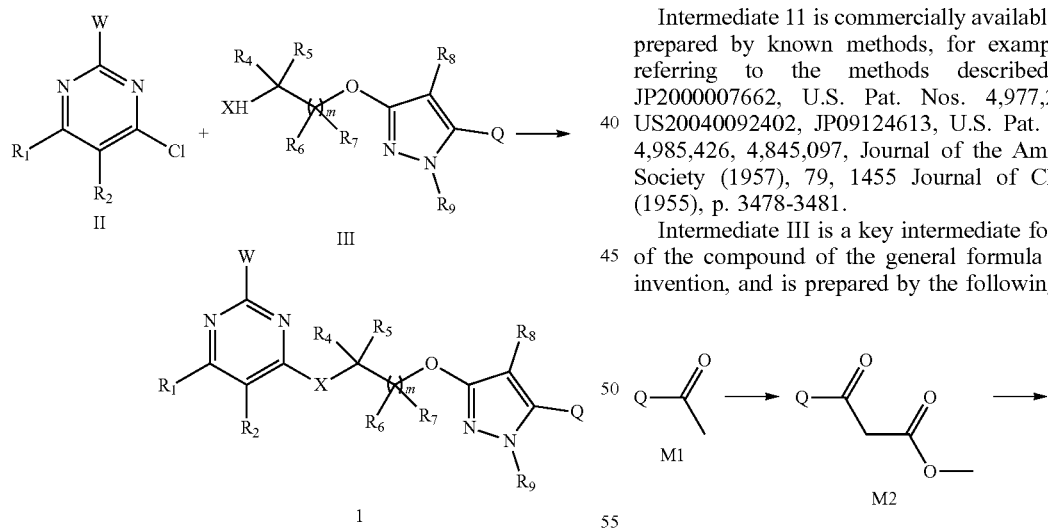

Intermediates 11 and 111 react in a suitable solvent under alkaline conditions to obtain the compound of the general formula I.

Proper alkali may be selected from, for example, potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide.

The reaction is conducted in the proper solvent which can be selected from, for example, tetrahydrofuran, 1,4-dioxane, acetonitrile, toluene, xylene, benzene, N,N-dimethylformamide, N-methylpyrrolidone, dimethylsulfoxide, acetone or butanone.

The reaction temperature can be between room temperature and the boiling point temperature of the solvent, generally 20-100° C.

The reaction time is 30 minutes to 20 hours, generally 1-10 hours.

Intermediate 11 is commercially available and can also be prepared by known methods, for example, prepared by referring to the methods described in literature JP2000007662, U.S. Pat. Nos. 4,977,264, 6,090,815, US20040092402, JP09124613, U.S. Pat. Nos. 5,468,751, 4,985,426, 4,845,097, Journal of the American Chemical Society (1957), 79, 1455 Journal of Chemical Society (1955), p. 3478-3481.

Intermediate III is a key intermediate for the preparation of the compound of the general formula I in the present invention, and is prepared by the following method:

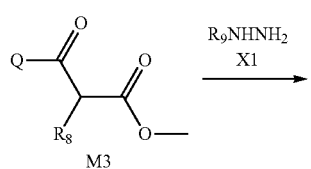

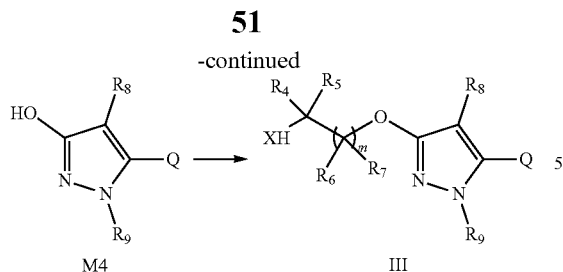

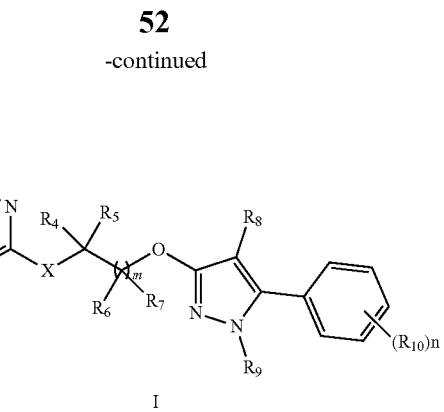

Intermediate M1 and dimethyl carbonate react in a suitable solvent at suitable temperature for 30 minutes to 20 hours, generally 1-10 hours, to obtain intermediate M2. Refer to Tetrahedron: Asymmetry, 24(15-16), 925-936; 2013 and Angewandte Chemie, International Edition, 53(45), 12210-12213; 2014 for the operation method of this step. M2 generates an electrophilic substitution reaction to obtain M3. Refer to Pest Management science, 66(1),2010,107-112 for the operation method of this step. M3 reacts with X1 to prepare M4. Refer to Pest Management science, 66(1),2010, 107-112 for the operation method of this step. Finally, M4 reacts with the corresponding halogenide to prepare III. Refer to US20100158860, WO2011133444 and Bioorganic & Medicinal Chemistry, 20(20), 6109-6122, 2012 for the operation method of this step.

Further, the preparation method of the general formula compound I-1 is as follows: refer to corresponding steps and related reference literature of preparation of the compound of the general formula I for specific reaction conditions of the steps.

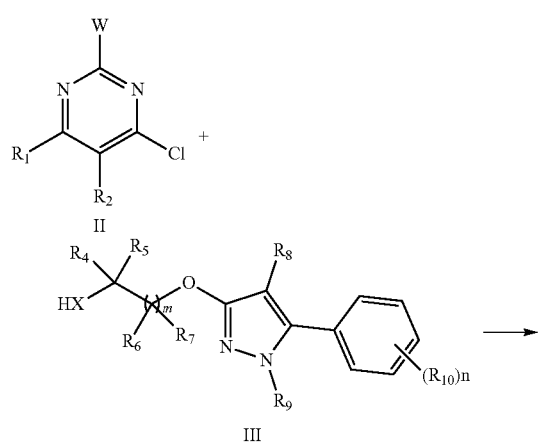

Intermediates II and III react in a suitable solvent under alkaline conditions to obtain the compound of the general formula I-1.

Proper alkali may be selected from, for example, potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide.

The reaction is conducted in the proper solvent which can be selected from, for example, tetrahydrofuran, 1,4-dioxane, acetonitrile, toluene, xylene, benzene, N,N-dimethylformamide, N-methylpyrrolidone, dimethylsulfoxide, acetone or butanone.

The reaction temperature can be between room temperature and the boiling point temperature of the solvent, generally 20-100° C.

The reaction time is 30 minutes to 20 hours, generally 1-10 hours.

Intermediate II is commercially available and can also be prepared by known methods, for example, prepared by referring to the methods described in literature JP2000007662. U.S. Pat. Nos. 4,977,264, 6,090,815, US20040092402, JP09124613, U.S. Pat. Nos. 5,468,751, 4,985,426, 4,845,097, Journal of the American Chemical Society (1957), 79, 1455 Journal of Chemical Society (1955), p. 3478-3481.

Intermediate III is a key intermediate for the preparation of the compound of the general formula I-1 in the present invention, and is prepared by the following method:

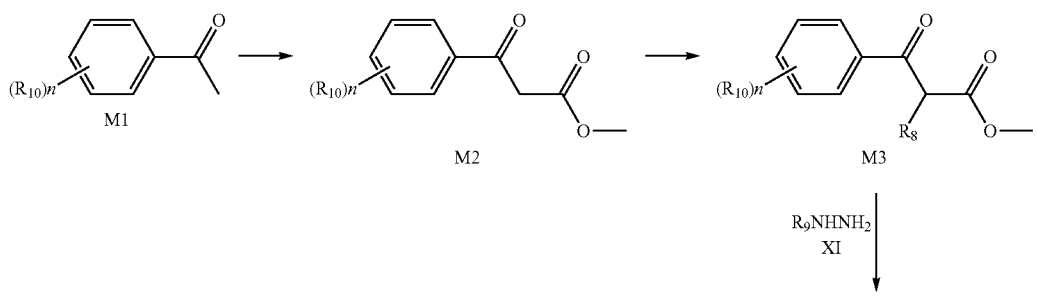

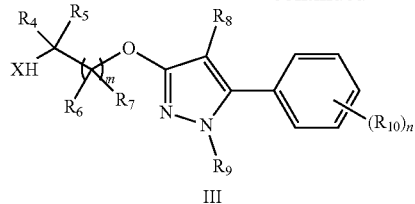
III

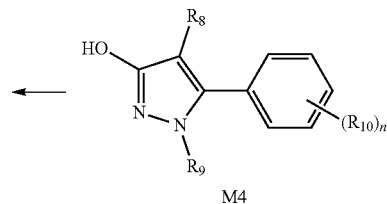
M4

Intermediate M1 and dimethyl carbonate react in a suitable solvent at suitable temperature for 30 minutes to 20 hours, generally 1-10 hours, to obtain intermediate M2. Refer to Tetrahedron: Asymmetry, 24(15-16), 925-936; 2013 and Angewandte Chemie, International Edition, 53(45), 12210-12213; 2014 for the operation method of this step. M2 generates an electrophilic substitution reaction to obtain M3. Refer to Pest Management science, 66(1),2010,107-112 for the operation method of this step. M3 reacts with X1 to prepare M4. Refer to CN102584705A for the operation method of this step. Finally, M4 reacts with the corresponding halogenide to prepare III. Refer to US20100158860, WO201133444 and Bioorganic & Medicinal Chemistry, 20(20), 6109-6122, 2012 for the operation method of this step.

Although the compound of the general formula I of the present invention and some compounds disclosed in the prior art also belong to pyrimidine-containing substituted pyrazole compounds, the structural features are still obviously different. Moreover, due to the structural differences, the compound of the present invention has better fungicidal, insecticidal and acaricidal activity.

The compound of the general formula I shows excellent activity against various fungi in agriculture or other fields, and also shows good activity against pests and mites. Therefore, the technical solution of the present invention also comprises the use of the compound of the general formula I as a fungicide, an insecticide and an acaricide in agriculture or other fields.

The examples of the diseases mentioned below are only used to explain the present invention, but not to limit the present invention.

The compound of the general formula I can be used for controlling the following diseases: oomycete diseases such as downy mildew (cucumber downy mildew, canola downy mildew, soybean downy mildew, beet downy mildew, sugar cane downy mildew, tobacco downy mildew, pea downy mildew, loofah downy mildew, winter melon downy mildew, melon downy mildew, cabbage downy mildew, spinach downy mildew, radish downy mildew, grape downy mildew and onion downy mildew), albugo candida (oilseed rape white rust and cabbage white rust), damping-off (oilseed rape damping-off, tobacco damping-off, tomato damping-off, pepper damping-off, eggplant damping-off, cucumber damping-off and cotton damping-off), pythium rot (chilli pythium rot, loofah pythium rot and winter melon pythium rot), blight (broad bean blight, cucumber blight, pumpkin blight, winter melon blight, watermelon blight, melon blight, pepper blight, leek blight, garlic blight and cotton blight), late blight (potato late blight and tomato late blight); fungi imperfecti diseases such as fusarium wilt (sweet potato wilt, cotton wilt, sesame wilt, castor wilt, tomato wilt, bean wilt, cucumber wilt, loofah wilt, pumpkin wilt, winter melon wilt, watermelon wilt, melon wilt, pepper wilt, broad bean wilt, rape wilt and soybean wilt), root rot (pepper root rot, eggplant root rot, bean root rot, cucumber root rot, bitter gourd root rot, cotton black root rot and broad bean root rot), wilt disease (cotton wilt disease, sesame wilt disease, pepper wilt disease, cucumber wilt disease and cabbage wilt disease), anthrax (sorghum anthrax, cotton anthrax, kenaf anthrax, jute anthrax, flax anthrax, tobacco anthrax, mulberry anthrax, pepper anthrax eggplant anthrax, bean anthrax, cucumber anthrax, bitter gourd anthrax, zucchini anthrax, winter melon anthrax, watermelon anthrax, melon anthrax and litchi anthrax), greensickness (cotton greensickness, sunflower greensickness, tomato greensickness, pepper greensickness and eggplant greensickness), scab (squash scab, winter melon scab and melon scab), *Botrytis cinerea* (cotton boll *Botrytis cinerea*, kennel *Botrytis cinerea*, tomato *Botrytis cinerea*, pepper *Botrytis cinerea*, bean *Botrytis cinerea*, celery *Botrytis cinerea*, spinach *Botrytis cinerea* and kiwi *Botrytis cinerea*), brown spot (cotton brown spot, jute brown spot, beet brown spot, peanut brown spot, pepper brown spot, winter melon brown spot, soybean brown spot, sunflower brown spot, pea brown spot and broad bean brown spot), black spot (flax false black spot, canola black spot, sesame black spot, sunflower black spot, castor black spot, tomato black spot, pepper black spot, eggplant black spot, bean black spot, cucumber black spot, celery black spot, carrot black rot, carrot black spot, apple black spot and peanut black spot), spot blight (tomato spot blight, pepper spot blight and celery spot blight), early blight (tomato early blight, pepper early blight, eggplant early blight, potato early blight and celery early blight), ring spot (soybean ring spot, sesame ring spot and bean ring spot), leaf blight (sesame leaf blight, sunflower leaf blight, watermelon leaf blight and melon leaf blight), stem rot (tomato stem rot and bean stem rot), and others (maize round spot, kenaf dropping disease, rice blast disease, foxtail millet black sheath, sugarcane eye spot, cotton boll aspergillosis, peanut crown rot, soybean stem blight, soybean black spot, melon leaf spot, peanut net blotch, tea red leaf spot, *capsicum* blight, winter melon leaf spot, celery black rot, spinach heart rot, kenaf leaf mold, kenaf spot, jute stem spot, soybean purple spot, sesame leaf spot, *ricinus* gray leaf spot, dark brown leaf spot, eggplant *cercospora* leaf spot, bean southern blight, bitter gourd white spot, watermelon spot, jute blight rot, sunflower rhizome rot, bean char rot, soybean target spot, eggplant stick leaf spot, cucumber target spot, tomato leaf mold, eggplant leaf mold and broad bean chocolate spot); basidiomycete diseases such as rust (wheat stripe rust, wheat straw rust, wheat leaf rust, peanut rust, sunflower rust, sugar cane rust, leek rust, onion rust, chestnut rust and soybean rust), smut (maize head smut, corn smut, sorghum head smut, sorghum loose smut, sorghum covered kernel smut, sorghum stem smut, chestnut smut, sugar cane smut and bean rust) and others (such as wheat sheath blight and rice sheath blight disease, etc.); ascomycete diseases such as powdery mildew (wheat powdery mildew, rape powdery mildew, sesame powdery mildew, sunflower powdery mildew, sugar beet powdery mildew, eggplant powdery mildew, pea powdery mildew, loofah powdery mildew, pumpkin powdery mildew, zucchini powdery mildew, winter melon powdery mildew, melon powdery mildew, grape powdery mildew and broad bean powdery mildew), *sclerotinia* (flax *sclerotinia*, rape *sclerotinia*, soybean *sclerotinia*, peanut *sclerotinia*, tobacco *sclerotinia*, capsicum *sclerotinia*, eggplant *sclerotinia*, bean *sclerotinia*, pea *sclerotinia*, cucumber *sclerotinia*, bitter gourd *sclerotiorum*, winter melon *sclerotinia*, watermelon *sclerotinia* and celery *sclerotinia*), scab (apple scab and pear scab), etc.

The compound shown by the general formula I can be used for controlling the following pests and mites:

Coleoptera (beetle): *acanthoscelides* spp. (curculionid), *Acanthoscelides obtectus* (common *Bruchus pisorum*), *Agrilus planipennis*, *agriotes* spp. (wireworm), *Anoplophora glabripennis* (Asian psacotheahilaris), *anthonomus* spp. (curculionidae), *Anthonomus grandis* (cotton bollworm), *aphidius* spp., *apion* spp. (curculionid), *apogonia* spp. (grub), *Atacnius spretulus* (*Maladera orientalis*), *Atomaria linearis* (pygmy mangold beetle), *aulacophore* spp., *Bothynoderes punctiventris* (beetroot weevil), *bruchus* spp. (curculionid), *Bruchus pisorum* (pea weevil), *cacoesia* (*cacoesia* spp.), *Callosobruchus maculatus* (southern cowpea weevil), *Carpophilus hemipteras* (dried-frait beetle), *Cassida vittata*, *cerosterna* spp., *cerotoma* (*cecrotoma* spp.) (chrysomcids), *Cerotoma trifur cata* (bean leaf beetle), *ceutorhynchus* spp. (curculionid), *Ceutorhynchus assimilis* (cabbage seedpod weevil), *Ceutorhynchus napi* (cabbage *curculio*), *chaetocnema* spp. (chrysomonad), *colaspis* (*colaspis* spp.) (soil beetle), *Conoderus scalaris*, *Conoderus stigmosus*, *Conotrachelus nenuphar* (plum *curculio*), *Cotinus nitidis* (green June beetle), *Crioceris asparagi* (asparagus beetle), *Cryptolestes ferrugincus* (rusty grainbeetle), *Cryptolestes pusillus* (laemophloeidae), *Cryptolestes turcicus* (turkish grain beetle), *ctenicera* (*ctenicera* spp.) (nematode), *curculio* spp. (curculionid), *cyclocephala* spp. (grub), *Cylindroepturus adspersus* (sunflower stem weevil), *Deporaus marginatus* (mango leaf-cutting weevil), *Dermestes lardarius*, *Dermestes maculates*, *diabrotica* spp. (leaf beetle), *Epilachna varivcstis* (Mexican bean beetle), *Raustinus cubae*, *Hylobius pales* (*pales* weevil), *hypera* spp. (curculionid), *Hypera postica*, *hyperdoes* (*hyperdoes* spp.) (hyperodes weevil), *Hypothenemus hampei* (coffee fruit beetle), *ips* spp. (engravers), *Lasioderma serricome* (cigarette beetle), *Leptinotarsa decemlineata* (Colorado potato beetle), *Liogenys fuscus*, *Liogenys suturalis*, *Lissorhoptrus oryzophilus*, *lyctus* spp. (powder post beetles), *Maecolaspis joliveti*, *megascelis* (*megascelis* spp.), *Melanotus communis*, *meligethes* spp., *Meligethes aeneus* (blossom beetle), *Melolontha melolontha* (common European chafer), *Oberea brevis*, *Oberea linearis*, *Oryctes rhinoceros* (date palm beetle), *Oryzaephilus mercator* (merchant grain beetle), *Oryzaephilus surinamensis* (sawtoothed grain beetle), *otiorhynchus* spp. (curculionid), *Oulema melanopus* (cereal leafbeetle), *Oulema oryzae*, *pantomorus* spp. (curculionid), *phyllophaga* spp. (*Melolontha melolontha*/June scarabaeidae), *Phyllophaga cuyabana*, *phyllotreta* spp. (chrysomonad), *phynchites* spp., *Popillia japonica* (Japanese chafer), *Prostephanus truncates* (larger grain borer), *Rhizopertha dominica* (lesser grain borer), *rhizotrogus* spp. (Europoean chafer), *rhynchophorus* spp. (curculionid), *scolytus* spp. (wood moth), *shenophorus* (*shenophorus* spp.) (granary weevil), *Sitona lincatus* (pea leaf weevil), *sitophilus* spp. (valley weevil), *Sitophilus granaries* (granary weevil), *Sitophilus oryzae* (rice weevil), *Stegobium paniceum* (drugstore beetle), *tribolium* spp. (*Tenebrio molitor*), *Tribolium castaneum* (red flour beetle), *Tribolium confusum* (confused flour beetle), *Trogoderma variabile* (warehouse beetle) and *Zabrus tenebioides*.

Dermaptera (earwig).

Dictyoptera (cockroach): *Blattella germanica* (German cockroach), *Blatta orientalis*)(oriental cockroach), *Parcoblatta pennylvanica*, *Periplaneta americana* (American cockroach), *Periplaneta australoasiae* (Australian cockroach), *Periplancta brunnca* (brown cockroach), *Periplaneta fuliginosa* (smokybrown cockroach), *Pyncoselus suninamensis* (surinam cockroach) and *Supella longipalpa* (brownbanded cockroach).

Diptera)(fly): *aedes* spp. (mosquito), *Agromyza frontella* (alfalfa blotch leafminer), *agromyza* spp. (leaf miner), *anastrepha* spp. (fruit fly), *Anastrepha suspensa* (Caribbean fruit fly), *anopheles* spp. (mosquito), *batrocera* spp. (fruit fly), *Bactrocera cucurbitae* (melon fly), *Bactrocera dorsalis* (oriental fruit fly), *ceratitis* spp. (fruit fly), *Ceratitis capitata* (mediterranean fruit fly), *chrysops* spp. (deerfly), *cochliomyia* spp. (screw worm fly larva), *contarinia* spp. (midge), *culex* spp. (mosquito), *dasineura* spp. (midge), *Dasineura brassicae* (cabbage midge), *delia* spp., *Delia platura* (seedcorn maggot), *drosophila* spp. (vinegar fly), *fannia* spp. (housefly), *Fannia canicularis* (little house fly), *fannia scalaris* (latrine fly), *Gasterophilus intestinalis* (nit fly), *Gracillia perseae*, *Haematobia irritans* (horn fly), *hylemyia* spp. (root maggot), *Hypoderma lineatum* (common cattle grub), *liriomyza* spp. (leaf miner), *Liriomyza brassica* (serpentine leafminer), *Melophagus ovinus* (sheep ked), *musca* spp. (muscid fly), *Musca autumnalis* (face fly), *Vusca domestica* (house fly), *Oestrus ovis* (sheep bot fly), *Oscinella frit* (Sweden wheat stem maggot), *Pegomyia betae* (beet leafminer), *phorbia* spp., *Psila rosae* (carrotrust fly), *Rhagoletis cerasi* (cherry fruit fly), *Rhagoletis pomonella* (apple maggot), *Sitodiplosis mosellana* (orange wheat blossom midge), *Stomoxys calcitruns* (stable fly), *tahanus* spp. (horse botfly) and *tipula* spp. (daddy-longlegs).

Hemiptera (stink bug), *Acrosternum hilare* (green stink bug), *Blissus leucopterus* (chinch bug), *Calocoris norvegicus* (potato mirid), *Cimex hemipterus* (tropical bed bug), *Cimex lectularius* (bed hug), *Daghertus fasciatus*, *Dichelops furcatus*, *Dysdercus suturellus* (cotton stainer), *Edessa meditabunda*, *Eurygaster maura* (cereal bug), *Euschistus heros*, *Euschistus servus* (brown stink bug), *Helopeltis antonii*, *Helopeltis theivora* (tea blight plantbug), *lagynotomus* spp. (stink bug), *Leptocorisa oratorius*, *Leptocorisa varicornis*, *lygus* spp. (plant bug), *Lygus hesperus* (western tarnished plant bug), *Maconellicoccus hirsutus*, *Neurocolpus longirostris*, *Nezara viridula* (southern green stink bug), *PhyLocoris* spp. (fleahopper), *Phytocoris californicus*, *Phytocoris relativus*, *Piezodorus guildingi*, *Poecilocapsus lineatus* (fourlined plant bug), *Psallus vaccinicola*, *Pseudacysta perseae*, *Scaptocoris castanea* and *triatoma* spp. (bloodsuckingconenose bug/kissing bug).

Homoptera (aphid, scale insect, whitefly and leafhopper): *acrythosiphonpisum* (pea aphid), *adelges* spp. (adelgids), *Aleurodes proletella* (cabbage whitefly), *Aleurodicus disperses*, *Aleurothrixus flccosus* (woolly whitefly), *aluacaspis* spp., *Amrasca bigutella bigutella*, *aphrophora* spp. (leafhopper), *Aonidiella aurantii* (California red scale), *aphis* spp. (aphid), *Aphis gossypii* (cotton aphid), *Aphis pomi* (apple aphid), *Aulacorthitm solani* (foxglove aphid), *bemisia* spp. (whitefly), *Bemisia argentifolii*, *Bemisia tabaci* (sweetpotato whitefly), *Brachycolus noxius* (Russian aphid), *Brachycorynclia asparagi* (asparagus aphid), *Brevennia rehi*, *Brevicoryne brassicae* (cabbage aphid), *ceroplastes* spp. (scale insect), *Ceroplastes rubens* (red wax scale), *chionaspis* spp. (scale insect), *chrysomphalus* spp. (scale insect), *coccus* spp. (scale insect), *Dysaphis plantaginea* (rosy apple aphid), *empoasca* spp. (leafhopper), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata*, *Metopolophium dirhodum* (rose grain aphid), *Midis longicornis*, *Myzus persicae* (green peach aphid), *Nephotettix* spp. (leafhopper), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *philaenus* spp. (spittle insect), *Phylloxera vitifoliae* (grape *phylloxera*), *Physokermes piceae* (spruce bud scale), *planococcus* spp. (mealybug), *pseudococcus* spp. (mealybug), *Pseudococcus brevipes* (pine apple mealybug), *Quadraspidiotus perniciosus* (san Jose scale), *Rhapalosiphum* spp. (aphid), *Rhapalosiphum maida* (corn leaf aphid), *Rhapalosiphum padi* (oat-bird-cherry aphid), *saissetia* spp. (scale insect), *Saissetia oleae* (black scale insect), *Schizaphis graminum* (greenbug), *Sitobion avenge* (English wheat aphid), *Sogatella furcifera* (white-backed planthopper), *therioaphis* spp. (aphid), *toumeyella* spp. (scale insect), *toxoptera* spp. (aphid), *trialeurodes* spp. (whitefly), *Trialeurodes vaporariorum* (greenhouse whitefly), *Trialeurodes abutiloneus* (banded-wing whitefly), *unaspis* spp. (scale insect), *Unaspis yanonensis* (arrowhead scale) and *Zulia entreriana*.

Hymenoptera (ant, wasp and bee): *acromyrrmex* spp., *Athalia rosae*, *atta* spp. (leafcutting ants), *camponotus* spp. (carpenter ant), *diprion* spp. (sawfly), *formica* spp. (ant), *Iridomyrmex humilis* (argentineant), *monomorium* ssp., *Monomorium minumum* (little black ant), *Monomorium pharaonis* (pharaoh ant), *neodiprion* spp. (sawfly), *pogonomyrmex* spp. (harvest ant), *polistes* spp. (paper wasp), *solenopsis* spp. (fire ant), *Tapoinoma sessile* (odorous house ant), *tetranomorium* spp. (pavement ant), *vespula* spp. (yellow jacket) and *xylocopa* spp. (carpenter bee).

Isoptera (termite): *coptotcrmcs* spp., *Coptotermes curvignathus*, *Coptotermes frenchii*, *Coptotermes formosanus* (formosan subterranean termite), *cornitermes* spp. (nasute termite), *cryptotermes* spp. (dry wood termite), *heterotermes* spp. (desert subterranean termite), *Ieterotermes aureus*, *kalotermes* spp. (dry wood termite), *incistitermes* spp. (dry wood termite), *macrotermes* spp. (fungus growing termite), *marginitermes* spp. (dry wood termite), *microcerotermes* spp. (harvester termite), *Microtermes obesi*, *procornitermes* spp., *reticulitermes* spp. (limicolous termite), *Reticulitermes banyulensis*, *Reticulitermes grassei*, *Reticulitermes flavipes* (eastern limicolous termite), *Reticulitermes hageni*, *Reticulitermes hesperus* (western limicolous termite), *Reticulitermes santonensis*, *Reticulitermes speratus*, *Reticulitermes tibialis*, *Reticulitermes virginicus*, *schedorhinotermes* spp. and *zootermopsis* spp. (rottenwood termite).

Lepidoptera (moth and butterfly): *Achoea janata*, *adoxophyes* spp., *Adoxophyes orana*, *agrotis* spp. (wireworm), *Agrotis ipsilon* (black wireworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulijera* (jute looper), *Anticarsia gemmatalis* (velvetbean caterpillar), *Archips argyrospila* (fruit tree leafroller), *Archips rosana* (rose leaf roller), *argyrotaenia* spp. (tortricid moths), *Argyrotaenia citrana* (orange tortrix), *Autographa gamma*, *Bonagota cranaodcs*, *Borbo cinnara* (rice leaf folder), *Bucculatrix thurberiella* (cotton leafperforator), *caloptilia* spp. (leaf miner), *Capua reticulana*, *Carposina niponensis* (peach fruit moth), *chilo* spp., *Chlumetia transversa* (mango shoot borer), *Choristoneura rosaceana* (oblique banded leaf roller), *chrysodeixis* spp., *Enaphalocerus medinalis* (grass leafroller), *colias* spp., *Conpomorpha cramerella*, *Cossus cossus* (wood stupid moths), *crambus* spp. (sod webworms), *Cydia funebrana* (plum fruit moth), *Cydia molesta* (oriental fruit moth), *Cydia nignicana* (pea moth), *Cydia pomonella* (codling moth), *Darna diducta*, *diaphania* spp. (stem borer), *diatraea* spp. (stalk bor er), *diatraea saccharalis* (sugarcane borer), *Diatraea graniosella* (southwester corn borer), *earias* spp. (cotton bollworm), *Earias insulata* (Egyptian bollworm), *Earias vit.ella* (rough northern bollworm), *Ecdytopopha aurantianum*, *Elasmopalpus lignosellus* (lesser cornstalk borer), *Epiphysias postruttana* (light brown apple moth), *ephestia* spp. (pink moth), *Ephestia cautella* (almond moth), *Ephestia elutella* (tobbaco moth), *Ephestia kuehniella* (mediterranean flour moth), *epimeces* spp., *Epinotia aporema*, *Erionota thrax* (banana skipper), *Eupoecilia ambiguella* (grape berry moth), *Euxoa auxiliaris* (army cutworm), *feltia* spp. (wireworm), *gortyna* spp. (stem borer), *Grapholita molesta* (peach(apricot)(oriental fruit moth), *Hedylepta indicata* (bean leaf webber), *Helicoverpa* spp. (noctuid), *Helicoverpa armigera* (cotton bollworm), *Helicoverpa zea* (corn borer(moth/cotton bollworm)), *heliothis* spp. (noctuid), *Heliothis virescens* (tobacco budworm), *Hellula undalis* (cabbage webworm), *indarbla* spp. (root moth), *Keiferia lycopersicella* (tomato pinworm), *Leucinodes orbonalis* (eggplant fruit borer), *Leucoptera malifoliella*, *lithocollectis* spp., *Lobesia botrana* (grape fruit moth), *loxagrotis* spp. (noctuid), *Loxagrotis albicosta* (western bean cutworm), *Lymantria dispar* (gypsy moth), *lyonetiaclerkella*)(apple leafminer), *mahasena corbetti* (oil palm bagworm), *malacosoma* spp. (tent caterpillars), *Mamestra brassicae* (cabbage armyworm), *Maruca testulalis* (Maruca vitrata), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia*, *Pandemis cerasana* (common currant tortrix), *Pandemis heparana* (brown apple tortrix), *Papilio demodocus*, *Pectinophora gossypiella* (pink bollworm), *peridroma* spp. (wireworm), *Peridroma saucia* (variegated cutworm), *Perileucoptera coffeella* (white coffee leafminer), *Phthorimaea operculella* (potato tuber moth), *Phyllocnisitis citrella*, *phyllonorycter* spp. (leaf miner), *Pieris rapae* (imported cabbageworm), *Plathypena scabra*, *Plodia interpunctella* (Indian meal moth), *Plutella xylostella* (diamondback moth), *Polychrosis viteana* (grape berry moth), *Prays endocarps*, *Prsys oleae* (olive moth), *pseudaletia* spp. (noctuid), *Pseudaletia unipunctata* (armyworm), *Pseudoplusia includens* (soybean looper), *Rachiplusia nu*, *Scirpophaga incertulas*, *sesamia* spp. (stem borer), *Sesamia inferens* (pink rice stemborer), *Sesamia nonagrioides*, *Setora nitens*, *Sitotroga cerealella* (angoumois grain moth), *Sparganothis pilleriana*, *spodoptera* spp. (armyworm), *Spodoptera exigua* (beet armyworm), *Spodoptera fugiperda* (fall armyworm), *Spodoptera oridania* (southern armyworm), *synanthedon* spp. (root moth), *Thecla basilides*, *Thermisia gemmatalis*, *Tineola bisselliella* (webbing clothes moth), *Trichoplusia ni* (cabbage looper), *Tuts absoluta*, *yponomeuta* spp., *zeuzeracoffeae* (red branch borer) and *Zeuzera pyrina* (leopard moth).

Mallophaga (chewing lice): *Bovicola ovis* (sheep biting louse), *Menacanthus stramineus* (chicken body louse) and *Menopon gallinea* (common hen house).

Orthoptera (grasshopper, locust and cricket): *Anabrus simplex* (mormon cricket), *gryllotalpidae* (mole cricket), *Locusta migratoria, melanoplus* spp. (grasshopper), *Microcentrum retinerve* (angular winged katydid), *pterophylla* spp. (katydid), *Chistocerca gregaria, Scudderia furcata* (fork tailed bush katydid) and *Valanga nigricorni*.

Phthiraptera (sucking louse): *haematopinus* spp. (ox louse and pig louse), *Linognathus ovillus* (sheep louse), *Pediculus humanus capitis* (body louse), *Pediculus humanus humanus* (body louse) and *Pthirus pubis* (crab louse).

Siphonaptera (flea): *Ctenocephal ides canis* (dog flea), *Ctenocephalides felis* (cat flea) and *Pulex irritans* (human flea).

Thysanoptera (thrips): *Frankliniella fusca* (tobacco thrip), *Frankliniella occidentalis* (western flower thrips), *Frankliniella shultzei, Frankliniella williamsi* (corn thrip), *Iieliothrips haemorrhaidalis* (greenhouse thrip), *Riphiphorothrips cruentatus, scirtothrips* spp, *Scirtothrips cirri* (citrus thrip), *Scirtothrips dorsalis* (yellow tea thrips), *Taeniothrips rhopalantennalis* and *thrips* spp.

Thysanura (bristletail): *lepisma* spp. (silverfish) and *thermobia* spp. (special mess fish).

Acarina (mite and tick): *Acarapsis woodi* (tracheal mite of honeybee), *acarus* spp. (food mites), *Acarus siro* (grain mite), *Aceria mangiferae* (mango bud mite), *aculops* spp., *Aculops lycopersici* (tomato russet mite), *Aculops pelekasi, Aculus pelekassi, Aculus schlechtendali* (apple rust mite), *Amblyomma amcricanum* (lone star tick), *boophilus* spp. (tick), *Brevipalpus obovatus* (privet mite), *Brevipalpus phoenicis* (red and black flat mite), *demodex* spp. (mange mites), *dermacentor* spp. (hard tick), *Dermacentor variabilis* (American dog tick), *Dermatophagoides pteronyssinus* (house dust mite), *eotetranycus* spp., *Eotetranychus carpini* (yellow spider mite), *epitimerus* spp., *eriophyes* spp., *ixodes* (tick), *metatetranycus* spp., *Notoedres cati, oligonychus* spp., *Oligonychus coffee, Oligonychus ilicus* (southernred mite), *panonychus* spp., *Panonychus cirri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *rhizoglyphus* spp. (bulb mite), *Sarcoptes scabiei* (itch mite), *Tegolophus perseaflorae, tetranychus* spp., *Tetranychus urticae* (twospotted spider mite) and *Varroa destructor* (bee mite).

Nematoda (nematode): *aphelenchoides* spp. (bud and leaf & pine wood nematode), *belonolaimus* spp. (sting nematodes), *criconemella* spp. (ring nematodes), *Dirofilaria immitis* (dog heartworm), *ditylenchus* spp. (stem and corm nematode), *heterodera* spp. (cyst nematode), *Heterodera zeae* (corn cyst nematode), *hirschmanniella* spp. (root nematodes), *hoplolaimus* spp. (lance nematodes), *meloidogyne* spp. (knot nematode), *Meloidogyne incognita* (knot nematode), *Onchocerca volvulus* (hook-tail worm), praLylenchus spp. (lesion nematode), *radopholus* spp. (burrowing nematode) and *Rotylenchus reniformis* (kidney-shaped nematode).

Symphyla (comprehensive insects): *Scutigerella immaculata*.

Due to the positive characteristics, the above compounds can be advantageously used to protect important crops, livestock and breeding stock in agriculture and horticulture, and to avoid the damage of fungi, pests and mites to the environment that humans often go to.

To achieve an ideal effect, the use amount of the compound varies depending on various factors such as the used compound, the crop to be protected, the type of pest, the degree of infection, climatic conditions, the method of administration, and the adopted dosage form.

The dose of 10 grams to 5 kilograms of compound per hectare can provide adequate control.

The present invention also comprises a fungicidal, insecticidal and acaricidal composition using the compound shown by the general formula I as an active ingredient. The weight percentage of the fungicidal, insecticidal and acaricidal composition in the active ingredient is 0.5-99%. The fungicidal, insecticidal and acaricidal composition also comprises acceptable carriers in agriculture, forestry and sanitation.

The composition of the present invention can be applied in the form of formulations. The compound shown by the general formula I is dissolved or dispersed in the carrier as the active ingredient or prepared into the formulation for easier dispersion when used as a fungicide and an insecticide. For example, the chemical formulations can be prepared into wettable powder, an oil dispersion, an aqueous suspension, an aqueous emulsion, a water aqua or missible oil.

In these compositions, one liquid or solid carrier is at least added, and appropriate surfactants may be added when required.

The technical solution of the present invention also comprises a method for controlling fungi, pests and mites: applying the fungicidal, insecticidal and acaricidal composition of the present invention to a fungi or a growth medium of the fungi. The more appropriate effective dose which is often selected is 10 to 1000 grams per hectare, and preferably, the effective dose is 20 to 500 grams per hectare.

For some applications, for example in agriculture, the addition of one or more other fungicides, insecticides, acaricides, herbicides, plant growth regulators or fertilizers to the fungicidal, insecticidal and acaricidal composition of the present invention can produce additional advantages and effects.

It should be clear that various changes and modifications can be made within the scope defined by the claims of the present invention.

The Present Invention has the Following Advantages:

The substituted pyrimidine compound shown by the general formula I of the present invention has obvious structural features, so that the compound has novel structure. Moreover, the compound of the present invention has obvious fungicidal, insecticidal and acaricidal activity, and has outstanding effect on different target crops. Meanwhile, under some different low dosages (e.g., 25 ppm, 10 ppm, 8.3 ppm, 6.25 ppm, 2.8 ppm and 2.5 ppm) part of the compounds of the present invention have outstanding effects, thereby reducing the utilization cost. Further, it can be seen that the compound shown by the general formula I in the present invention shows excellent activity against various fungi in agriculture or other fields, also shows good activity against pests and mites, and can be further developed into a new fungicide, insecticide and acaricide.

DETAILED DESCRIPTION

The following specific embodiments are used to further illustrate the present invention, but the present invention is not limited to these examples (unless otherwise specified, the raw materials used are commercially available).

SYNTHESIS EMBODIMENTS

Embodiment 1: Preparation of Intermediate 4,5-dichloro-6-methylpyrimidine

1) Preparation of 4-hydroxy-5-chloro-6-methylpyrimidine

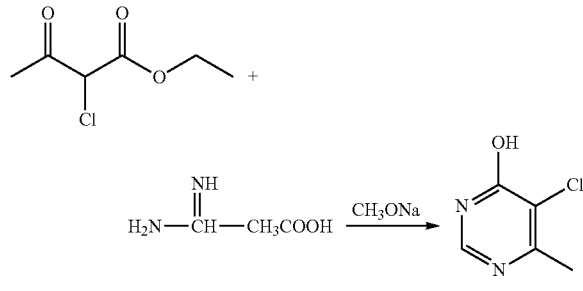

The methanol solution of 8.80 g (0.16 mol) of sodium methoxide is slowly added to 50 ml of methanol solution of 11.30 g (0.11 mol) formamidine acetate under stirring at room temperature, and the mixture is continuously stirred at room temperature for 2 h after adding. Then, 11.17 g (0.068 mol) of intermediate ethyl 2-chloro-3-oxobutanoate is added dropwise to the above solution, and the mixture is continuously stirred at room temperature for 5-7 h. After the reaction was complete monitored by TLC, the solvent is evaporated under reduced pressure; the pH is adjusted with hydrochloric acid to 5-6; suction filtration is conducted to obtain orange yellow solid; the aqueous phase is extracted with (3×50 ml) ethyl acetate, dried with anhydrous magnesium sulfate, filtered, and desolventized. The residue is dissolved in 50 ml of ethyl acetate, placed overnight, and filtered to obtain 6.48 g of orange yellow solid. The yield is 66%, and the melting point is 181-184° C.

2) Preparation of 4,5-dichloro-6-methylpyrimidine

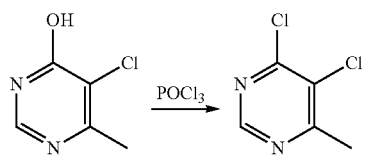

14.5 g (0.1 mol) of 4-hydroxy-5-chloro-6-methylpyrimidine is dissolved in 50 ml of toluene solution, and 50 ml of phosphorus oxychloride is dropped into the reaction flask under stirring. After dropping, the mixture is heated to reflux for 5-7 h. After the reaction was complete monitored by TLC, the toluene and excessive phosphorous oxychloride are evaporated under reduced pressure; the reactants are poured into ice water under stirring; the aqueous phase is extracted with (3×50 ml) ethyl acetate, the organic phase was merged, dried with anhydrous magnesium sulfate, filtered, and desolventized. The residue is separated by column chromatography (the eluent includes ethyl acetate and petroleum ether with a volume ratio of 1:5) to obtain 14.43 g of yellow liquid with a yield of 88.5%.

Embodiment 2: Preparation of 4,5-Dichlorothieno [2,3-d] Pyrimidine

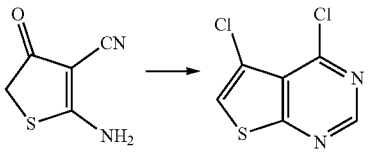 [SMILES: N#CC1=C(N)SCC1=O ; Clc1csc2ncnc(Cl)c12]

2-amino-3-cyano-4-oxo-5,5-dihydrothiophene and 250 ml of phosphorus oxychloride (POCl3) are taken in the reaction flask, and 38 ml of N, N-dimethyl formamide is slowly added dropwise at room temperature for about 30 h. The mixture is reacted at room temperature for 1 h, and then heated to 75° C. to react for another 3 h. After cooled to the room temperature, the reaction solution is poured into the crushed ice, and filtered to obtain 89.1 g of dark grey solid, with a yield of 86.9% and a melting point of 160-161° C.

Embodiment 3: Preparation of Intermediate 4-chloroquinazoline

1) Preparation of Quinazolin-4 (3H)-One

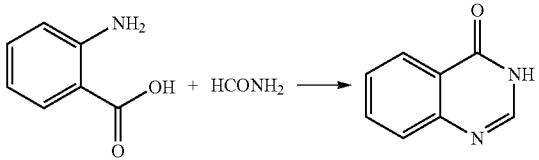

13.7 g (0.1 mol) of anthranilic acid and 20 ml of formylamine are taken into a 250 ml flask with three necks, and heated to 140° C. to react for 5-8 h. After the reaction was complete monitored by TLC, the reaction solution is cooled to 100° C. 80 ml of water is added dropwise under stirring. Then, the mixture is cooled to room temperature and filtered. The filter cake is washed with absolute ether to obtain 10.96 g of reddish brown substance, with a yield of 75.1%.

2) Preparation of 4-chloroquinazoline

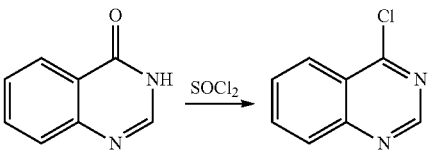

14.6 g (0.1 mol) of quinazolin-4 (3H)-one is taken into a 250 ml flask with one neck, 50 ml of thionyl chloride is used as the solvent. The mixture is heated for reflux reaction for 4-6 h. After the reaction was complete monitored by TLC, the reaction solution is cooled, then poured into water for stirring for 30 min, and filtered. The filter cake is washed with absolute ether to obtain 10.96 g of reddish brown solid, with a yield of 92.7%.

Embodiment 4: Synthesis of Intermediate 3-(5-phenyl-1,4-dimethyl-pyrazole-3-oxy) propylamine hydrochloride 1) Preparation of N-Boc-2-bromopropylamine

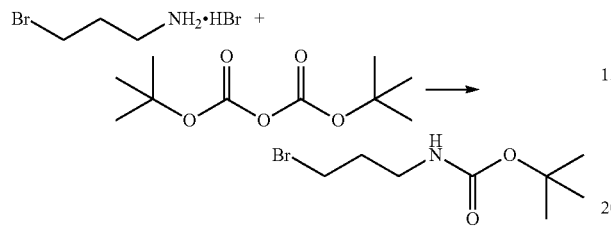

21.6 g (0.1 mol) of bromoethylamine bromate is placed in 80 ml of tetrahydrofuran, an 10.08 g (0.12 mol) of sodium bicarbonate and 50 ml of water are successively added; 21.80 g (0.1 mol) of di-tert-butyl dicarbonate is dropwise added under stirring at room temperature. After adding, the reaction is continued for 4-10 h. After the reaction is complete, the solvent is evaporated under reduced pressure, and (3×50 ml) ethyl acetate is added for extraction. The organic phase is washed with 50 ml of saturated salt solution, and evaporated under reduced pressure to obtain 22.7 g of colorless oily liquid, with a yield of 95.7%.

2) Preparation of N-Boc-3-(5-phenyl-1,4-dimethyl-pyrazol-3-oxy) propylamine

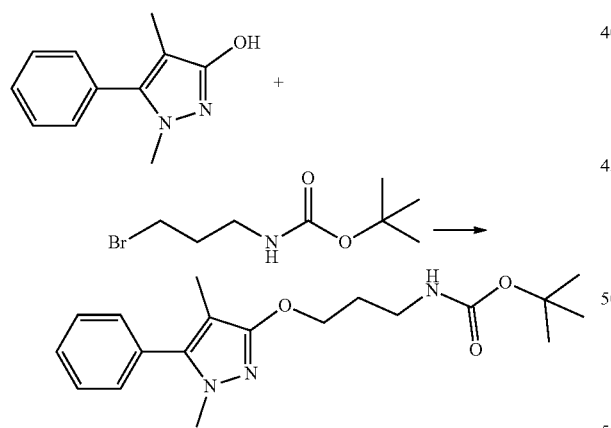

2.38 g (0.01 mol) of N-Boc-3-bromopropylamine and 1.88 g (0.01 mol) of 5-phenyl-1,4-dimethyl-3-hydroxypyrazole (refer to CN102584705 for the preparation method) are added to 50 ml of butanone; 2.76 g (0.02 mol) of potassium carbonate is added and heated for reflux reaction for 4-10 h under stirring; after the reaction was complete monitored by TLC, the solvent is evaporated under reduced pressure; and (3×50 ml) ethyl acetate is added for extraction. The organic phase is washed with 50 ml of saturated salt solution, and evaporated under reduced pressure, the residue was purified by column chromatography (the eluent includes ethyl acetate and petroleum ether with a volume ratio of 1:6) to obtain 2.94 g of yellow solid, with a yield of 85.2%.

3) Preparation of 3-(5-phenyl-1,4-dimethyl-pyrazole-3-oxy) propylamine hydrochloride

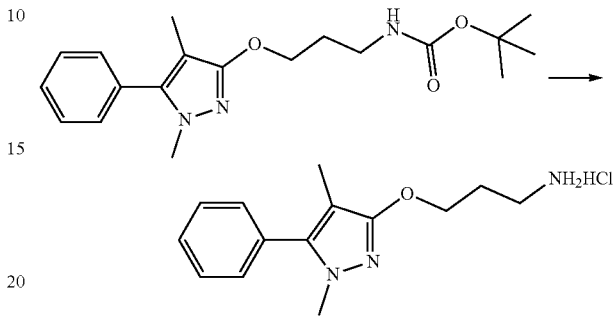

3.45 g (0.01 mol) of N-Boc-3-(5-phenyl-1,4-dimethyl-pyrazol-3-oxy) propylamine is added to 50 ml of ethyl acetate; 6 ml of concentrated hydrochloric acid is added dropwise under stirring at room temperature; the solid is dissolved; the stirring is continued for 4-5 h; after the reaction was complete monitored by TLC, the solvent is evaporated under reduced pressure; 10 ml of dichloromethane is added and stirred for half an hour; and the solvent is evaporated under reduced pressure to obtain 2.68 g of yellow oil.

Embodiment 5: Synthesis of Intermediate 3-(5-(2,4-dichlorophenyl)-1-methyl-pyrazole-3-oxy) ethylamine hydrochloride 1) Preparation of N-Boc-2-(5-(2,4-dichlorophenyl)-1-methyl-pyrazole-3-oxy) ethylamine hydrochloride

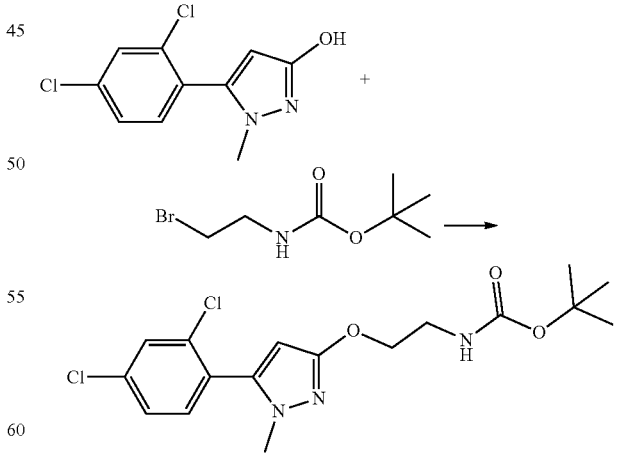

2.24 g (0.01 mol) of N-Boc-2-bromoethylamine (refer to step 1 in embodiment 4 for the preparation method) and 2.43 g (0.01 mol) of 5-(2,4-dichlorophenyl)-1-methyl-3-hydroxypyrazole (refer to CN102584705 for the preparation method) are added to 50 ml of butanone; 2.76 g (0.02 mol)

of potassium carbonate is added and heated for reflex reaction for 4-10 h under stirring; after the reaction was complete monitored by TLC, the solvent is evaporated under reduced pressure; and (3×50 ml) ethyl acetate is added for extraction. The organic phase is washed with 50 ml of saturated salt solution, and evaporated under reduced pressure, the residue was purified by column chromatography (the eluent includes ethyl acetate and petroleum ether with a volume ratio of 1:6) to obtain 3.12 g of yellow solid, with a yield of 80.8%.

2) Preparation of intermediate 3-(5-(2,4-dichlorophenyl)-1-methyl-pyrazole-3-oxy) ethylamine hydrochloride

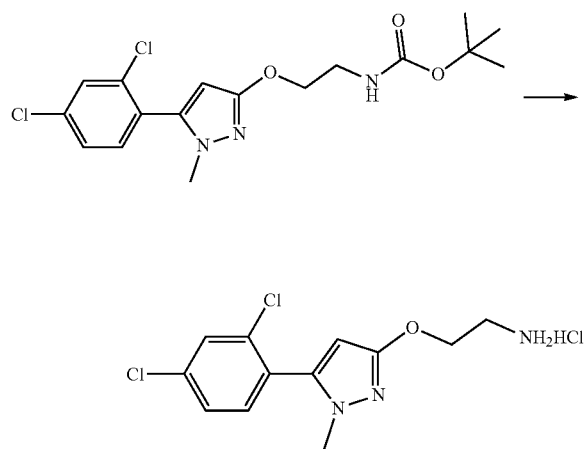

3.86 g (0.01 mol) of N-Boc-2-(5-(2,4-dichlorophenyl)-1-methyl-pyrazole-3-oxy) ethylamine is added to 50 ml of ethyl acetate; 6 ml of concentrated hydrochloric acid is added dropwise under stirring at room temperature; the solid is dissolved; the stirring is continued for 4-5 h; after the reaction was complete monitored by TLC, the solvent is evaporated under reduced pressure; 10 ml of dichloromethane is added, stirred for half an hour and filtered; and the filter cake is washed with dichloromethane to obtain 3.05 g of pale yellow solid.

Embodiment 6: Synthesis of Intermediate 3-(5-(2,4-Dichlorophenyl)-1-Methyl-Pyrazole-3-Oxy) Ethylamine Hydrochloride 1) Preparation of N-Boc-2-(5-(4-methoxyphenyl)-1, 4-dimethyl-pyrazole-3-oxy) ethylamine

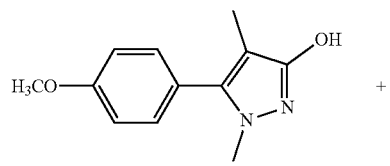

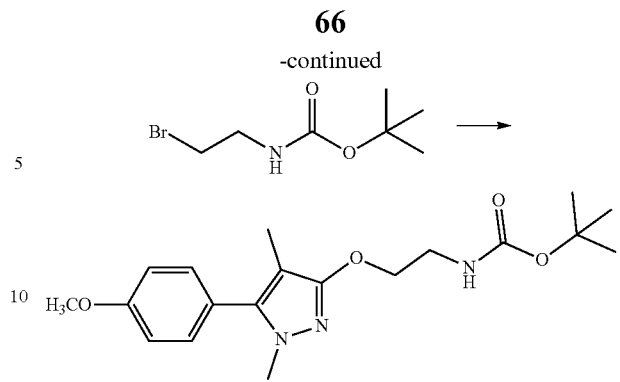

2.24 g (0.01 mol) of N-Boc-2-bromoethylamine and 2.18 g (0.01 mol) of 5-(4-methoxyphenyl-1,4-dimethyl-3-hydroxypyrazole (refer to CN102584705 for the preparation method) are added to 50 ml of butanone; 2.76 g (0.02 mol) of potassium carbonate is added and heated for reflex reaction for 4-10 h under stirring; after the reaction was complete monitored by TLC, the solvent is evaporated under reduced pressure; and (3×50 ml) ethyl acetate is added for extraction. The organic phase is washed with 50 ml of saturated salt solution, and evaporated under reduced pressure, the residue was purified by column chromatography (the eluent includes ethyl acetate and petroleum ether with a volume ratio of 1:6) to obtain 2.96 g of yellow solid, with a yield of 82.0%.

2) Preparation of intermediate 3-(5-(2,4-dichlorophenyl)-1-methyl-pyrazole-3-oxy) ethylamine hydrochloride

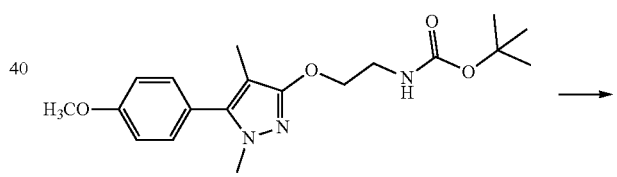

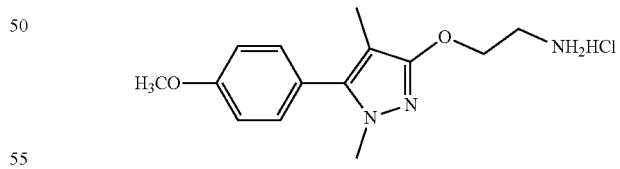

3.61 g (0.01 mol) of N-Boc-2-(5-(4-methoxyphenyl)-1,4-dimethyl-pyrazole-3-oxy) ethylamine is added to 50 ml of ethyl acetate; 6 ml of concentrated hydrochloric acid is added dropwise under stirring at room temperature; the solid is dissolved; the stirring is continued for 4-5 h; after the reaction was complete monitored by TLC, the solvent is evaporated under reduced pressure; 10 ml of dichloromethane is added and stirred for half an hour; and the solvent is evaporated under reduced pressure to obtain 2.33 g of yellow oil.

Embodiment 7: Synthesis of Intermediate 3-(5-(4-bromophenyl)-1-methyl-pyrazole-3-oxy) ethylamine hydrochloride 1) Preparation of N-Boc-2-(5-(4-bromophenyl)-1-methyl-pyrazole-3-oxy) ethylamine

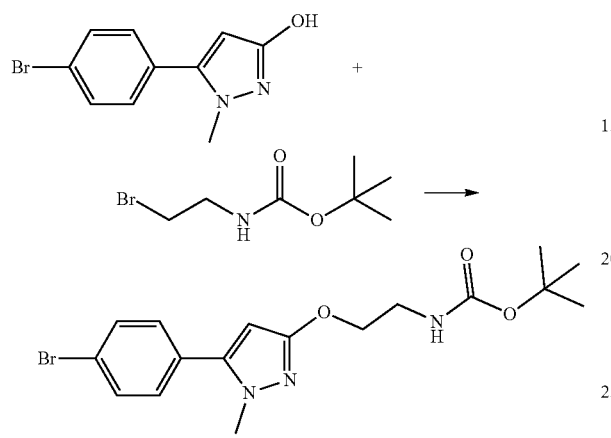

2.24 g (0.01 mol) of N-Boc-2-bromoethylamine and 2.53 g (0.01 mol) of 5-(4-bromophenyl)-1-methyl-3-hydroxypyrazole (refer to CN102584705 for the preparation method) are added to 50 ml of butanone; 2.76 g (0.02 mol) of potassium carbonate is added and heated for reflux reaction for 4-10 h under stirring; after the reaction was complete monitored by TLC, the solvent is evaporated under reduced pressure; and (3×50 ml) ethyl acetate is added for extraction. The organic phase is washed with 50 ml of saturated salt solution, and evaporated under reduced pressure, the residue was purified by column chromatography on the residues (the eluent includes ethyl acetate and petroleum ether with a volume ratio of 1:6) to obtain 3.15 g of reddish brown solid, with a yield of 79.5%.

2) Preparation of 3-(5-(4-bromophenyl)-1-methyl-pyrazole-3-oxy) ethylamine hydrochloride

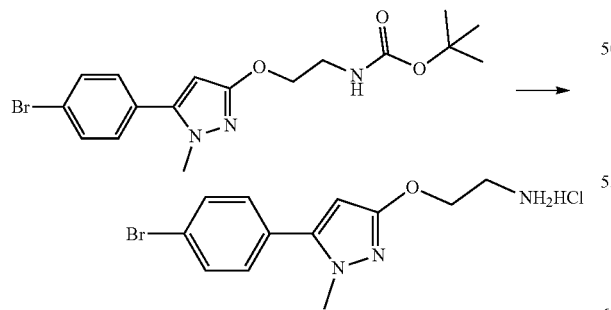

3.96 g (0.01 mol) of N-Boc-2-(5-(4-bromophenyl)-1-methyl-pyrazole-3-oxy) ethylamine is added to 50 ml of ethyl acetate; 6 ml of concentrated hydrochloric acid is added dropwise under stirring at room temperature; the solid is dissolved; the stirring is continued for 4-5 h; after the reaction was complete monitored by TLC, the solvent is evaporated under reduced pressure; 10 ml of dichloromethane is added, stirred for half an hour and filtered; and the filter cake is washed with dichloromethane to obtain 3.05 g of pink solid.

Embodiment 8: Synthesis of Intermediate 1-methyl-2-(5-phenyl-1,4-dimethyl-3-oxy) ethylamine 1) Preparation of 1-(5-phenyl-1,4-dimethyl-pyrazole-3-oxy) acetone

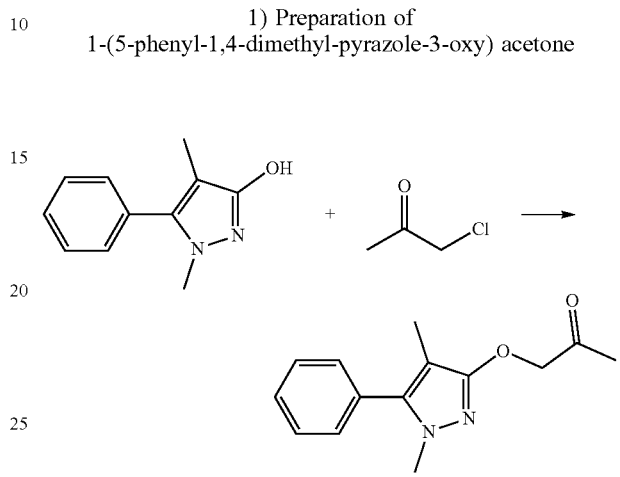

0.93 g (0.01 mol) of chloroacetone and 1.88 g (0.01 mol) of 5-phenyl-1,4-dimethyl-3-hydroxypyrazole (refer to CN102584705 for the preparation method) are added to 50 ml of 50 ml DMF; 2.76 g (0.02 mol) of potassium carbonate is added and heated for reflux reaction for 4-10 h under stirring; after the reaction was complete monitored by TLC, the solvent is evaporated under reduced pressure; and (3×50 ml) ethyl acetate is added for extraction. The organic phase is washed with 50 ml of saturated salt solution, and evaporated under reduced pressure, the residue was purified by column chromatography on the residues (the eluent includes ethyl acetate and petroleum ether with a volume ratio of 1:5) to obtain 3.15 g of reddish brown solid, with a yield of 79.5%.

2) Preparation of 1-methyl-2-(5-phenyl-1,4-dimethyl-3-oxy) ethylamine

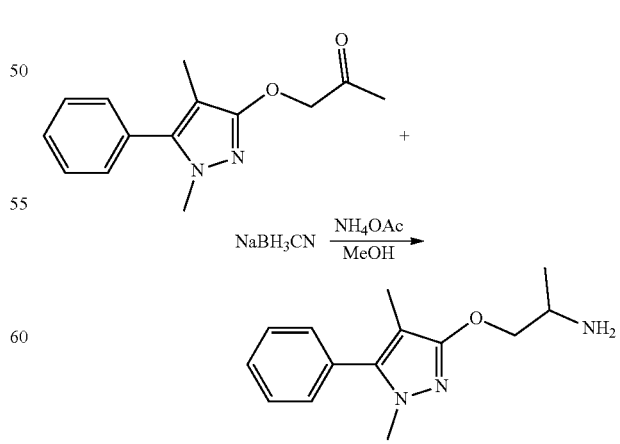

2.44 g (0.01 mol) of 1-(5-phenyl-1,4-dimethyl-pyrazole-3-oxy) acetone and 11.5 g (0.15 mol) of ammonium acetate are added to 50 ml of methanol; 1.26 g (0.02 mol) of sodium cyanoborohydride is added in portions; after that, 1 ml of glacial acetic acid is added dropwise, and stirred under ice bath to react for 4-10 h; after the reaction was complete monitored by TLC, aqueous sodium hydroxide is added dropwise to the reaction solution until pH is 8-9; and (3×50 ml) ethyl acetate is added for extraction. The organic phase is washed with 50 ml of saturated salt solution, and evaporated under reduced pressure to obtain 1.96 g of yellow oil.

Embodiment 9: Preparation of Compound 12-3-1

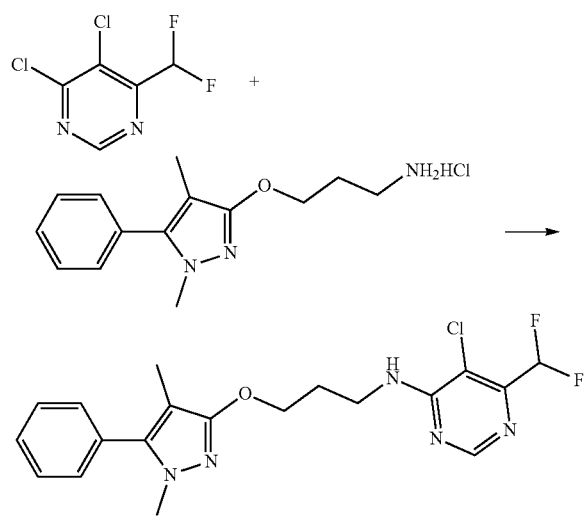

1.99 g (0.01 mol) of 4,5-dichloro-6-difluoromethylpyrimidine and 2.82 g (0.01 mol) of 3-(5-phenyl-1,4-dimethyl-pyrazole-3-oxy) propylamine hydrochloride are added to 50 ml of toluene. 4.45 g (0.022 mol) of triethylamine is added, and heated for reflex reaction for 4-10 h; after the reaction was complete monitored by TLC, the solvent is evaporated under reduced pressure; and (3×50 ml) ethyl acetate is added for extraction. The organic phase is washed with 50 ml of saturated salt solution, and evaporated under reduced pressure, the residue was purified by column chromatography on the residues (the eluent includes ethyl acetate and petroleum ether (boiling range is 60-90° C.) with a volume ratio of 1:2) to obtain 1.95 g of yellow oil, with a yield of 47.9%.

$^1$H-NMR (600 MHz, internal standard TMS, solvent CDCl$_3$) δ(ppm): 8.54 (s, 1H, Pyrimidine-H), 7.48 (t, J=6 Hz, 2H, Ph-3,5-2H), 7.42 (t, J=6 Hz, 1H, Ph-4-H), 7.32 (d, J=6 Hz, 2H, Ph-2,6-2H), 6.75 (s, 1H, NH), 6.73 (t, J$_{HF}$=54 Hz, 1H, CHF$_2$), 4.41 (t, J=6 Hz, 2H, O—CH$_2$), 3.77-3.80 (q, J=6 Hz, 2H, N—CH$_2$), 3.63 (s, 3H, N—CH$_3$), 2.10-2.14 (m, 2H, CH$_2$), 1.89 (s, 3H, Pyrazole-4-CH$_3$).

Embodiment 10: Preparation of Compound 19-21

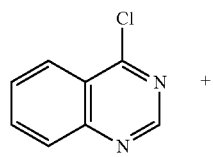

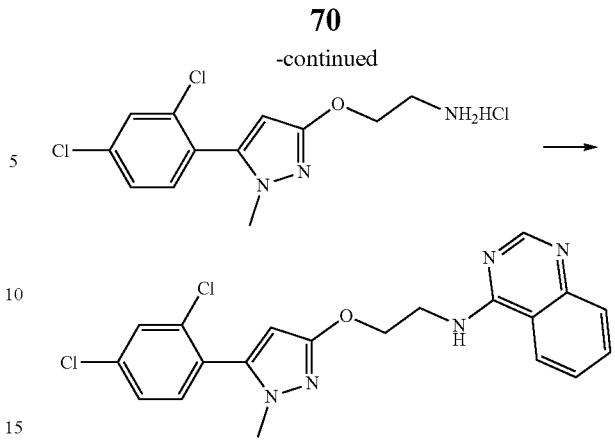

1.65 g (0.01 mol) of 4-chloroquinazoline and 3.22 g (0.01 mol) of 3-(5-(2,4-dichlorophenyl)-1-methyl-pyrazole-3-oxy) ethylamine hydrochloride are added to 50 ml of toluene. 4.45 g (0.022 mol) of triethylamine is added, and heated for reflex reaction for 4-10 h; after the reaction was complete monitored by TLC, the solvent is evaporated under reduced pressure; and (3×50 ml) ethyl acetate is added for extraction. The organic phase is washed with 50 ml of saturated salt solution, and evaporated under reduced pressure, the residue was purified by column chromatography on the residues (the eluent includes ethyl acetate and petroleum ether (boiling range is 60-90° C.) with a volume ratio of 1:2) to obtain 2.85 g of brown oil, with a yield of 68.8%.

$^1$H-NMR (600 MHz, internal standard TMS, solvent CDCl$_3$) δ(ppm): 8.70 (s, 1H, Quinazoline-3-H), 7.88 (d, J=6 Hz, 1H, Quinazoline-5-H), 7.77 (t, J=6 Hz, 1H, Quinazoline-6-H), 7.74 (d, J=6 Hz, 1H, Quinazoline-8-H), 7.70 (d, J=12 Hz, 1H, Ph-6-H), 7.49 (t, J=6 Hz, 1H, Quinazoline-7-H), 7.41 (s, 1H, Ph-3-H), 7.25 (d, J=12 Hz, 1H, Ph-5-H), 6.19 (s, 1H, NH), 6.10 (s, H, Pyrazole-4-H), 4.42 (t, J=6 Hz, 2H, O—CH$_2$), 4.13-4.16 (q, J=6 Hz, 2H, N—CH$_2$), 3.72 (s, 3H, N—CH$_3$).

Embodiment 11: Preparation of Compound 21-1-72

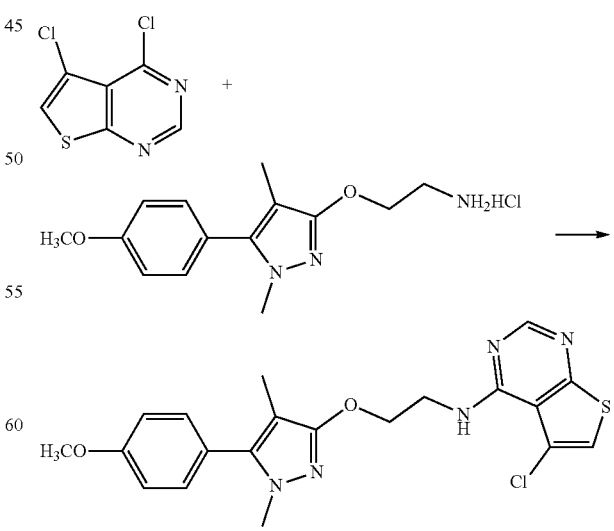

2.05 g (0.01 mol) of 4,5-dichlorothieno [2,3-d] pyrimidine and 2.98 g (0.01 mol) of 3-(5-(2,4-dichlorophenyl)-1- methyl-pyrazole-3-oxy) ethylamine hydrochloride are added to 50 ml of toluene. 4.45 g (0.022 mol) of triethylamine is added, and heated for reflex reaction for 4-10 h; after the reaction was complete monitored by TLC, the solvent is evaporated under reduced pressure; and (3×50 ml) ethyl acetate is added for extraction. The organic phase is washed with 50 ml of saturated salt solution, and evaporated under reduced pressure, the residue was purified by column chromatography on the residues (the eluent includes ethyl acetate and petroleum ether (boiling range is 60-90° C.) with a volume ratio of 1:2) to obtain 2.24 g of yellow solid with a melting point of 121.7° C., with a yield of 52.2%.

$^1$H-NMR (600 MHz, internal standard TMS, solvent CDCl3) δ(ppm): 8.47 (s, 1H, Pyrimidine-H), 7.22 (d, J=6 Hz, 2H, Ph-2,6-2H), 7.07 (s, 1H, NH), 7.06 (s, 1H, Thiophene-H), 6.99 (d, J=6 Hz, 2H, Ph-3,5-2H), 4.50 (t, J=6 Hz, 2H, O—CH$_2$), 4.05-4.07 (q, J=6 Hz, 2H, N—CH$_2$), 3.86 (s, 3H, N—CH$_3$), 3.58 (s, 3H, OCH$_3$), 1.86 (s, 3H, Pyrazole-4-CH$_3$).

Embodiment 12: Preparation of Compound 19-34

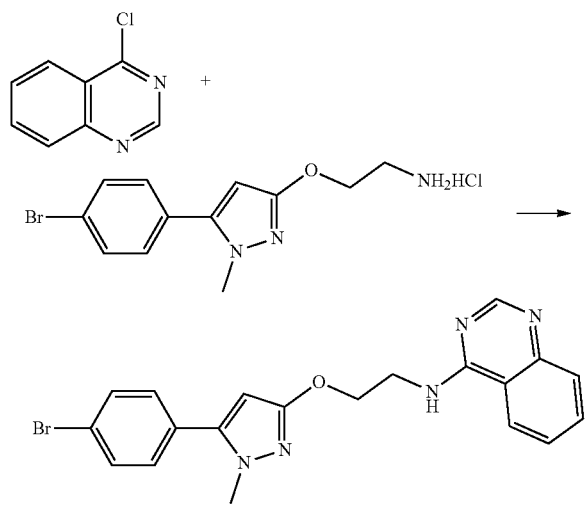

1.65 g (0.01 mol) of 4-chloroquinazoline and 3.33 g (0.01 mol) of 3-(5-(4-bromophenyl)-1-methyl-pyrazole-3-oxy) ethylamine hydrochloride are added to 50 ml of toluene. 4.45 g (0.022 mol) of triethylamine is added, and heated for reflex reaction for 4-10 h; after the reaction was complete monitored by TLC, the solvent is evaporated under reduced pressure; and (3×50 ml) ethyl acetate is added for extraction. The organic phase is washed with 50 ml of saturated salt solution, and evaporated under reduced pressure, the residue was purified by column chromatography on the residues (the eluent includes ethyl acetate and petroleum ether (boiling range is 60-90° C.) with a volume ratio of 1:2) to obtain 2.09 g of white solid, with a yield of 49.4%.

$^1$H-NMR (600 MHz, internal standard TMS, solvent CDCl3) δ(ppm): 8.66 (s, 1H, Quinazoline-3-H), 7.84 (d, J=6 Hz, 2H, Quinazoline-5,8-2H), 7.73 (t, J=6 Hz, 2H, Quinazoline-6,7-2H), 7.45 (d, J=6 Hz, 2H, Ph-2,6-2H), 7.39 (d, J=6 Hz, 2H, Ph-3,5-2H), 7.05 (s, 1H, NH), 5.87 (s, 1H, Pyrazole-4-H), 4.51 (t, J=6 Hz, 2H, O—CH$_2$), 4.04-4.09 (q, 2H, N—CH$_2$), 3.77 (s, 3H, N—CH$_3$).

Embodiment 13: Preparation of Compound 11-4-1

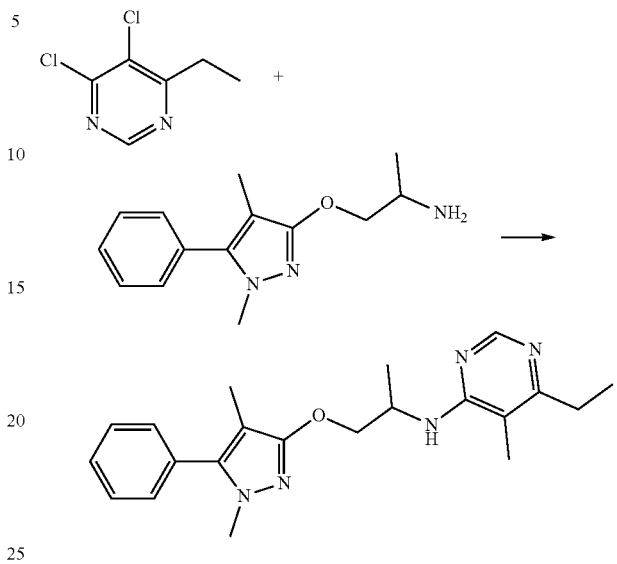

1.77 g (0.01 mol) of 4,5-dichloro-6-ethylpyrimidine and 2.45 g (0.01 mol) of 1-methyl-2-(5-phenyl-1,4-dimethyl-3-oxy) ethylamine are added to 50 ml of toluene. 4.45 g (0.022 mol) of triethylamine is added, and heated for reflex reaction for 4-10 h; after the reaction was complete monitored by TLC, the solvent is evaporated under reduced pressure; and (3×50 ml) ethyl acetate is added for extraction. The organic phase is washed with 50 ml of saturated salt solution, and evaporated under reduced pressure, the residue was purified by column chromatography on the residues (the eluent includes ethyl acetate and petroleum ether (boiling range is 60-90° C.) with a volume ratio of 1:2) to obtain 1.05 g of yellow oil, with a yield of 28.8%.

$^1$H-NMR (600 MHz, internal standard TMS, solvent CDCl3) δ(ppm): 8.42 (s, 1H, Pyrimidine-H), 7.47 (t, J=6 Hz, 2H, Ph-3,5-2H), 7.41 (t, J=61-z, 1H, Ph-4-H), 7.30 (d, J=6 Hz, 2H, Ph-2,6-2H), 6.22 (s, 1H, NH), 4.59-4.62 (m, 1H, N—CH), 4.35 (d, J=6 Hz, 2H, O—CH$_2$), 3.61 (s, 3H, N—CH$_3$), 2.76-2.80 (q, J=6 Hz, 2H, CH$_2$CH$_3$), 1.86 (s, 3H, Pyrazole-4-CH$_3$), 1.41 (s, 3H, CHCH$_3$), 1.26 (t, J=6 Hz, 3H, CH$_2$CH$_3$).

Other compounds of the present invention can be prepared by referring to the above embodiments.

The physical property data and nuclear magnetic data of part of compounds ($^1$H NMR, 600 MHz, internal standard TMS, ppm) are as follows:

Compound 10-1: melting point of 118.2° C. δ(CDCl3): 8.41 (s, 1H, Pyrimidine-H), 7.72 (m, 2H, Ph-2,6-2H), 7.37 (m, 2H, Ph-3,5-2H), 7.29 (m, 1H, Ph-4-H), 5.85 (s, 1H, Pyrazole-H), 5.75 (s, 1H, NH), 4.30 (t, J=6 Hz, 2H, O—CH$_2$), 3.98 (m, 2H, NH—CH$_2$), 3.71 (s, 3H, N—CH$_3$).

Compound 10-21: melting point of 110.8° C. δ(CDCl3): 8.40 (s, 1H, Pyrimidine-H), 7.72 (d, J=6 Hz, 1H, Ph-6-H), 7.43 (s, 1H, Ph-3-H), 7.25 (dd, J=6 Hz, 1H, Ph-5-H), 6.09 (s, Pyrazole-4-H), 5.72 (s, 1H, NH), 4.30 (t, J=6 Hz, 2H, O—CH$_2$), 3.96-3.99 (q, J=6 Hz, 2H, N—CH$_3$), 3.72 (s, 3H, N—CH$_3$), 2.48 (s, 3H, CH$_3$).

Compound 10-34: melting point of 112.9° C. δ(CDCl3): 8.41 (s, 1H, Pyrimidine-H), 7.59 (d, J=6 Hz, 2H, Ph-2,6-2H), 7.49 (d, J=6 Hz, 2H, Ph-3,5-2H), 5.82 (s, 1H, Pyrazole- H), 5.71 (s, 1H, NH), 4.29 (t, J=6 Hz, 2H, O—CH$_2$), 3.98 (m, 2H), 3.70 (s, 3H, NH—CH$_2$), 2.48 (s, 3H, Pyrimidine-CH$_3$).

Compound 10-69: melting point of 145.3° C. δ(CDCl3): 8.41 (s, 1H, Pyrimidine-H), 7.82 (d, J=6 Hz, 2H, Ph-2,6-2H), 7.62 (d, J=6 Hz, 2H, Ph-3,5-2H), 5.89 (s, 1H, Pyrazole-4-H), 5.72 (s, 1H, NH), 4.31 (t, J=6 Hz, 2H, O—CH$_2$), 3.97-4.00 (q, J=6 Hz, 2H, N—CH$_2$), 3.72 (s, 3H, N—CH$_3$), 2.48 (s, 3H, Pyrimidine-CH$_3$).

Compound 10-1-4: oil. δ(CDCl3): 8.38 (s, 1H, Pyrimidine-H), 7.28 (d, J=6 Hz, 21H, Ph-2,6-2H), 7.17 (d, J=6 Hz, 2H, Ph-3,5-2H), 6.43 (s, 1H, NH), 4.47 (t, J=6 Hz, 2H, O—CH$_2$), 3.91 (in, 2H, NH—CH$_2$), 3.60 (s, 3H, N—CH$_3$), 2.45 (s, 3H, Pyrimidine-CH$_3$), 1.86 (s, 3H, Pyrazole-4-CH$_3$).

Compound 10-1-19: melting point of 109.4° C. δ(CDCl3): 8.38 (s, 1H, Pyrimidine-H), 7.45 (d, J=6 Hz, 2H, Ph-2,6-2H), 7.25 (d, J=6 Hz, 2H, Ph-3,5-2H), 6.42 (s, 1H, NH), 4.47 (t, J=6 Hz, 2H, O—CH$_2$), 3.91 (m, 2H, NH—CH$_2$), 3.61 (s, 3H, N—CH$_3$), 2.46 (s, 3H, Pyrimidine-CH$_3$), 1.86 (s, 3H, Pyrazole-4-CH$_3$).

Compound 10-1-57: melting point of 154.6° C. δ(CDCl3): 8.38 (s, 1H, Pyrimidine-H), 7.28 (d, J=6 Hz, 2H, Ph-2,6-2H), 7.19 (d, J=6 Hz, 2H, Ph-3,5-2H), 6.48 (s, 1H, NH), 4.47 (t, J=6 Hz, 2H, O—CH$_2$), 3.91 (m, 2H, NH—CH$_2$), 3.61 (s, 3H, N—CH$_3$), 2.46 (s, 3H, Pyrimidine-CH$_3$), 2.42 (s, 3H, Ph-4-CH$_3$), 2.42 (s, 3H, Pyrazole-CH$_3$).

Compound 10-1-66: oil. δ(CDCl3): 8.38 (s, 1H, Pyrimidine-H), 7.29 (d, 2H, Ph-2,6-2H), 7.22 (d, 2H, Ph-3,5-2H), 6.45 (s, 1H, NH), 4.47 (t, 2H, O—CH$_2$), 3.91 (m, 2H, N—CH$_2$), 3.62 (s, 3H, N—CH$_3$), 2.72 (m, 2H, CH$_2$), 2.45 (s, 3H, CH$_3$), 1.87 (s, 3H, Pyrazole-4-CH$_3$), 1.29 (t, 3H, CH$_3$).

Compound 10-1-69: melting point of 281.6° C. δ(CDCl3): 8.38 (s, 1H, Pyrimidine-H), 7.74 (d, 2H, Ph-2,6-2H), 7.44 (d, 2H, Ph-3,5-2H), 6.35 (s, 1H, NH), 4.47 (t, 2H, O—CH$_2$), 3.92 (m, 2H, N—CH$_2$), 3.62 (s, 3H, N—CH$_3$), 2.45 (s, 3H, CH$_3$), 1.88 (s, 3H, Pyrazole-4-CH$_3$).

Compound 10-1-72: melting point of 110.6° C. δ(CDCl3): 8.37 (s, 1H, Pyrimidine-H), 7.23 (d, J=6 Hz, 2H, Ph-2,6-2H), 6.99 (d, J=6 Hz, 2H, Ph-3,5-2H), 6.47 (s, 1H, NH), 4.47 (t, J=6 Hz, 2H, O—CH$_2$), 3.89-3.92 (q, J=6 Hz, 2H, N—CH$_2$), 3.86 (s, 3H, N—CH$_3$), 3.60 (s, 3H, OCH$_3$), 2.46 (s, 3H, Pyrimidine-CH$_3$), 1.86 (s, 3H, Pyrazole-4-CH$_3$).

Compound 10-1-288: oil. δ(CDCl$_3$): 8.38 (s, 1H, Pyrimidine-H), 7.47 (d, J=6 Hz, 2H, Ph-2,6-2H), 7.24 (d, J=6 Hz, 2H, Ph-3,5-2H), 6.45 (s, 1H, NH), 4.47 (t, J=6 Hz, 2H, O—CH$_2$), 3.91 (m, 2H, NH—CH$_2$), 3.63 (s, 3H, N—CH$_3$), 2.45 (s, 3H, Pyrimidine-CH$_3$), 1.88 (s, 3H, Pyrazole-4-CH$_3$), 1.37 (s, 9H, C$_4$Hg).

Compound 10-3-1: oil. δ(CDCl3): 8.37 (s, 1H, Pyrimidine-H), 7.47 (t, J=6 Hz, 2H, Ph-3,5-2H), 7.41 (t, J=6 Hz, 1H, Ph-4-H), 7.32 (d, 1=6 Hz, 2H, Ph-2,6-2H), 6.23 (s, 1H, NH), 4.39 (t, J=6 Hz, 2H, O—CH$_2$), 3.71-3.74 (q, J=6 Hz, 2H, N—CH$_2$), 3.63 (s, 3H, N—CH$_3$), 2.45 (s, 3H, CH$_3$), 2.10-2.14 (m, 2H, CH$_2$), 1.89 (s, 3H, Pyrazole-4-CH$_3$).

Compound 10-4-1: oil. δ(CDCl3): 8.37 (s, 1H, Pyrimidine-H), 7.47 (t, J=6 Hz, 2H, Ph-3,5-2H), 7.41 (t, J=6 Hz, 1H, Ph-4-H), 7.30 (d, J=6 Hz, 2H, Ph-2,6-2H), 6.22 (s, 1H, NH), 4.58-4.63 (m, 1H, N—CH), 4.35 (d, J=6 Hz, 2H, O—CH$_2$), 3.61 (s, 3H, N—CH$_3$), 2.45 (s, 3H, CH$_3$), 1.86 (s, 3H, Pyrazole-4-CH$_3$), 1.41 (d, J=6 Hz, 3H, CHCH$_3$).

Compound 11-1: melting point of 128.4° C. δ(CDCl3): 8.41 (s, 1H, Pyrimidine-H), 7.29-7.45 (m, 5H, Ph-5H), 6.21 (s, 1H, NH), 5.74 (s, 1H, Pyrazole-H), 4.40 (t, 2H, O—CH$_2$), 3.90 (m, 2H, N—CH$_2$), 3.72 (s, 3H, N—CH$_3$), 2.79 (m, 2H, CH$_2$), 1.27 (t, 3H, CH$_3$).

Compound 11-21: melting point of 135.9° C. δ(CDCl3): 8.45 (s, 1H, Pyrimidine-H), 7.72 (d, J=6 Hz, 1H, Ph-6-H), 7.43 (s, 1H, Ph-3-H), 7.25 (dd, J=6 Hz, 1H, Ph-5-H), 6.09 (s, Pyrazole-H), 5.73 (s, 1H, NH), 4.31 (t, J=6 Hz, 2H, O—CH$_2$), 3.96-3.99 (q, J=6 Hz, 2H, N—CH$_2$), 3.72 (s, 3H, N—CH$_3$), 2.79-2.83 (m, J=6 Hz, 2H, CH$_2$CH$_3$), 1.27 (t, J=6 Hz, 3H, CH$_2$CH$_3$).

Compound 11-34: oil. δ(CDCl3): 8.42 (s, 1H, Pyrimidine-H), 7.58 (m, 2H, Ph-2,6-2H), 7.26 (t, 2H, Ph-3,5-2H), 6.16 (s, 1H, NH), 5.73 (s, 1H, Pyrazole-H), 4.39 (t, 2H, O—CH$_2$), 3.89 (m, 2H, N—CH$_2$), 3.70 (s, 3H, N—CH$_3$), 2.80 (m, 2H, CH$_2$), 1.28 (t, 3H, CH$_3$).

Compound 11-69: melting point of 124.8° C. δ(CDCl3): 8.46 (s, 1H, Pyrimidine-H), 7.82 (d, J=6 Hz, 2H, Ph-2,6-2H), 7.62 (d, J=6 Hz, 2H, Ph-3,5-2H), 5.89 (s, 1H, Pyrazole-4-H), 5.73 (s, 1H, NH), 4.32 (t, J=6 Hz, 2H, O—CH$_2$), 3.97-4.00 (q, J=6 Hz, 2H, N—CH$_2$), 3.72 (s, 3H, N—CH$_3$), 2.79-2.83 (q, J=6 Hz, 2, CH$_2$CH$_3$), 1.27 (t, J=6 Hz, 3H, CH$_2$CH$_3$).

Compound 11-1-1: melting point of 92.9° C. δ(CDCl3): 8.42 (s, 1H, Pyrimidine-H), 7.45-7.47 (d, 2H, Ph-2,6-2H), 7.43 (t, 1H, Ph-4-H), 7.32 (t, 2H, Ph-3,5-2H), 6.43 (s, 1H, NH), 4.47 (t, 2H, O—CH$_2$), 3.89-3.94 (m, 2H, N—CH$_2$), 3.62 (s, 3H, N—CH$_3$), 2.75-2.83 (m, 2H, CH$_2$), 1.88 (s, 3H, Pyrazole-4-CH$_3$), 1.26 (t, 3H, CH$_3$).

Compound 11-1-2: oil. δ(CDCl3): 8.42 (s, 1H, Pyrimidine-H), 7.43 (m, 1H, Ph-6-H), 7.25 (m, 2H, Ph-3,4-211), 7.20 (m, 1H, Ph-5-H), 6.40 (s, 1H, NH), 4.47 (t, 2H, O—CH$_2$), 3.91 (m, 2H, N—CH$_2$), 3.58 (s, 3H, N—CH$_3$), 2.79 (in, 2, CH$_2$), 1.83 (s, 3H, Pyrazole-4-CH$_3$), 1.25 (t, 3H, CH$_3$).

Compound 11-1-3: oil. δ(CDCl3): 8.43 (s, 1H, Pyrimidine-H), 7.44 (m, 1H, Ph-6-H), 7.13 (m, 2H, Ph-2,5-2H), 7.02 (m, 1H, Ph-4-H), 6.38 (s, I-1, NH), 4.47 (t, 2-1, O—CH$_2$), 3.92 (m, 2H, N—CH$_2$), 3.63 (s, 3H, N—CH$_3$), 2.79 (m, 2H, CH$_2$), 1.88 (s, 3H, Pyrazole-4-CH$_3$), 1.27 (t, 3H, CH$_3$).

Compound 11-1-14: oil. δ (CDCl3): 8.43 (s, 1H, Pyrimidine-H), 7.25-7.29 (m, 2H, Ph-2,6-2H), 7.15-7.18 (t, 2-, Ph-3,5-2H), 6.41 (s, 1-H, NH), 4.47 (t, 2H, O—CH$_2$), 3.91 (m, 2H, N—CH$_2$), 3.60 (s, 3H, N—CH$_3$), 2.80 (m, 2H, CH$_2$), 1.85 (s, 3H, Pyrazole-4-CH$_3$), 1.26 (t, 3H, CH$_3$).

Compound 11-1-19: melting point of 113.5° C. δ(CDCl3): 8.43 (s, 1H, Pyrimidine-H), 7.45 (m, 2H, Ph-2,6-2H), 7.24 (t, 2H, Ph-3,5-211), 6.38 (s, 1H, NH), 4.46 (t, 2H, O—CH$_2$), 3.91 (m, 2H, N—CH$_2$), 3.61 (s, 3H, N—CH$_3$), 2.79 (m, 2H, CH$_2$), 1.86 (s, 3H, Pyrazole-4-CH$_3$), 1.25 (t, 3H, CH$_3$).

Compound 11-1-34: melting point of 85.3° C. δ(CDCl$_3$): 8.42 (s, 1H, Pyrimidine-H), 7.60 (d, 2H, Ph-2,6-2H), 7.18 (d, 2H, Ph-3,5-2H), 6.29 (s, 1H, NH), 4.46 (t, 2H, O—CH$_2$), 3.91 (m, 2H, N—CH$_2$), 3.61 (s, 3H, N—CH$_3$), 2.79 (m, 2H, CH$_2$), 1.86 (s, 3H, Pyrazole-4-CH$_3$), 1.25 (t, 3H, CH$_3$).

Compound 11-1-57: melting point of 134.0° C. δ(CDCl$_3$): 8.43 (s, 1H, Pyrimidine-H), 7.27 (m, 2H, Ph-2,6-2H), 7.20 (t, 2H, Ph-3,5-2H), 6.46 (s, 1H, NH), 4.47 (t, 2H, O—CH$_2$), 3.91 (m, 2H, N—CH$_2$), 3.61 (s, 3H, N—CH$_3$), 2.81 (m, 2H, CH$_2$), 2.42 (s, 3H, Ph-CH$_3$), 1.87 (s, 3H, Pyrazole-4-CH$_3$), 1.28 (t, 3H, CH$_3$).

Compound 11-1-66: oil. δ(CDCl3): 8.42 (s, 1H, Pyrimidine-H), 7.29 (d, 2H, Ph-2,6-2H), 7.22 (d, 2H, Ph-3,5-2H), 6.45 (s, 1H, NH), 4.47 (t, 2H, O—CH$_2$), 3.91 (m, 2H, N—CH$_2$), 3.62 (s, 3H, N—CH$_3$), 2.79 (m, 2H, CH$_2$), 2.72 (m, 2H, CH$_2$), 1.87 (s, 3H, Pyrazole-4-CH$_3$), 1.29 (t, 3H, CH$_3$), 1.25 (t, 3H, CH$_3$).

Compound 11-1-69: melting point of 99.3° C. δ(CDCl$_3$): 8.43 (s, 1H, Pyrimidine-H), 7.74 (d, 2H, Ph-2,6-2H), 7.45 (d, 2H, Ph-3,5-2H), 6.35 (s, 1H, NH), 4.48 (t, 2H, O—CH$_2$), 3.92 (m, 2H, N—CH$_2$), 3.62 (s, 3H, N—CH$_3$), 2.79 (m, 2H, CH$_2$), 1.88 (s, 3H, Pyrazole-4-CH$_3$), 1.25 (t, 3H, CH$_3$).

Compound 11-1-72: oil. δ(CDCl3): 8.42 (s, 1H, Pyrimidine-H), 7.23 (d, J=6 Hz, 2H, Ph-2,6-2), 6.99 (d, J=6 Hz, 2H, Ph-3,5-2H), 6.47 (s, 1H, NH), 4.47 (t, J=6 Hz, 2H, O—CH$_2$), 3.90-3.92 (q, J=6 Hz, 2H, N—CH$_2$), 3.86 (s, 3H, N—CH$_3$), 3.61 (s, 3H, OCH$_3$), 2.77-2.81 (q, J=6 Hz, 2H, CH$_2$CH$_3$), 1.86 (s, 3H, Pyrazole-4-CH$_3$), 1.26 (t, J=6 Hz, 3H, CH$_2$CH$_3$).

Compound 11-1-288: melting point of 105.9° C. δ(CDCl3): 8.43 (s, 1H, Pyrimidine-H), 7.47 (m, 2H, Ph-2,6-2H), 7.24 (t, 2H, Ph-3,5-2H), 6.45 (s, 1H, NH), 4.47 (t, 2H, O—CH$_2$), 3.91 (m, 2H, N—CH$_2$), 3.62 (s, 3H, N—CH$_3$), 2.79 (m, 2H, CH$_2$), 1.88 (s, 3H, Pyrazole-4-CH$_3$), 1.37 (s, 9H, C$_4$H$_9$), 1.25 (t, 3H, CH$_3$).

Compound 11-3-1: oil. δ(CDCl3): 8.42 (s, 1H, Pyrimidine-H), 7.47 (t, J=6 Hz, 2H, Ph-3,5-2H), 7.41 (t, J=6 Hz, 1H, Ph-4-H), 7.32 (d, J=6 Hz, 2H, Ph-2,6-2H), 6.23 (s, 1H, NH), 4.39 (t, J=6 Hz, 2H, O—CH$_2$), 3.71-3.74 (q, J=6 Hz, 2H, N—CH$_2$), 3.63 (s, 3H, N—CH$_3$), 2.77-2.80 (q, J=6 Hz, 2H, CH$_2$CH$_3$), 2.10-2.14 (m, 2H, CH$_2$), 1.90 (s, 3H, Pyrazole-4-CH$_3$), 1.26 (t, J=6 Hz, 3H, CH$_2$CH$_3$).

Compound 12-1: melting point of 91.6° C. δ(CDCl3): 8.59 (s, 1H, Pyrimidine-H), 7.67-7.74 (m, 2H, Ph-2,6-2H), 7.33-7.42 (m, 2H, Ph-3,5-2H), 7.25-7.31 (m, 1H, Ph-4-H), 6.73 (t, J=54 Hz, 1H, CHF$_2$), 6.06 (s, 1H, NH), 5.85 (s, 1H, Pyrazole-H), 4.31 (t, J=6 Hz, 2H, O—CH$_2$), 4.03 (m, 2H, NH—CH$_2$), 3.70 (s, 3H, N—CH$_3$).

Compound 12-21: melting point of 105.4° C. δ(CDCl3): 8.59 (s, 1H, Pyrimidine-H), 7.72 (d, J=6 Hz, 1H, Ph-6-H), 7.43 (s, 1H, Ph-3-H), 7.26 (dd, J=6 Hz, 1H, Ph-5-H), 6.73 (t, JHF=54 Hz, 1H, CHF$_2$), 6.10 (s, Pyrazole-4-H), 6.00 (s, 1H, NH), 4.33 (t, J=6 Hz, 2H, O—CH$_2$), 4.02-4.05 (q, J=6 Hz, 2H, N—CH$_2$), 3.72 (s, 3H, N—CH$_3$).

Compound 12-34: melting point of 107.0° C. δ(CDCl3): 8.55 (s, 1H, Pyrimidine-H), 7.44 (d, J=6 Hz, 2H, Ph-2,6-2H), 7.39 (d, J=6 Hz, 2H, Ph-3,5-2H), 6.73 (t, JHF=54 Hz, 1H, CHF$_2$), 6.70 (s, 1H, NH), 5.74 (s, 1H, Pyrazole-4-H), 4.44 (t, =6 Hz, 2H, O—CH$_2$), 3.94-3.97 (q, J=6 Hz, 2H, N—CH$_2$), 3.73 (s, 3H, N—CH$_3$).

Compound 12-69: melting point of 127.1° C. δ(CDCl3): 8.59 (s, 1H, Pyrimidine-H), 7.82 (d, J=6 Hz, 2H, Ph-2,6-2H), 7.62 (d, J=6 Hz, 2H, Ph-3,5-2H), 6.73 (t, JHF=54 Hz, 1H, CHF$_2$), 6.01 (s, 1H, NH), 5.89 (s, 1H, Pyrazole-4-H), 4.33 (t, J=6 Hz, 2H, O—CH$_2$), 4.03-4.06 (q, J=6 Hz, 2H, N—CH$_2$), 3.72 (s, 3H, N—CH$_3$).

Compound 12-1-1: δ(CDCl3): 8.55 (s, 1H, Pyrimidine-H), 7.45-7.48 (d, 2H, Ph-2,6-2H), 7.44 (t, 1H, Ph-4-H), 7.30 (t, 2H, Ph-3,5-2H), 7.02 (s, 1H, NH), 6.73 (s, 1H, CH), 4.51 (t, 2H, O—CH$_2$), 3.92-3.97 (m, 2H, N—CH$_2$), 3.62 (s, 3H, N—CH$_3$), 1.87 (s, 3H, Pyrazole-4-CH$_3$).

Compound 12-1-4: melting point of 88.8° C. δ(CDCl3): 8.55 (s, 1H, Pyrimidine-H), 7.28 (m, 2H, Ph-2,6-2H), 7.14 (m, 2H, Ph-3,5-2H), 7.01 (s, 1H, NH), 6.75 (s, J=54 Hz, 1H, CHF$_2$), 4.50 (t, J=6 Hz, 2H, O—CH$_2$), 3.95 (m, 2H, NH—CH$_2$), 3.60 (s, 3H, N—CH$_3$), 1.84 (s, 3H, Pyrazole-4-CH$_3$).

Compound 12-1-19: melting point of 100.6° C. δ(CDCl3): 8.56 (s, 1H, Pyrimidine-H), 7.48 (d, J=6 Hz, 2H, Ph-2,6-2H), 7.25 (d, J=6 Hz, 2H, Ph-3,5-2H), 6.96 (s, 1H, NH), 6.73 (t, J=54 Hz, 1H, CHF$_2$), 4.49 (t, J=6 Hz, 2H, O—CH$_2$), 3.95 (m, 2H, NH—CH$_2$), 3.61 (s, 3H, N—CH$_3$), 1.86 (s, 3H, Pyrazole-4-CH$_3$).

Compound 12-1-57: oil. δ(CDCl3): 8.55 (s, 1H, Pyrimidine-H), 7.27 (d, J=6 Hz, 2H, Ph-2,6-2H), 7.19 (d, J=6 Hz, 2H, Ph-3,5-2H), 7.06 (s, 1H, NH), 6.73 (t, JHF=54 Hz, 1H, CH), 4.51 (t, J=6 Hz, 2H, O—CH$_2$), 3.93-3.95 (q, J=6 Hz, 2H, N—CH$_2$), 3.61 (s, 3H, N—CH$_3$), 2.42 (s, 3H, Ph-4-CH$_3$), 1.86 (s, 3H, Pyrazole-4-CH$_3$).

Compound 12-1-72: oil. δ(CDCl3): 8.55 (s, 1H, Pyrimidine-H), 7.22 (d, J=6 Hz, 2H, Ph-2,6-2H), 7.06 (s, 1H, NH), 6.99 (d, J=6 Hz, 2H, Ph-3,5-2H), 6.73 (t, JHF=54 Hz, 1H, CHF$_2$), 4.50 (t, J=6 Hz, 2H, O—CH$_2$), 3.93-3.95 (q, J=6 Hz, 2H, N—CH$_2$), 3.86 (s, 3H, N—CH$_3$), 3.60 (s, 3H, OCH$_3$), 1.86 (s, 3H, Pyrazole-4-CH$_3$).

Compound 12-1-288: melting point of 90.8° C. δ(CDCl3): 8.55 (s, 1H, Pyrimidine-H), 7.48 (d, J=6 Hz, 2H, Ph-2,6-2H), 7.24 (d, J=6 Hz, 2H, Ph-3,5-2H), 7.07 (s, 1H, NH), 6.73 (t, J=54 Hz, 1H, CHF$_2$), 4.51 (t, J=6 Hz, 2H, O—CH$_2$), 3.95 (m, 2H, NH—CH$_2$), 3.62 (s, 3H, N—CH$_3$), 1.88 (s, 3H, Pyrazole-4-CH$_3$), 1.37 (s, 9H, C$_4$H$_9$).

Compound 12-2-19: oil. δ(CDCl3): 8.54 (s, 1H, Pyrimidine-H), 7.45 (d, J=6 Hz, 2H, Ph-2,6-2H), 7.25 (d, J=6 Hz, 2H, Ph-3,5-2H), 6.72 (t, J=54 Hz, 1H, CHF$_2$), 6.69 (s, 1H, NH), 4.40 (t, J=6 Hz, 2H, O—CH$_2$), 3.78 (m, 2H, N—CH$_2$), 3.61 (s, 3H, N—CH$_3$), 2.12 (m, 2H, CH$_2$), 1.87 (s, 3H, Pyrazole-4-CH$_3$).

Compound 12-3-1: yellow oil. δ(CDCl3): 8.54 (s, 1H, Pyrimidine-H), 7.48 (t, J=6 Hz, 2H, Ph-3,5-2H), 7.42 (t, J=6 Hz, 1H, Ph-4-H), 7.32 (d, J=6 Hz, 2H, Ph-2,6-2H), 6.75 (s, 1H, NH), 6.73 (t, JHF=54 Hz, 1H, CHF$_2$), 4.41 (t, J=6 Hz, 2H, O—CH$_2$), 3.77-3.80 (q, J=6 Hz, 2H, N—CH$_2$), 3.63 (s, 3H, N—CH$_3$), 2.10-2.14 (m, 2H, CH$_2$), 1.89 (s, 3H, Pyrazole-4-CH$_3$).

Compound 12-4-1: oil. δ(CDCl3): 8.46 (s, 1H, Pyrimidine-H), 7.47 (t, J=6 Hz, 2H, Ph-3,5-2H), 7.41 (t, J=6 Hz, 1H, Ph-4-H), 7.32 (d, J=6 Hz, 21, Ph-2,6-2H), 7.04 (s, 1H, Thiophene-H), 6.89 (s, 1H, NH), 4.40 (t, J=6 Hz, 2H, O—CH$_2$), 3.85-3.88 (q, J=6 Hz, 2H, N—CH$_2$), 3.61 (s, 3H, N—CH$_3$), 2.19-2.23 (m, 2H, CH$_2$), 1.87 (s, 3H, Pyrazole-4-CH$_3$).

Compound 19-69: melting point of 175.9° C. δ(CDCl3): 8.71 (s, 1H, Quinazoline-3-H), 7.89 (d, J=6 Hz, 1H, Quinazoline-5-H), 7.79 (d, =6 Hz, 2H, Ph-2,6-2H), 7.77 (t, J=6 Hz, 1H, Quinazoline-6-H), 7.72 (d, J=6 Hz, 1H, Quinazoline-8-H), 7.61 (d, J=6 Hz, 2H, Ph-3,5-2H), 7.50 (t, J=6 Hz, 1H, Quinazoline-7-H), 6.07 (s, 1H, NH), 5.91 (s, 1H, Pyrazole-4-H), 4.43 (t, J=6 Hz, 2H, O—CH$_2$), 4.15-4.18 (q, J=6 Hz, 2H, N—CH$_2$), 3.73 (s, 3H, N—CH$_3$).

Compound 19-1-4: melting point of 213.8° C. δ(CDCl3): 8.68 (s, 1H, Quinazoline-3-H), 7.86 (m, 1H, Quinazoline-5-H), 7.71 (m, 1H, Quinazoline-8-H), 7.53 (d, J=6 Hz, 1H, Quinazoline-6-H), 7.51 (s, 1H, NH), 7.44 (d, J=6 Hz, 1H, Quinazoline-7-H), 7.28 (d, J=6 Hz, 2H, Ph-2,6-2H), 7.18 (d, J=6 Hz, 2H, Ph-3,5-2H), 4.60 (t, J=6 Hz, 2H, O—CH$_2$), 4.05 (q, J=6 Hz, 2H, N—CH$_2$), 3.68 (s, 3H, N—CH$_3$), 1.87 (s, 3H, Pyrazole-4-CH$_3$).

Compound 19-1-19: melting point of 189.5° C. δ(CDCl3): 8.68 (s, 1H, Quinazoline-3-H), 7.84 (m, 2H, Quinazoline-5,8-2H), 7.72 (m, 1H, Ph-8-H), 7.47 (m, 3H, Quinazoline-6-H+Ph-2,6-2H), 7.24 (m, 2H, Ph-3,5-2H), 6.38 (s, 1H, NH), 4.59 (t, J=6 Hz, 2H, O—CH$_2$), 4.04 (m, 2H, NH—CH$_2$), 3.68 (s, 3H, N—CH$_3$), 1.87 (s, 3H, Pyrazole-4-CH$_3$).

Compound 19-1-57: melting point of 148.7° C. δ(CDCl3): 8.68 (s, 1H, Quinazoline-3-H), 7.88 (d, J=12 Hz, 1H, Quinazoline-5-H), 7.85 (d, J=6 Hz, 1H, Quinazoline-8-H), 7.72 (m, 1H, Quinazoline-6-H), 7.69 (s, 1H, NH), 7.44 (d, J=6 Hz, 1H, Quinazoline-7-H), 7.28 (d, J=6 Hz, 2H, Ph-2,6-2H), 7.20 (d, J=6 Hz, 2H, Ph-3,5-2H), 4.60 (t, J=6 Hz, 2H, O—CH$_2$), 4.04 (q, J=6 Hz, 2H, N—CH$_2$), 3.70 (s, 3H, N—CH$_3$), 2.42 (s, 3H, CH$_3$), 1.88 (s, 3H, Pyrazole-4-CH$_3$).

Compound 19-1-72: oil. δ(CDCl3): 8.67 (s, 1H, Quinazoline-3-H), 7.88 (d, J=12 Hz, 1H, Quinazoline-5-H), 7.85 (d, J=6 Hz, 1H, Quinazoline-8-H), 7.73 (m, 1H, Quinazoline-6-H), 7.63 (s, 1H, NH), 7.44 (d, J=6 Hz, 1H, Quinazoline-7-H), 7.23 (d, J=6 Hz, 2H, Ph-2,6-2H), 7.01 (d, J=6 Hz, 2H, Ph-3,5-2H), 4.60 (t, J=6 Hz, 2H, O—CH$_2$), 4.03-4.05 (q, J=6 Hz, 2H, N—CH$_2$), 3.87 (s, 3H, N—CH$_3$), 3.69 (s, 3H, OCH$_3$), 1.87 (s, 3H, Pyrazole-4-CH$_3$).

Compound 19-1-288: oil. δ(CDCl3): 8.67 (s, 1H, Quinazoline-3-H), 7.87 (m, 2H, Quinazoline-5,8-2H), 7.72 (m, 1H, Ph-8-H), 7.65 (s, 1H, NH), 7.48 (m, 2H, Ph-2,6-2H), 7.43 (m, 1H, Quinazoline-6-H), 7.24 (in, 2H, Ph-3,5-2H), 4.61 (t, J=6 Hz, 2H, O—CH$_2$), 4.04 (m, 2H, NH—CH$_2$), 3.72 (s, 3H, N—CH$_3$), 1.90 (s, 3H, Pyrazole-4-CH$_3$), 1.37 (s, 9H, C$_4$H$_9$).

Compound 19-3-1: melting point of 109.6° C. δ(CDCl3): 8.66 (s, 1H, Quinazoline-3-H), 7.88 (d, J=6 Hz, 1H, Quinazoline-5-H), 7.84 (d, J=6 Hz, 1H, Quinazoline-8-H), 7.72 (t, J=6 Hz, 1H, Quinazoline-6-H), 7.48 (t, J=6 Hz, 2H, Ph-3,5-2H), 7.43 (m, 2H, Ph-4-H+Quinazoline-7-H), 7.32 (d, J=6 Hz, 2H, Ph-2,6-2H), 7.12 (s, 1H, NH), 4.48 (t, J=6 Hz, 2H, O—CH$_2$), 3.88-3.91 (q, 2H, N—CH$_2$), 3.67 (s, 3H, N—CH$_3$), 2.19-2.23 (m, 2H, CH$_2$), 1.92 (s, 3H, Pyrazole-4-H).

Compound 19-4-1: oil. δ(CDCl3): 8.66 (s, 1H, Quinazoline-3-H), 7.84 (d, P=6 Hz, 1H, Quinazoline-5-H), 7.82 (d, J=6 Hz, 1H, Quinazoline-8-H), 7.71 (t, J=6 Hz, 1H, Quinazoline-6-H), 7.47 (t, J=6 Hz, 2H, Ph-3,5-2H), 7.41 (t, J=6 Hz, 2. Ph-4-H, Quinazoline-7-H), 7.40 (s, 1H, NH), 7.29 (d, J=6 Hz, 2H, Ph-2,6-2H), 4.76-4.79 (m, 1H, N—CH), 4.47 (d, J=6 Hz, 2H, O—CH$_2$), 3.69 (s, s, 3H, N—CH$_3$), 1.87 (s, 3H, Pyrazole-4-CH$_3$), 1.48 (d, J=6 Hz, 3H, CH$_2$CH$_3$).

Compound 21-1: melting point of 136.8° C. δ(CDCl3): 8.50 (s, 1H, Pyrimidine-H), 7.68-7.73 (m, 2H, Ph-2,6-2H), 7.37 (m, 2H, Ph-3,5-2H), 7.26-7.30 (m, 1H, Ph-4-H), 7.11 (s, 1H, Thiophene-H), 6.91 (s, 1H, NH), 5.87 (s, 1H, Pyrazole-H), 4.37 (t, J=6 Hz, 2H, O—CH$_2$), 4.11 (m, 2H, NH—CH$_2$), 3.72 (s, 3H, N—CH$_3$).

Compound 21-21: melting point of 123.8° C. δ(CDCl3): 8.49 (s, 1H, Pyrimidine-H), 7.72 (d, J=6 Hz, 1H, Ph-6-H), 7.43 (s, 1H, Ph-3-H), 7.26 (dd, J=6 Hz, 1H, Ph-5-H), 7.11 (s, 1H, Thiophene-H), 6.90 (s, 1H, NH), 6.11 (s, Pyrazole-4-H), 4.37 (t, J=6 Hz, 2H, O—CH$_2$), 4.09-4.12 (q, J=6 Hz, 2H, N—CH$_2$), 3.72 (s, 3H, N—CH$_3$).

Compound 21-34: oil. δ(CDCl3): 8.47 (s, 1H, Pyrimidine-H), 7.44 (d, J=6 Hz, 2H, Ph-2,6-2H), 7.39 (d, 2H, Ph-3,5-2H), 7.07 (s, 1H, Thiophene-H), 7.00 (s, 1H, NH), 5.75 (s, 1H, Pyrazole-4-H), 4.44 (t, J=6 Hz, 2H, O—CH$_2$), 4.03-4.08 (q, J=6 Hz, 2H, N—CH$_2$), 3.72 (s, 3H, N—CH$_3$).

Compound 21-69: melting point of 177.3° C. δ(CDCl3): 8.50 (s, 1H, Pyrimidine-H), 7.82 (d, J=6 Hz, 2H, Ph-2,6-2H), 7.62 (d, J=6 Hz, 2H, Ph-3,5-2H), 7.11 (s, 1H, Thiophene-H), 6.89 (s, 1H, NH), 5.91 (s, 1H, Pyrazole-4-H), 4.38 (t, J=6 Hz, 2H, O—CH$_2$), 4.10-4.13 (q, J=6 Hz, 2H, N—CH$_2$), 3.73 (s, 3H, N—CH$_3$).

Compound 21-1-4: melting point of 148.2° C. δ(CDCl3): 8.47 (s, 1H, Pyrimidine-H), 7.30 (m, 2H, Ph-2,6-2H), 7.16 (m, 2H, Ph-3,5-2H), 7.06 (s, 2H, Thiophene-H+NH), 4.50 (t, J=6 Hz, 2H, O—CH$_2$), 4.06 (m, 2H, NH—CH$_2$), 3.58 (s, 3H, N—CH$_3$), 1.85 (s, 3H, Pyrazole-4-CH$_3$).

Compound 21-1-19: melting point of 161.2° C. δ(CDCl3): 8.47 (s, 1H, Pyrimidine-H), 7.45 (d, J=6 Hz, 2H, Ph-2,6-2H), 7.23 (d, J=6 Hz, 2H, Ph-3,5-2H), 7.06 (s, 1H, Thiophene-H), 7.05 (s, 1H, NH), 4.50 (t, J=6 Hz, 2H, O—CH$_2$), 4.06 (m, 2H, NH—CH$_2$), 3.58 (s, 3H, N—CH$_3$), 1.86 (s, 3H, Pyrazole-4-CH$_3$).

Compound 21-1-57: melting point of 149.3° C. δ(CDCl$_3$): 8.47 (s, 1H, Pyrimidine-H), 7.27 (d, J=6 Hz, 2H, Ph-2,6-2H), 7.19 (d, J=6 Hz, 2H, Ph-3,5-2H), 7.07 (s, 1H, NH), 7.05 (s, 1H, Pyrazole-H), 4.50 (t, J=6 Hz, 2H, O—CH$_2$), 4.06 (m, 2H, NH—CH$_2$), 3.59 (s, 3H, N—CH$_3$), 2.41 (s, 3H, Ph-CH$_3$), 1.87 (s, 3H, Pyrazole-CH$_3$).

Compound 21-1-288: melting point of 169.3° C. δ(CDCl3): 8.48 (s, 1H, Pyrimidine-H), 7.47 (d, J=6 Hz, 2H, Ph-2,6-2H), 7.23 (d, J=6 Hz, 2H, Ph-3,5-2H), 7.09 (s, 1H, Thiophene-H), 7.06 (s, 1H, NH), 4.51 (t, J=6 Hz, 2H, O—CH$_2$), 4.06 (m, 2H, NH—CH$_2$), 3.61 (s, 3H, N—CH$_3$), 1.88 (s, 3H, Pyrazole-4-CH$_3$), 1.35 (s, 9H, C$_4$H$_9$).

Compound 21-3-1: melting point of 109.0° C. δ(CDCl3): 8.54 (s, 1H, Pyrimidine-H), 7.47 (t, J=6 Hz, 2H, Ph-3,5-2H), 7.420 (t, J=6 Hz, 1H, Ph-4-H), 7.31 (d, J=6 Hz, 2H, Ph-2,6-2H), 6.85 (s, 1H, NH), 6.72 (t, JHF=54 Hz, 1H, CHF$_2$), 4.63-4.65 (m, 1H, N—CH), 4.38 (d, J=6 Hz, 2H, O—CH$_2$), 3.61 (s, 3H, N—CH$_3$), 1.86 (s, 3H, Pyrazole-4-CH$_3$), 1.41 (d, J=6 Hz, 3H, CHCH$_3$).

Compound 21-4-1: melting point of 149.3° C. δ(CDCl3): 8.46 (s, 1H, Pyrimidine-H), 7.46 (t, J=6 Hz, 2H, Ph-3,5-2H), 7.41 (t, J=6 Hz, 1H, Ph-4-H), 7.29 (d, J=6 Hz, 2H, Ph-2,6-2H), 7.04 (s, 1H, Thiophene-H), 6.91 (s, 1H, NH), 4.84-4.86 (m, 1H, N—CH), 4.39 (d, J=6 Hz, 2H, O—CH$_2$), 3.59 (s. 3H, N—CH$_3$), 1.87 (s, 3H, Pyrazole-4-CH$_3$), 1.48 (d, J=6 Hz, 3H, CHCH$_3$).

Compound 26-1-1: oil. δ(CDCl3): 1H-NMR (600 MHz, internal standard TMS, solvent CDCl3) δ(ppm): 8.42 (s, 1H, Pyrimidine-H), 7.46 (t, J=6 Hz, 2H, Ph-3,5-2H), 7.41 (t, J=6 Hz, 1H, Ph-4-H), 7.29 (d, J=6 Hz, 2H, Ph-2,6-2H), 4.51 (t, 2H, O—CH$_2$), 4.40 (t, 2H, CH$_2$—O), 3.58 (s, 3H, Pyrazole-N—CH$_3$), 2.75-2.78 (q, J=6 Hz, 2H, CH$_2$CH$_3$), 1.81 (s, 3H, Pyrazole-4-CH$_3$), 1.26 (t, J=6 Hz, 3H, CH$_2$CH$_3$).

Meanwhile, other compounds shown by the general formula I of the present invention can be obtained by replacing the corresponding raw materials according to the content recorded in the above synthesis embodiments.

In addition, the above obtained compounds react with acid in a conventional manner to obtain corresponding salt.

Embodiment of Determination of Biological Activity

The compound of the present invention shows good activity against various fungi, pests and mites in the agricultural field.

Embodiment 14: Determination of Fungicidal Activity

In vitro inhibition activity or in vivo protective effect test is conducted on various fungal diseases of the plant by using the compound sample of the present invention. The determination results of fungicidal activity are shown in the following embodiments.

(1) Determination of In Vitro Fungicidal Activity

The determination method is as follows: a high-throughput screening method is adopted, that is, a sample of the compound to be tested is dissolved with a suitable solvent (the type of the solvent may be, for example, acetone, methanol and DMF, and selected according to the capability to dissolve the sample) and formulated into a required concentration of solution to be tested. In an ultra-clean working environment, the solution to be tested is added into micro-wells of a 96-well culture plate, and a pathogen propagator suspension is added thereto, and the treated culture plate is placed in a constant temperature incubator for cultivation. An investigation is conducted after 24 hours; during the investigation, the germination or growth of a pathogen propagator is visually observed, and the fungicidal activity of the compound is evaluated according to the germination or growth of the control treatment.

The test results of the in vitro fungicidal activity (represented by the inhibition activity) of part of compounds are as follows:

Inhibition Activity for Rice Blast:

At a dose of 25 ppm, the compounds provided by the present invention have a good inhibition activity for rice blast; for example, compounds 10-1-19, 10-1-72, 10-3-1, 11-1-1, 11-1-72, 11-3-1, 12-1-1, 12-1-4, 12-1-57, 12-3-1, 19-1-4, 19-1-19, 19-1-57, 19-1-72, 19-3-1, 19-34, 12-1-19, 21-1-4, 21-1-19, 21-3-1 and 21-34 have the inhibition activity of more than 80% for the rice blast; and control agents CK1, CK2, CK3, CK4 and CK5 have an inhibition activity of 0 for the rice blast.

If the dose is further reduced, at a dose of 8.3 ppm, the compounds provided by the present invention still have a good inhibition activity for the rice blast; for example, compounds 10-1-72, 10-3-1, 11-1-72, 11-3-1, 12-1-4, 112-3-1, 19-1-4, 19-1-19, 19-1-57, 19-1-72, 19-3-1, 12-1-19, 21-1-4, 21-1-19, 21-3-1 and 21-34 have the inhibition activity of more than 80% for the rice blast; and control agents CK1, CK2, CK3, CK4 and CK5 have an inhibition activity of 0 for the rice blast.

If the dose is still further reduced, at a dose of 2.8 ppm, the compounds provided by the present invention still have a good inhibition activity for the rice blast; for example, compounds 10-3-1, 12-3-1, 19-1-4, 19-1-19, 19-3-1, 12-1-19 and 21-34 have the inhibition activity of more than 80% for the rice blast; and control agents CK1, CK2, CK3, CK4 and CK5 have an inhibition activity of 0 for the rice blast.

(2) Determination of In Vivo Protective Activity

The determination method is as follows: an in vivo pot determination method is adopted, i.e., a sample of the compound to be tested is dissolved with a small amount of solvent (the type of the solvent may be, for example, acetone, methanol and DMF, and selected according to the capability to dissolve the sample; the volume ratio of the amount of the solvent to the amount of sprayed solution is equal to or less than 0.05), diluted with water containing 0.1% Tween 80 and formulated into a required concentration of solution to be tested. On a crop sprayer, the solution to be tested is sprayed on a disease host plant (the host plant is a standard potted seedling cultivated in a greenhouse), and then the disease is inoculated after 24 hours. According to the characteristics of the disease, the diseased plant which requires temperature control and moisture cultivation is inoculated and cultivated in an artificial climate room. After the infection is completed for the disease, the disease is transferred into the greenhouse for cultivation, and the diseased plant which requires no moisture cultivation is directly inoculated and cultivated in the greenhouse. After the control is fully diseased (generally one week), the disease prevention effect of the compound is evaluated.

The test results of the in vivo protective activity of part of compounds are as follows:

(1) Cucumber Downy Mildew

At a dose of 400 ppm, the compounds provided by the present invention have a good inhibition activity for controlling cucumber downy mildew; for example, compounds 10-1, 10-1-4, 10-1-19, 10-1-57, 10-1-72, 10-3-1, 10-4-1, 10-21, 10-34, 10-69, 11-1, 11-1-1, 11-1-4, 11-1-19, 11-1-72, 11-3-1, 11-4-1, 11-21, 11-69, 12-1, 12-1-1, 12-1-4, 12-1-19, 12-1-57, 12-1-72, 12-2-19, 12-3-1, 12-4-1, 12-21, 12-34, 12-69, 19-1, 19-1-4, 19-1-19, 19-1-57, 19-1-72, 19-3-1, 19-4-1, 19-34, 21-1, 21-1-4, 21-1-19, 21-1-57, 21-1-72, 21-3-1, 21-4-1, 21-34 and 26-1-1 have a protective effect of more than 80% for the cucumber downy mildew.

If the dose is further reduced, at a dose of 100 ppm, the compounds provided by the present invention have a good inhibition activity for the cucumber downy mildew; for example, compounds 10-1-4, 10-1-19, 10-4-1, 11-1-1, 11-1-4, 11-4-1, 12-1-1, 12-1-4, 12-1-19, 12-1-57, 12-4-1, 12-21, 12-34, 19-1-4, 19-1-19, 19-1-57, 19-1-72, 19-4-1 and 26-1-1 have a protective effect of more than 80% for controlling cucumber downy mildew.

If the dose is still further reduced, at a dose of 25 ppm, the compounds provided by the present invention have a good inhibition activity for the cucumber downy mildew; for example, compounds 10-1-4, 10-1-19, 10-4-1, II-1-1, 11-1-4, 11-4-1, 12-1-1, 12-14, 12-1-19, 12-1-57, 12-4-1, 12-34, 19-1-4, 19-1-19, 19-1-57, 19-1-72 and 26-1-1 have a protective effect of more than 80% for controlling cucumber downy mildew.

If the dose is more further reduced, at a dose of 6.25 ppm, the compounds provided by the present invention have a good inhibition activity for the cucumber downy mildew; for example, compounds 10-1-4, 10-1-19, 11-1-1, 11-1-4, 12-1-4, 12-1-19, 19-1-4, 19-1-19, 19-1-57, 19-1-72 and 26-1-1 have a protective effect of more than 80% for controlling cucumber downy mildew.

The protective effects of CK1, CK2, CK3, CK4 and CK5 for controlling cucumber downy mildew are as follows:

| Compound No. | Protective Activity (%) | | | |
|---|---|---|---|---|
| | 400 mg/L | 100 mg/L | 50 mg/L | 25 mg/L |
| CK1 | 100 | 95 | 20 | 0 |
| CK2 | 100 | 75 | 20 | 0 |
| CK3 | 100 | 30 | 0 | /// |
| CK4 | 100 | 40 | 0 | /// |
| CK5 | 85 | /// | /// | /// |

"///" represents untested; the same below (2) Wheat Powdery Mildew

At a dose of 400 ppm, the compounds provided by the present invention have a good inhibition activity for control of wheat powdery mildew; for example, compounds 10-1-19, 10-1-57, 10-1-72, 10-3-1, 10-4-1, 11-1, 11-1-4, 11-1-19, 11-1-72, 11-1-288, 11-3-1, 11-4-1, 11-69, 12-1-4, 12-1-19, 12-1-57, 12-1-72, 12-1-288, 12-3-1, 12-4-1, 12-34, 12-69, 19-1-4, 19-1-19, 19-1-72, 19-21, 21-1-19, 21-1-72, 21-3-1 and 21-4-1 have a protective effect of more than 80% for control of wheat powdery mildew.

If the dose is further reduced, at a dose of 100 ppm, the compounds provided by the present invention have a good inhibition activity for the wheat powdery mildew; for example, compounds 10-1-72, 10-4-1, 11-1-4, 11-1-19, 11-1-72, 12-1-4, 12-1-19, 12-1-57, 12-1-72, 12-3-1, 12-4-1 and 21-1-19 have a protective effect of more than 80% for control of wheat powdery mildew.

If the dose is still further reduced, at a dose of 25 ppm, the compounds provided by the present invention have a good inhibition activity for control of wheat powdery mildew; for example, compounds 10-1-19, 11-1-19, 12-1-4, 12-1-19 and 21-1-19 have a protective effect of more than 80% for control of wheat powdery mildew.

If the dose is further reduced, at a dose of 6.25 ppm, the compounds provided by the present invention have a good inhibition activity for control of wheat powdery mildew; for example, compounds 12-1-19 and the like have a protective effect of more than 80% for control of wheat powdery mildew.

The protective effects of CK2, CK3, CK4 and CK5 for the wheat powdery mildew are as follows:

| Compound No. | Protective Activity (%) | | | |
|---|---|---|---|---|
| | 400 mg/L | 100 mg/L | 25 mg/L | 6.25 mg/L |
| CK2 | 100 | 50 | 20 | 0 |
| CK3 | 0 | /// | /// | /// |
| CK4 | 0 | /// | /// | /// |
| CK5 | 0 | /// | /// | /// |

(3) Corn Rust

At a dose of 400 ppm, the compounds provided by the present invention have a good inhibition activity for control of corn rust; for example, compounds 10-1-4, 10-1-19, 10-1-57, 10-1-72, 10-3-1, 10-4-1, 11-1, 11-1-1, 11-1-4, 11-1-72, 11-1-288, 11-3-1, 11-4-1, 12-1-1, 12-1-4, 12-1-19, 12-1-57, 12-1-72, 12-1-288, 12-3-1, 12-4-1, 19-1-4, 19-1-19, 19-1-72, 19-1-288, 19-3-1, 19-34, 21-1-4, 12-1-19, 21-1-19, 21-1-57, 21-1-72, 21-3-1 and 21-4-1 have a protective effect of more than 80% for control of corn rust.

If the dose is further reduced, at a dose of 100 ppm, the compounds provided by the present invention have a good inhibition activity for control of corn rust; for example, compounds 10-1-4, 10-1-19, 10-1-57, 10-1-72, 10-4-1, 11-1, 11-1-1, 11-1-4, 11-1-72, 11-3-1, 12-1-4, 12-1-19, 12-1-57, 12-1-72, 12-1-288, 12-3-1, 19-1-19, 19-1-72, 19-1-288, 21-1-4, 12-1-19, 21-1-19 and 21-1-57 have a protective effect of more than 80% for control of corn rust.

If the dose is still further reduced, at a dose of 25 ppm, the compounds provided by the present invention have a good inhibition activity for control of corn rust; for example, compounds 11-1-1, 11-1-4, 11-1-72, 12-1-4, 12-1-19, 12-1-72, 19-1-19 and 21-1-57 have a protective effect of more than 80% for control of corn rust.

If the dose is more further reduced, at a dose of 6.25 ppm, the compounds provided by the present invention have a good inhibition activity for control of corn rust; for example, compounds 11-1-1, 11-1-72, 12-1-4, 12-1-19, 12-1-72 and 21-1-57 have a protective effect of more than 80% for control of corn rust.

The protective effects of CK3, CK4 and CK5 for the corn rust are as follows:

| Compound No. | Protective Activity (%) | | | |
|---|---|---|---|---|
| | 400 mg/L | 100 mg/L | 25 mg/L | 6.25 mg/L |
| CK3 | 60 | 20 | 0 | 0 |
| CK4 | 40 | 0 | 0 | 0 |
| CK5 | 98 | 70 | 60 | 20 |

(4) Cucumber Anthrax

At a dose of 400 ppm, the compounds provided by the present invention have a good inhibition activity for control of melon anthrax; for example, compounds 10-21, 11-1-19, 12-1-1, 12-1-19, 12-4-1, 12-2-19, 19-1-4, 19-1-57, 19-4-1, 21-1-4, 21-4-1, 21-21 and 26-1-1 have a protective effect of 100% for the melon anthrax. The control agents CK3, CK4 and CK5 have a protective effect of 0 for control of cucumber anthrax.

It can be seen from the above data that the compound having novel structure shown by the general formula I in the present invention shows good activity against various fungi in the agricultural field. Moreover, at some low doses, the compounds show outstanding activity effects, which are better than the control compounds.

Embodiment 15: Determination of Insecticidal and Acaricidal Activity

Determination tests of insecticidal activity are conducted on several insects by using the compound of the present invention. The determination method is as follows:

The compound to be tested is dissolved with a mixed solvent of acetone/methanol (1:1 (v/v)), and then diluted with the water containing 0.1% (wt) Tween 80 to a required concentration.

Taking green peach aphid and *Tetranychus cinnabarinus* as targets, the insecticidal activity is determined through the airbrush spray method.

(1) Determination of Activity Against the Green Peach Aphid

Determination method: a petri dish with a diameter of 6 cm is taken; a layer of filter paper is covered on the bottom of the petri dish; and a proper amount of tap water is dripped for moisture retention. Cabbage leaves, on which 15-30 aphids exist, with a suitable size (about 3 cm in diameter) are cut from cabbage plants that culture the green peach aphid. Alatae and the aphids on the front surface of the leaves are removed. The leaves are placed in the petri dish in a manner of backing on to the petri dish. The pressure of spraying by airbrush is 10 psi (about 0.7 kg/cm2) and a spray volume is 0.5 ml. The test is repeated for 3 times. After treatment, the cabbage leaves are cultivated in an observation room at 25° C. and relative humidity of 60%-70%. After 48 hours, the number of surviving aphids is investigated, and the mortality is calculated At a dose of 600 ppm, the compounds provided by the present invention have a good inhibition activity for the green peach aphid; for example, compounds 10-4-1, 11-1, 11-34, 11-1-1, 11-1-4, 11-1-19, 11-1-57, 11-1-72, 11-3-1, 12-1-19, 12-1-57, 12-1-72, 12-3-1 and 12-4-1 have a lethality of more than 80% for the green peach aphid.

If the dose is further reduced, at a dose of 100 ppm, the compounds provided by the present invention have a good inhibition activity for the green peach aphid; for example, compounds 11-1-4, 12-1-57 and 11-1-1 have a lethality of more than 80% for the green peach aphid. The lethality of CK1, CK3, CK4 and CK5 for the green peach aphid is as follows:

| Compound No. | Lethality to Green Peach Aphid (%) 100 mg/L |
|---|---|
| CK1 | 0 |
| CK3 | 30 |
| CK4 | 0 |
| CK5 | 22 |

(2) Determination of Activity Against the *Tetranychus cinnabarinus*

Determination method: two pieces of euphylla bean sprouts are taken; and inoculated with *Tetranychus cinnabarinus* adults; and the base number is investigated. The whole plant is sprayed with the airbrush atomizer. The pressure is 10 psi (about 0.7 kg/cm2) and a spray volume is 0.5 ml. The test is repeated for 3 times. After treatment, the sprouts are placed in a standard observation room. After 72 hours, the number of surviving *Tetranychus cinnabarinus* adults is investigated, and the mortality is calculated.

Part of Test Results for the *Tetranychus cinnabarinus* are as Follows:

At a dose of 600 ppm, the compounds provided by the present invention have a good inhibition activity for the *Tetranychus cinnabarinus*; for example, compounds 10-1-72, 10-3-1, 10-4-1, 11-1, 11-34, 11-1-1, 11-1-4, 11-1-19, 11-1-57, 11-1-72, 11-3-1, 11-4-1, 11-21, 12-1, 12-1-1, 12-1-4, 12-1-19, 12-1-57, 12-1-72, 12-3-1, 12-4-1, 19-1-19, 19-1-57, 19-1-72, 19-3-1, 21-1, 21-1-57, 21-1-72 and 21-34 have a lethality of more than 80% for the *Tetranychus cinnabarinus*.

If the dose is further reduced, at a dose of 100 ppm, the compounds provided by the present invention have a good inhibition activity for the *Tetranychus cinnabarinus*; for example, compounds 10-1-72, 10-4-1, 11-1, 11-34, 11-1-1, 11-1-4, 11-1-19, 11-1-57, 11-1-72, 11-3-1, 11-4-1, 12-1-1, 12-1-4, 12-1-19, 12-1-57, 12-1-72, 12-3-1, 12-4-1, 19-1-19, 19-1-57, 19-1-72, 19-3-1, 21-1-57 and 21-1-72 have a lethality of more than 80% for the *Tetranychus cinnabarinus*.

If the dose is still further reduced, at a dose of 10 ppm, the compounds provided by the present invention have a good inhibition activity for the *Tetranychus cinnabarinus*; for example, compounds 11-1-1, 11-1-4, 11-1-19, 11-1-57, 11-1-72, 11-4-1, 12-1-4, 12-1-19, 12-1-57, 19-1-19, 21-1-57 and 21-1-72 have a lethality of more than 80% for the *Tetranychus cinnabarinus*.

If the dose is more further reduced, at a dose of 2.5 ppm, the compounds provided by the present invention have a good inhibition activity for the *Tetranychus cinnabarinus*; for example, compounds 11-1-4, 11-1-19, 11-1-57, 11-1-72 and 1-4-1 have a lethality of more than 80% for the *Tetranychus cinnabarinus*.

The lethality of CK3, CK4 and CK5 for the *Tetranychus cinnabarinus* is as follows:

| Compound No. | Lethality to Tetranychus Cinnabarinus (%) | |
| --- | --- | --- |
|  | 600 mg/L | 100 mg/L |
| CK3 | 56 | /// |
| CK4 | 59 | /// |
| CK5 | 58 | /// |

It can be seen from the above data that the compound having novel structure shown by the general formula I in the present invention shows good insecticidal activity against several common insects in the agricultural field. Moreover, at some low doses, the compounds show outstanding activity effects, which are better than the control compounds.

Other compounds shown by the general formula I of the present invention are tested accordingly according to the above determination manner of the biological activity, and may also have the corresponding activity.

We claim:
1. A substituted pyrimidine compound characterized by a formula shown by I-1:

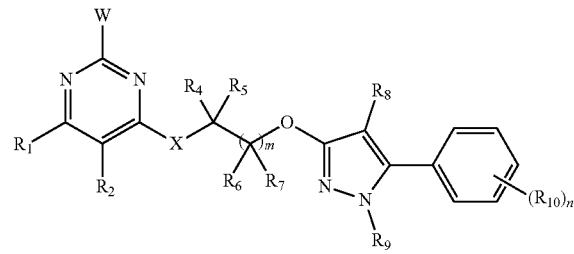

I-1 in the formula,
$R_1$ is selected from hydrogen, halogen, cyano, nitro, amino, carboxyl, $C_1$-$C_4$ alkyl, halogenated $C_1$-$C_4$ alkyl, $C_3$-$C_4$ cycloalkyl, $C_1$-$C_4$ alkoxyl, halogenated $C_1$-$C_4$ alkoxyl, $C_1$-$C_4$ alkylthio, $C_1$-$C_4$ alkylsulfinyl, $C_1$-$C_4$ alkylsulfonyl, halogenated $C_1$-$C_4$ alkylthio, $C_2$-$C_4$ alkenyl, halogenated $C_2$-$C_4$ alkenyl, $C_2$-$C_4$ alkynyl, halogenated $C_2$-$C_4$ alkynyl, $C_3$-$C_4$ alkenyloxy, halogenated $C_3$-$C_4$ alkenyloxy, $C_3$-$C_4$ alkynyloxy, halogenated $C_3$-$C_4$ alkynyloxy, $C_1$-$C_4$ alkylamino, di($C_1$-$C_4$ alkyl) amino, $C_1$-$C_4$ alkylaminocarbonyl, halogenated $C_1$-$C_4$ alkylaminocarbonyl, $C_1$-$C_4$ alkoxycarbonyl, halogenated $C_1$-$C_4$ alkoxycarbonyl, $C_1$-$C_4$ alkoxy $C_1$-$C_4$ alkyl or $C_1$-$C_4$ alkylthio $C_1$-$C_4$ alkyl;
$R_2$ is selected from hydrogen, halogen, cyano, nitro, amino, carboxyl, formyl, $C_1$-$C_4$ alkyl, halogenated $C_1$-$C_4$ alkyl, $C_1$-$C_4$ alkoxyl, or halogenated $C_1$-$C_4$ alkoxyl;
$R_1$ and $R_2$ can also form a five-membered ring or six-membered ring containing C, N, O or S together with a connected pyrimidine ring;
X is selected from $NR_3$, O or S;
$R_3$ is selected from hydrogen, hydroxyl, formyl, $C_1$-$C_4$ alkyl, halogenated $C_1$-$C_4$ alkyl, $C_1$-$C_4$ alkoxy, halogenated $C_1$-$C_4$ alkoxy, $C_3$-$C_4$ cycloalkyl, $C_1$-$C_4$ alkylthio, $C_2$-$C_4$ alkenylthio, $C_2$-$C_4$ alkenyl, $C_2$-$C_4$ alkynyl, halogenated $C_2$-$C_4$ alkenyl, halogenated $C_2$-$C_4$ alkynyl, $C_1$-$C_4$ alkoxy $C_1$-$C_4$ alkyl, halogenated $C_1$-$C_4$ alkoxy $C_1$-$C_4$ alkyl, $C_1$-$C_4$ alkylthio $C_1$-$C_4$ alkyl, halogenated $C_1$-$C_4$ alkylthio $C_1$-$C_4$ alkyl, $C_1$-$C_4$ alkylsulfinyl, halogenated $C_1$-$C_4$ alkylsulfinyl, $C_1$-$C_4$ alkylsulfonyl, halogenated $C_1$-$C_4$ alkylsulfonyl, $C_1$-$C_4$ alkylaminosulfonyl, di($C_1$-$C_4$ alkyl) aminosulfonyl, $C_1$-$C_4$ alkyl sulfonylaminocarbonyl, $C_1$-$C_4$ alkylcarbonylaminosulfonyl, $C_3$-$C_4$ cycloalkyloxycarbonyl, $C_1$-$C_4$ alkylcarbonyl, halogenated $C_1$-$C_4$ alkylcarbonyl, $C_1$-$C_4$ alkoxycarbonyl, halogenated $C_1$-$C_4$ alkoxycarbonyl, $C_1$-$C_4$ alkylcarbonyl $C_1$-$C_4$ alkyl, $C_1$-$C_4$ alkoxycarbonyl $C_1$-$C_4$ alkyl, $C_1$-$C_4$ alkylaminocarbonyl, di($C_1$-$C_4$ alkyl) aminocarbonyl, $C_2$-$C_4$ alkenyloxycarbonyl, $C_2$-$C_4$ alkynyloxycarbonyl, $C_1$-$C_4$ alkoxy $C_1$-$C_4$ alkoxycarbonyl, $C_1$-$C_4$ alkylaminothio, di($C_1$-$C_4$ alkyl) aminothio, and unsubstituted or substituted arylcarbonyl $C_1$-$C_4$ alkyl, arylcarbonyl, aryloxycarbonyl, aryl $C_1$-$C_4$ alkyloxycarbonyl, aryl $C_1$-$C_4$ alkyl, heteroarylcarbonyl $C_1$-$C_4$ alkyl, heteroarylcarbonyl, heteroaryloxycarbonyl, heteroaryl $C_1$-$C_4$ alkyloxycarbonyl and heteroaryl $C_1$-$C_4$ alkyl by 1-5 of the following groups, the following groups are halogen, nitro, cyano, $C_1$-$C_4$ alkyl, halogenated $C_1$-$C_4$ alkyl, $C_1$-$C_4$ alkoxy or halogenated $C_1$-$C_6$ alkoxy;

$R_4$ and $R_5$ are the same or different, and are respectively selected from hydrogen, halogen, $C_1$-$C_4$ alkyl, halogenated $C_1$-$C_4$ alkyl, $C_1$-$C_4$ alkoxy or halogenated $C_1$-$C_4$ alkoxy;

wherein $R_4$ and $R^5$ can also form a $C_3$-$C_4$ ring together with the connected C;

$R_6$ and $R_7$ are the same or different, and are respectively selected from hydrogen, halogen, $C_1$-$C_4$ alkyl, halogenated $C_1$-$C_4$ alkyl, $C_1$-$C_4$ alkoxyl or halogenated $C_1$-$C_4$ alkoxyl;

wherein $R_6$ and $R_7$ can also form a $C_3$-$C_4$ ring together with the connected C;

m is selected from an integer from 0 to 3;

$R_8$ is selected from hydrogen, cyano, halogen, $C_1$-$C_4$ alkyl, halogenated $C_1$-$C_4$ alkyl, $C_1$-$C_4$ alkoxycarbonyl, halogenated $C_1$-$C_4$ alkoxycarbonyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl, where the substituted aryl moiety includes one to five $R_{10}$ $R_9$ is selected from hydrogen, $C_1$-$C_4$ alkyl, $C_3$-$C_4$ cycloalkyl, halogenated $C_1$-$C_4$ alkyl, $C_1$-$C_4$ alkylcarbonyl, halogenated $C_1$-$C_4$ alkylcarbonyl, $C_1$-$C_4$ alkylsulfonyl, halogenated $C_1$-$C_4$ alkylsulfonyl, $C_1$-$C_4$ alkoxycarbonyl, $C_1$-$C_4$ alkoxy $C_1$-$C_4$ alkyl, $C_1$-$C_4$ alkoxycarbonyl $C_1$-$C_4$ alkyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl, where the substituted aryl moiety includes one to five $R_{10}$;

$R_{10}$ is selected from halogen, hydroxyl, amino, cyano, nitro, $C_1$-$C_4$ alkyl, halogenated $C_1$-$C_4$ alkyl, $C_1$-$C_4$ alkoxyl, halogenated $C_1$-$C_4$ alkoxy, $C_3$-$C_4$ cycloalkyl, $C_1$-$C_4$ alkylamino, halogenated $C_1$-$C_4$ alkylamino, di($C_1$-$C_4$ alkyl) amino, halogenated di($C_1$-$C_4$ alkyl) amino, C(=O)$NR_{12}R_{13}$, $C_1$-$C_4$ alkylthio, halogenated $C_1$-$C_4$ alkylthio, $C_2$-$C_4$ alkenyl, $C_2$-$C_4$ alkynyl, $C_2$-$C_4$ alkenyloxy, halogenated $C_2$-$C_4$ alkenyloxy, $C_2$-$C_4$ alkynyloxy, halogenated $C_2$-$C_4$ alkynyloxy, $C_1$-$C_4$ alkylsulfonyl, halogenated $C_1$-$C_4$ alkylsulfonyl, $C_1$-$C_4$ alkylcarbonyl, halogenated $C_1$-$C_4$ alkylcarbonyl, $C_1$-$C_4$ alkoxycarbonyl, halogenated $C_1$-$C_4$ alkoxycarbonyl, $C_1$-$C_4$ alkoxy $C_1$-$C_4$ alkyl, halogenated $C_1$-$C_4$ alkoxy $C_1$-$C_4$ alkyl, $C_1$-$C_4$ alkylthio $C_1$-$C_4$ alkyl, halogenated $C_1$-$C_4$ alkylthio $C_1$-$C_4$ alkyl, $C_1$-$C_4$ alkoxycarbonyl $C_1$-$C_4$ alkyl, halogenated $C_1$-$C_4$ alkoxycarbonyl $C_1$-$C_4$ alkyl, $C_1$-$C_4$ alkylthiocarbonyl $C_1$-$C_4$ alkyl, halogenated $C_1$-$C_4$ alkylthiocarbonyl $C_1$-$C_4$ alkyl, $C_1$-$C_4$ alkylcarbonyloxy, halogenated $C_1$-$C_4$ alkylcarbonyloxy, $C_1$-$C_4$ alkoxycarbonyloxy, halogenated $C_1$-$C_4$ alkoxycarbonyloxy, $C_1$-$C_4$ alkylsulfonyloxy, halogenated $C_1$-$C_4$ alkylsulfonyloxy, $C_1$-$C_4$ alkoxy $C_1$-$C_4$ alkoxy or halogenated $C_1$-$C_4$ alkoxy $C_1$-$C_4$ alkoxy;

n is selected from an integer from 0 to 5; when n is 0, a benzene ring has no substituent; when n is greater than 1, $R_{10}$ is the same or different;

$R_{11}$ and $R_{12}$ are the same or different, and are respectively selected from hydrogen, $C_1$-$C_{12}$ alkyl or halogenated $C_1$-$C_{12}$ alkyl;

W is selected from hydrogen, halogen, $C_1$-$C_4$ alkyl, halogenated $C_1$-$C_4$ alkyl, $C_3$-$C_4$ cycloalkyl, $C_1$-$C_4$ alkoxy, $C_1$-$C_4$ alkylthio or $C_1$-$C_4$ alkylsulfonyl;

or salt formed by the compound shown by general formula I-1 and hydrochloric acid, sulfuric acid, phosphoric acid, formic acid, acetic acid, trifluoroacetic acid, oxalic acid, methanesulfonic acid, p-toluenesulfonic acid, benzoic acid, phthalic acid, maleic acid, fumaric acid, sorbic acid, malic acid or citric acid.

2. The substituted pyrimidine compound according to claim 1, characterized in that the structure of the compound shown by the general formula I-1 is: I-1A, I-1B, I-1C or I-1D;

I-1A

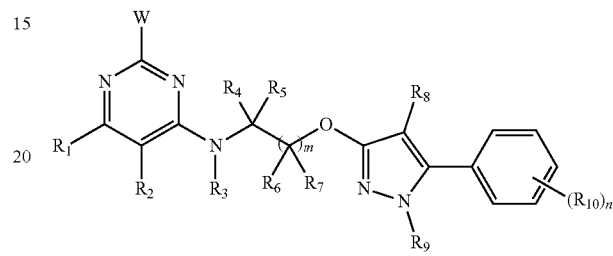

I-1B

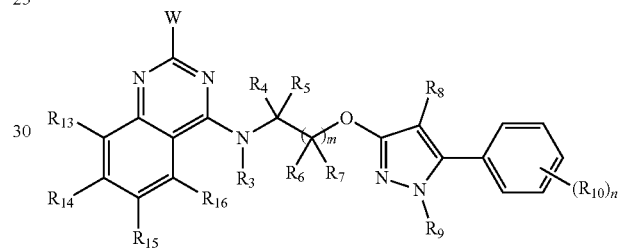

I-1C

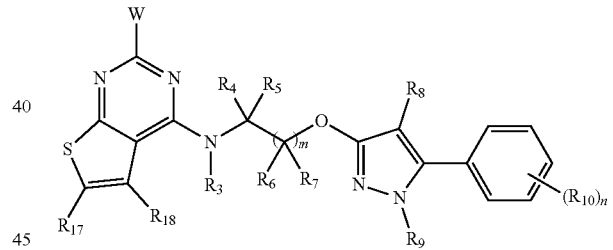

I-1D

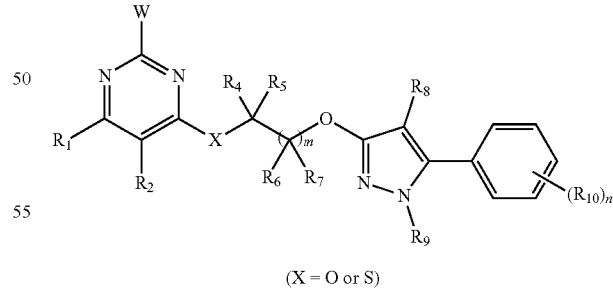

(X = O or S)

in the formula:

$R_4$ and $R_5$ are the same or different, and are respectively selected from hydrogen, halogen, $C_1$-$C_4$ alkyl, halogenated $C_1$-$C_4$ alkyl, $C_1$-$C_4$ alkoxyl or halogenated $C_1$-$C_4$ alkoxyl;

wherein $R_4$ and $R_5$ can also form a $C_3$-$C_4$ ring together with the connected C;

$R_6$ and $R_7$ are the same or different, and are respectively selected from hydrogen, halogen, $C_1$-$C_4$ alkyl, halogenated $C_1$-$C_4$ alkyl, $C_1$-$C_4$ alkoxyl or halogenated $C_1$-$C_4$ alkoxyl;

wherein $R_6$ and $R_7$ can also form a $C_3$-$C_4$ ring together with the connected C;

m is selected from an integer from 0 to 3;

$R_8$ and $R_9$ are the same or different, and are respectively selected from hydrogen, cyano, halogen, $C_1$-$C_4$ alkyl, halogenated $C_1$-$C_4$ alkyl, $C_1$-$C_4$ alkoxycarbonyl, halogenated $C_1$-$C_4$ alkoxycarbonyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl, where the substituted aryl moiety includes one to five $R_{10}$;

$R_{10}$ is selected from halogen, hydroxyl, amino, cyano, nitro, $C_1$-$C_4$ alkyl, halogenated $C_1$-$C_4$ alkyl, $C_1$-$C_4$ alkoxyl, halogenated $C_1$-$C_4$ alkoxy, $C_3$-$C_4$ cycloalkyl, $C_1$-$C_4$ alkylamino, halogenated $C_1$-$C_4$ alkylamino, di($C_1$-$C_4$ alkyl) amino, halogenated di($C_1$-$C_4$ alkyl) amino, C(=O)$NR_{12}R_{13}$, $C_1$-$C_4$ alkylthio, halogenated $C_1$-$C_4$ alkylthio, $C_2$-$C_4$ alkenyl, $C_2$-$C_4$ alkynyl, $C_2$-$C_4$ alkenyloxy, halogenated $C_2$-$C_4$ alkenyloxy, $C_2$-$C_4$ alkynyloxy, halogenated $C_2$-$C_4$ alkynyloxy, $C_1$-$C_4$ alkylsulfonyl, halogenated $C_1$-$C_4$ alkylsulfonyl, $C_1$-$C_4$ alkylcarbonyl, halogenated $C_1$-$C_4$ alkylcarbonyl, $C_1$-$C_4$ alkoxycarbonyl, halogenated $C_1$-$C_4$ alkoxycarbonyl, $C_1$-$C_4$ alkoxy $C_1$-$C_4$ alkyl, halogenated $C_1$-$C_4$ alkoxy $C_1$-$C_4$ alkyl, $C_1$-$C_4$ alkylthio $C_1$-$C_4$ alkyl, halogenated $C_1$-$C_4$ alkylthio $C_1$-$C_4$ alkyl, $C_1$-$C_4$ alkoxycarbonyl $C_1$-$C_4$ alkyl, halogenated $C_1$-$C_4$ alkoxycarbonyl $C_1$-$C_4$ alkyl, $C_1$-$C_4$ alkylthiocarbonyl $C_1$-$C_4$ alkyl, halogenated $C_1$-$C_4$ alkylthiocarbonyl $C_1$-$C_4$ alkyl, $C_1$-$C_4$ alkylcarbonyloxy, halogenated $C_1$-$C_4$ alkylcarbonyloxy, $C_1$-$C_4$ alkoxycarbonyloxy, halogenated $C_1$-$C_4$ alkoxycarbonyloxy, $C_1$-$C_4$ alkylsulfonyloxy, halogenated $C_1$-$C_4$ alkylsulfonyloxy, $C_1$-$C_4$ alkoxy $C_1$-$C_4$ alkoxy or halogenated $C_1$-$C_4$ alkoxy $C_1$-$C_4$ alkoxy;

n is selected from an integer from 0 to 5; when n is 0, a benzene ring has no substituent;

when n is greater than 1, $R_{10}$ is the same or different;

$R_{11}$ and $R_{12}$ are the same or different and are respectively selected from hydrogen, $C_1$-$C_4$ alkyl or halogenated $C_1$-$C_4$ alkyl;

W is selected from hydrogen, halogen, $C_1$-$C_4$ alkyl, halogenated $C_1$-$C_4$ alkyl, $C_3$-$C_4$ cycloalkyl, $C_1$-$C_4$ alkoxy, $C_1$-$C_4$ alkylthio or $C_1$-$C_4$ alkylsulfonyl;

moreover, when the compound has the general formula I-1D, X is O or S;

when the compounds have the general formulas I-1A and I-1D, $R_1$ is selected from hydrogen, halogen, cyano, nitro, amino, carboxyl, $C_1$-$C_4$ alkyl, halogenated $C_1$-$C_4$ alkyl, $C_3$-$C_4$ cycloalkyl, $C_1$-$C_4$ alkoxyl, halogenated $C_1$-$C_4$ alkoxyl, $C_1$-$C_4$ alkylthio, halogenated $C_1$-$C_4$ alkylthio, $C_1$-$C_4$ alkylsulfinyl, $C_1$-$C_4$ alkylsulfonyl, $C_2$-$C_4$ alkenyl, halogenated $C_2$-$C_4$ alkenyl, $C_2$-$C_4$ alkynyl, halogenated $C_2$-$C_4$ alkynyl, $C_3$-$C_4$ alkenyloxy, halogenated $C_3$-$C_4$ alkenyloxy, $C_3$-$C_4$ alkynyloxy, halogenated $C_3$-$C_4$ alkynyloxy, $C_1$-$C_4$ alkylamino, di($C_1$-$C_4$ alkyl) amino, $C_1$-$C_4$ alkylaminocarbonyl, halogenated $C_1$-$C_4$ alkylaminocarbonyl, $C_1$-$C_4$ alkoxycarbonyl, halogenated $C_1$-$C_4$ alkoxycarbonyl, $C_1$-$C_4$ alkoxy $C_1$-$C_4$ alkyl or $C_1$-$C_4$ alkylthio $C_1$-$C_4$ alkyl;

$R_2$ is selected from hydrogen, halogen, cyano, nitro, amino, carboxyl, formyl, $C_1$-$C_4$ alkyl, halogenated $C_1$-$C_4$ alkyl, $C_1$-$C_{12}$ alkoxy or halogenated $C_1$-$C_4$ alkoxy;

when the compounds have the general formulas I-1A, I-1B and I-1C, $R_3$ is selected from hydrogen, hydroxyl, formyl, $C_1$-$C_4$ alkyl, halogenated $C_1$-$C_4$ alkyl, $C_1$-$C_4$ alkoxy, halogenated $C_1$-$C_4$ alkoxy, $C_3$-$C_4$ cycloalkyl, $C_1$-$C_4$ alkylthio, $C_2$-$C_4$ alkenylthio, $C_2$-$C_4$ alkenyl, $C_2$-$C_4$ alkynyl, halogenated $C_2$-$C_4$ alkenyl, halogenated $C_2$-$C_4$ alkynyl, $C_1$-$C_4$ alkoxy $C_1$-$C_4$ alkyl, halogenated $C_1$-$C_4$ alkoxy $C_1$-$C_4$ alkyl, $C_1$-$C_4$ alkylthio $C_1$-$C_4$ alkyl, halogenated $C_1$-$C_4$ alkylthio $C_1$-$C_4$ alkyl, $C_1$-$C_4$ alkylsulfinyl, halogenated $C_1$-$C_4$ alkylsulfinyl, $C_1$-$C_4$ alkylsulfonyl, halogenated $C_1$-$C_4$ alkylsulfonyl, $C_1$-$C_4$ alkylaminosulfonyl, di($C_1$-$C_4$ alkyl) aminosulfonyl, $C_1$-$C_4$ alkyl sulfonylaminocarbonyl, $C_1$-$C_4$ alkylcarbonylaminosulfonyl, $C_3$-$C_4$ cycloalkyloxycarbonyl, $C_1$-$C_4$ alkylcarbonyl, halogenated $C_1$-$C_4$ alkylcarbonyl, $C_1$-$C_4$ alkoxycarbonyl, halogenated $C_1$-$C_4$ alkoxycarbonyl, $C_1$-$C_4$ alkylcarbonyl $C_1$-$C_4$ alkyl, $C_1$-$C_4$ alkoxycarbonyl $C_1$-$C_4$ alkyl, $C_1$-$C_4$ alkylaminocarbonyl, di($C_1$-$C_4$ alkyl) aminocarbonyl, $C_2$-$C_4$ alkenyloxycarbonyl, $C_2$-$C_4$ alkynyloxycarbonyl, $C_1$-$C_4$ alkoxy $C_1$-$C_4$ alkoxycarbonyl, $C_1$-$C_4$ alkylaminothio, di($C_1$-$C_4$ alkyl) aminothio, and unsubstituted or substituted arylcarbonyl $C_1$-$C_4$ alkyl, arylcarbonyl, aryloxycarbonyl, aryl $C_1$-$C_4$ alkyloxycarbonyl, aryl $C_1$-$C_4$ alkyl, heteroarylcarbonyl $C_1$-$C_4$ alkyl, heteroarylcarbonyl, heteroaryloxycarbonyl, heteroaryl $C_1$-$C_4$ alkyloxycarbonyl and heteroaryl $C_1$-$C_4$ alkyl by 1-5 of the following groups, the following groups are halogen, nitro, cyano, $C_1$-$C_4$ alkyl, halogenated $C_1$-$C_4$ alkyl, $C_1$-$C_4$ alkoxy or halogenated $C_1$-$C_4$ alkoxy;

when the compound has the general formula I-1B, $R_{13}$, $R_{14}$, $R_{15}$ and $R_{16}$ are the same or different and are respectively selected from hydrogen, halogen, hydroxyl, amino, cyano, nitro, $C_1$-$C_4$ alkyl, halogenated $C_1$-$C_4$ alkyl, $C_1$-$C_4$ alkoxy, halogenated $C_1$-$C_4$ alkoxy or $C_3$-$C_4$ cycloalkyl;

when the compound has the general formula I-1C, $R_{17}$ and $R_{18}$ are the same or different and are selected from hydrogen, halogen, $C_1$-$C_4$ alkyl, halogenated $C_1$-$C_4$ alkyl, $C_1$-$C_4$ alkoxyl, halogenated $C_1$-$C_4$ alkoxyl, $C_1$-$C_4$ alkylthio, halogenated $C_1$-$C_4$ alkylthio, $C_3$-$C_4$ cycloalkyl, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$;

or salt formed by the compounds shown by general formulas I-1A, I-1B, I-1C and I-1D and hydrochloric acid, sulfuric acid, phosphoric acid, formic acid, acetic acid, trifluoroacetic acid, oxalic acid, methanesulfonic acid, p-toluenesulfonic acid, benzoic acid, phthalic acid, maleic acid, fumaric acid, sorbic acid, malic acid or citric acid.

3. The substituted pyrimidine compound according to claim 2, characterized in that in the compounds shown by the general formulas I-1A, I-1B, I-1C and I-1D:

$R_4$ and $R_5$ are the same or different and are selected from hydrogen, fluorine, chlorine, bromine, iodine, methyl, ethyl, n-propyl, isopropyl, n-butyl, sec-butyl, isobutyl, tert-butyl, methoxyl, ethoxyl, n-propoxy, isopropoxy, n-butoxy, sec-butoxy, isobutoxy or tert-butoxy;

$R_6$ and $R_7$ are the same or different and are respectively selected from hydrogen, fluorine, chlorine, bromine, iodine, methyl, ethyl, n-propyl, isopropyl, n-butyl, sec-butyl, isobutyl, tert-butyl, methoxyl, ethoxyl, n-propoxy, isopropoxy, n-butoxy, sec-butoxy, isobutoxy or tert-butoxy;

$R_8$ and $R_9$ are the same or different and are respectively selected from hydrogen, cyano, fluorine, chlorine, bromine, iodine, methyl, ethyl or trifluoromethyl;

$R_{10}$ is selected from fluorine, chlorine, bromine, iodine, cyano, amino, nitro, methyl, ethyl, n-propyl, isopropyl, n-butyl, sec-butyl, isobutyl, tert-butyl, trifluoromethyl, trichloromethyl, difluoromonochloromethyl, dichloromonofluoromethyl, methoxyl, ethoxyl, n-propoxy, isopropoxy, n-butoxy, sec-butoxy, isobutoxy, t-butoxy, methylthio, ethylthio, trifluoromethoxy, trifluoroethoxy, methoxycarbonyl, ethoxycarbonyl, aminocarbonyl, methylaminocarbonyl, ethylaminocarbonyl or dimethylaminocarbonyl;

n is selected from an integer from 0 to 5; when n is 0, a benzene ring has no substituent; when n is greater than 1, $R_{10}$ may be the same or different;

W is selected from hydrogen, fluorine, chlorine, bromine, iodine, methyl, ethyl, n-propyl, isopropyl, n-butyl, sec-butyl, isobutyl, t-butyl, monofluoromethyl, monochloromethyl, difluoromethyl, trifluoromethyl, trifluoroethyl, methoxyl, ethoxyl, methylthio, ethylthio, methyl sulfonyl or ethyl sulfonyl;

moreover, when the compounds have the general formulas I-1A and I-1D, $R_1$ is selected from hydrogen, fluorine, chlorine, bromine, iodine, cyano, nitro, amino, carboxyl, methyl, ethyl, n-propyl, isopropyl, n-butyl, sec-butyl, isobutyl, tert-butyl, monofluoromethyl, monochloromethyl, difluoromethyl, trifluoromethyl, trifluoroethyl, methoxymethyl, ethoxymethyl or trifluoroethoxymethyl;

$R_2$ is selected from hydrogen, fluorine, chlorine, bromine, iodine, cyano, nitro, amino, carboxyl, formyl, methyl, ethyl, methoxy, ethoxy or trifluoroethoxy;

when the compounds have the general formulas I-1A, I-1B and I-1C, $R_3$ is selected from hydrogen, hydroxyl, formyl, acetyl, propanoyl, butyryl, trifluoroacetyl, benzoyl, methyl, ethyl, n-propyl, isopropyl, n-butyl, sec-butyl, isobutyl, tert-butyl, trifluoromethyl, trifluoroethyl, methoxyl, ethoxyl, trifluoroethoxy, cyclopropyloxy, methylthio, ethylthio, allyl, propargyl, mesyl, ethyl sulfonyl, trifluoroethylsulfonyl, methylaminosulfonyl, ethylaminosulfonyl, dimethylaminosulfonyl, diethylaminosulfonyl, methylsulfonylaminocarbonyl, methoxycarbonyl, ethoxycarbonyl, propoxycarbonyl, isopropoxycarbonyl, methylaminocarbonyl, dimethylaminocarbonyl, vinyl oxycarbonyl, ethynyloxycarbonyl, methylaminothio, ethylaminothio or dimethylaminothio;

when the compound has the general formula I-1B, $R_{13}$, $R_{14}$, $R_{15}$ and $R_{16}$ are the same or different and are respectively selected from hydrogen, fluorine, chlorine, bromine, iodine, amino, cyano, nitro, methyl, ethyl, n-propyl, isopropyl, n-butyl, sec-butyl, isobutyl, tert-butyl, trifluoromethyl, trichloromethyl, difluoromonochloromethyl, dichloromonofluoromethyl, methoxy, ethoxy, n-propoxy, isopropoxy, n-butoxy, sec-butoxy, isobutoxy, t-butoxy, trifluoromethoxy or trifluoroethoxy;

when the compound has the general formula I-1C, $R_{17}$ and $R_{18}$ are the same or different and are respectively selected from hydrogen, fluorine, chlorine, bromine, iodine, methyl, ethyl, n-propyl, isopropyl, n-butyl, sec-butyl, isobutyl, tert-butyl, trifluoromethyl, trichloromethyl, difluoromonochloromethyl, dichloromonofluoromethyl, trifluoroethyl, methoxyl, ethoxyl, n-propoxy, isopropoxy, n-butoxy, sec-butoxy, isobutoxy, tert-butoxy, trifluoromethoxy, trifluoroethoxy, and unsubstituted or substituted aryl, arylmethyl, arylcarbonyl, arylmethylcarbonyl, aryloxycarbonyl, heteroaryl, heteroarylmethyl, heteroarylcarbonyl, heteroarylmethylcarbonyl or heteroaryloxycarbonyl by one to five $R_{10}$.

4. The substituted pyrimidine compound according to claim 3, characterized in that in the compounds shown by the general formulas I-1A, I-1B, I-1C and I-1D:

$R_4$ and $R_5$ are the same or different, and are respectively selected from hydrogen, fluorine, chlorine, bromine or methyl;

$R_6$ and $R_7$ are selected from hydrogen;

$R_8$ is hydrogen or methyl;

$R_9$ is selected from hydrogen or methyl;

$R_{10}$ is selected from fluorine, chlorine, bromine, iodine, cyano, nitro, methyl, ethyl, trifluoromethyl, methoxy, methylthio or trifluoromethoxy;

n is selected from an integer from 0 to 5; when n is 0, the benzene ring has no substituent;

when n is greater than 1, $R_{10}$ can be the same or different;

W is selected from hydrogen, fluorine, chlorine, bromine, iodine or methyl;

moreover, when the compounds have the general formulas I-1A and I-1D, $R_1$ is selected from hydrogen, fluorine, chlorine, bromine, iodine, methyl, ethyl or difluoromethyl;

$R_2$ is selected from hydrogen, fluorine, chlorine, bromine, iodine, nitro, amino, formyl, methyl, ethyl, methoxy or ethoxy;

when the compounds have the general formulas I-1A, I-1B and I-1C, $R_3$ is selected from hydrogen, methyl, acetyl, trifluoroacetyl, methoxy, methylthio, allyl, methanesulfonyl, methylaminosulfonyl, dimethylaminosulfonyl, methoxycarbonyl, methylaminocarbonyl, dimethylaminocarbonyl, methylaminothio or dimethylaminothio;

when the compound has the general formula I-1B, $R_{13}$, $R_{14}$, $R_{15}$ and $R_{16}$ are the same or different and are respectively selected from hydrogen, fluorine, chlorine, bromine, iodine or methyl;

when the compound has the general formula I-1C, $R_{17}$ and $R_{18}$ are the same or different and are respectively selected from hydrogen, fluorine, chlorine, bromine or iodine.

5. The substituted pyrimidine compound according to claim 4, characterized in that in the compounds shown by the general formulas I-1A, I-1B, I-1C and I-1D:

$R_4$ and $R_5$ can be the same or different, and are respectively selected from hydrogen or methyl;

$R_6$ and $R_7$ are selected from hydrogen;

$R_8$ is hydrogen or methyl;

$R_9$ is selected from methyl;

$R_{10}$ is selected from fluorine, chlorine, bromine, iodine, cyano, nitro, methyl, ethyl, trifluoromethyl, methoxy, methylthio or trifluoromethoxy;

n is selected from an integer from 1 to 5; when n is greater than 1, $R_{10}$ can be the same or different;

W is selected from hydrogen, fluorine, chlorine, bromine or iodine;

moreover, when the compounds have the general formulas I-1A and I-1D, $R_1$ is selected from fluorine, chlorine, bromine, iodine, methyl, ethyl or difluoromethyl;

$R_2$ is selected from fluorine, chlorine, bromine, iodine, nitro, amino, formyl, methyl or methoxyl;

when the compounds have the general formulas I-1A, I-1B and I-1C, $R_3$ is selected from hydrogen, methyl, acetyl, methoxyl, allyl, methanesulfonyl, methoxycarbonyl, methylaminocarbonyl, dimethylaminocarbonyl or dimethylaminothio;

when the compound has the general formula 1-1B, $R_{13}$, $R_{14}$, $R_{15}$ and $R_{16}$ are selected from hydrogen;

when the compound has the general formula I-1C, $R_{17}$ is selected from hydrogen;

$R_{18}$ is selected from chlorine.

6. A fungicidal, insecticidal and acaricidal composition comprising, the substituted pyrimidine compound of claim 1 as an active ingredient, wherein the weight percentage of the active ingredient in the composition is 0.1-99%.

* * * * *